(12) United States Patent
Eckhardt

(10) Patent No.: US 8,927,531 B2
(45) Date of Patent: Jan. 6, 2015

(54) INDANYLOXYDIHYDROBENZOFURANYLACETIC ACIDS

(71) Applicant: Matthias Eckhardt, Biberach an der Riss (DE)

(72) Inventor: Matthias Eckhardt, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 2 days.

(21) Appl. No.: 14/170,660

(22) Filed: Feb. 3, 2014

(65) Prior Publication Data
US 2014/0221349 A1 Aug. 7, 2014

(30) Foreign Application Priority Data

Feb. 6, 2013 (EP) ..................................... 13154261

(51) Int. Cl.
| | | |
|---|---|---|
| A61K 31/343 | (2006.01) | |
| C07D 307/77 | (2006.01) | |
| C07D 307/83 | (2006.01) | |
| A61K 31/4025 | (2006.01) | |
| A61K 31/435 | (2006.01) | |
| A61K 31/437 | (2006.01) | |
| A61K 31/4525 | (2006.01) | |
| A61K 31/496 | (2006.01) | |
| A61K 31/5377 | (2006.01) | |
| A61K 31/541 | (2006.01) | |
| A61K 31/553 | (2006.01) | |
| A61K 45/06 | (2006.01) | |
| C07D 405/12 | (2006.01) | |
| C07D 491/107 | (2006.01) | |
| C07D 513/04 | (2006.01) | |
| C07D 413/12 | (2006.01) | |
| C07D 451/02 | (2006.01) | |
| C07D 471/04 | (2006.01) | |
| C07D 487/04 | (2006.01) | |
| C07D 495/04 | (2006.01) | |
| C07D 498/04 | (2006.01) | |
| C07D 498/08 | (2006.01) | |
| C07D 307/80 | (2006.01) | |

(52) U.S. Cl.
CPC .......... *C07D 307/83* (2013.01); *A61K 31/4025* (2013.01); *A61K 31/435* (2013.01); *A61K 31/437* (2013.01); *A61K 31/4525* (2013.01); *A61K 31/496* (2013.01); *A61K 31/5377* (2013.01); *A61K 31/541* (2013.01); *A61K 31/553* (2013.01); *A61K 45/06* (2013.01); *C07D 405/12* (2013.01); *C07D 491/107* (2013.01); *C07D 513/04* (2013.01); *C07D 413/12* (2013.01); *C07D 451/02* (2013.01); *C07D 471/04* (2013.01); *C07D 487/04* (2013.01); *C07D 495/04* (2013.01); *C07D 498/04* (2013.01); *C07D 498/08* (2013.01); *C07D 307/80* (2013.01)
USPC .......................................... 514/183; 544/224

(58) Field of Classification Search
CPC ............. A61K 31/5377; A61K 31/343; C07D 307/83; C07D 307/77
See application file for complete search history.

(56) References Cited

U.S. PATENT DOCUMENTS

2013/0289074 A1* 10/2013 Himmelsbach et al. ...... 514/337

FOREIGN PATENT DOCUMENTS

WO 2012072691 A1 6/2012

OTHER PUBLICATIONS

Burant, C. "Activation of GPR40 as a Therapeutic Target for the Treatment of Type 2 Diabetes." Diabetes Care. (Aug. 2013), vol. 36, Supplement 2, pp. 5175-5179.*
Christiansen, E., et al. "Free Fatty Acid Receptor 1 (FFA1/GPR40) Agonists: Mesylpropoxy Appendage Lowers Lipophilicity and Improves ADME Properties." J. Med. Chem. (2012), vol. 55, pp. 6624-6628.*
Healthgrades.com "Metabolic Disorders." © 2014. Available from: < http://www.healthgrades.com/conditions/metabolic-disorders >.*
Mayo Clinic. "Type 2 Diabetes Mellitus." © 2014. Available from: < http://www.mayoclinic.org/diseases-conditions/type-2-diabetes/basics/treatment/con-20031902?p=1 >.*
WebMD. "Drugs & Medications Search: Type 2 Diabetes." (c) 2014. Available from: < http://www.webmd.com/drugs/condition-594-Type+2+Diabetes+Mellitus.aspx >.*

(Continued)

*Primary Examiner* — Andrew D Kosar
*Assistant Examiner* — John S Kenyon
(74) *Attorney, Agent, or Firm* — Michael P. Morris; Timothy X. Witkowski

(57) ABSTRACT

Compounds of general formula I

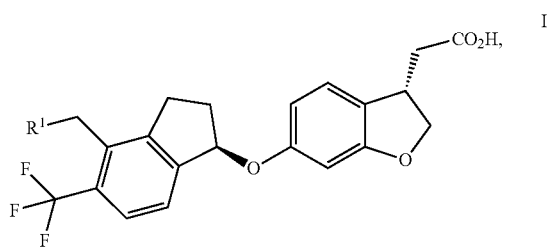

wherein the group $R^1$ is defined as in claim 1, which have valuable pharmacological properties, in particular bind to the GPR40 receptor and modulate its activity. The compounds are suitable for treatment and prevention of diseases which can be influenced by this receptor, such as metabolic diseases, in particular diabetes type 2.

15 Claims, No Drawings

(56) References Cited

OTHER PUBLICATIONS

Mayo Clinic. "Heart Disease." © 2014. Available from: < http://www.mayoclinic.org/diseases-conditions/heart-disease/basics/prevention/con-20034056 >.*

WebMD. "Common Heart Disease Drugs." © 2014. Available from: < http://www.webmd.com/heart-disease/common-medicine-heart-disease-patients >.*

International Search Report, PCTISA220 for PCT/EP14051878 mailed Mar. 3, 2014.

Kaku, "Fasiglifam as a new potential treatment option for patients with Type 2 diabetes", Informa Healthcare, 2013, p. 2591-2600.

Nature Reviews, Drug Discovery, "Lead GPR40 agonist bites the dust", vol. 13, 2014, p. 91.

* cited by examiner

INDANYLOXYDIHYDROBENZOFURANYLACETIC ACIDS

RELATED APPLICATION

This application claims priority to European Patent Application No. 13154261.5, filed Feb. 5, 2013, the contents of which are hereby incorporated by reference in its entirety.

FIELD OF THE INVENTION

The present invention relates to novel indanyloxydihydrobenzofuranylacetic acids that are agonists of the G-protein coupled receptor 40 (GPR40, also known as free fatty acid receptor FFAR 1), to processes for their preparation, to pharmaceutical compositions containing these compounds and to their medical use for the prophylaxis and/or treatment of diseases which can be influenced by the modulation of the function of GPR40. Particularly, the pharmaceutical compositions of the invention are suitable for the prophylaxis and/or therapy of metabolic diseases, such as diabetes, more specifically type 2 diabetes mellitus, and conditions associated with the disease, including insulin resistance, obesity, cardiovascular disease and dyslipidemia.

BACKGROUND OF THE INVENTION

Metabolic diseases are diseases caused by an abnormal metabolic process and may either be congenital due to an inherited enzyme abnormality or acquired due to a disease of an endocrine organ or failure of a metabolically important organ such as the liver or the pancreas.

Diabetes mellitus is a disease state or process derived from multiple causative factors and is defined as a chronic hyperglycemia associated with resulting damages to organs and dysfunctions of metabolic processes. Depending on its etiology, one differentiates between several forms of diabetes, which are either due to an absolute (lacking or decreased insulin secretion) or to a relative lack of insulin. Diabetes mellitus Type I (IDDM, insulin-dependent diabetes mellitus) generally occurs in adolescents under 20 years of age. It is assumed to be of auto-immune etiology, leading to an insulitis with the subsequent destruction of the beta cells of the islets of Langerhans which are responsible for the insulin synthesis. In addition, in latent autoimmune diabetes in adults (LADA; Diabetes Care. 8: 1460-1467, 2001) beta cells are being destroyed due to autoimmune attack. The amount of insulin produced by the remaining pancreatic islet cells is too low, resulting in elevated blood glucose levels (hyperglycemia). Diabetes mellitus Type II generally occurs at an older age. It is above all associated with a resistance to insulin in the liver and the skeletal muscles, but also with a defect of the islets of Langerhans. High blood glucose levels (and also high blood lipid levels) in turn lead to an impairment of beta cell function and to an increase in beta cell apoptosis.

Persistent or inadequately controlled hyperglycemia is associated with a wide range of pathologies. Diabetes is a very disabling disease, because today's common antidiabetic drugs do not control blood sugar levels well enough to completely prevent the occurrence of high and low blood sugar levels. Out of range blood sugar levels are toxic and cause long-term complications for example retinopathy, renopathy, neuropathy and peripheral vascular disease. There is also a host of related conditions, such as obesity, hypertension, stroke, heart disease and hyperlipidemia, for which persons with diabetes are substantially at risk.

Obesity is associated with an increased risk of follow-up diseases such as cardiovascular diseases, hypertension, diabetes, hyperlipidemia and an increased mortality. Diabetes (insulin resistance) and obesity are part of the "metabolic syndrome" which is defined as the linkage between several diseases (also referred to as syndrome X, insulin-resistance syndrome, or deadly quartet). These often occur in the same patients and are major risk factors for development of diabetes type II and cardiovascular disease. It has been suggested that the control of lipid levels and glucose levels is required to treat diabetes type II, heart disease, and other occurrences of metabolic syndrome (see e.g., Diabetes 48: 1836-1841, 1999; JAMA 288: 2209-2716, 2002).

The free fatty acid receptor GPR40 (also referred to as either FFAR, FFAR1, or FFA1) is a cell-surface receptor and a member of the gene superfamily of G-protein coupled receptors, which was first identified as a so-called orphan receptor, i.e. a receptor without a known ligand, based on the predicted presence of seven putative transmembrane regions in the corresponding protein (Sawzdargo et al. (1997) Biochem. Biophys. Res. Commun. 239: 543-547). GPR40 is found to be highly expressed in several particular cell types: the pancreatic 13 cells and insulin-secreting cell lines, as well as in enteroendocrine cells, taste cells, and is reported to be expressed in immune cells, splenocytes, and in the human and monkey brain. Meanwhile, fatty acids of varying chain lengths are thought to represent the endogenous ligands for GPR40, activation of which is linked primarily to the modulation of the Gq family of intra-cellular signaling G proteins and concomitant induction of elevated calcium levels, although activation of Gs- and Gi-proteins to modulate intracellular levels of cAMP have also been reported. GPR40 is activated especially by long-chain FFA, particularly oleate, as well as the PPAR-gamma agonist rosiglitazone.

It has been recognized that the fatty acids that serve as activators for GPR40 augment the elevated plasma glucose-induced secretion of insulin through GPR40 receptors that are expressed in the insulin secreting cells (Itoh et al. (2003) Nature 422: 173-176; Briscoe et al. (2003) J. Biol. Chem. 278: 11303-11311; Kotarsky et al. (2003) Biochem. Biophys. Res. Commun. 301: 406-410). Despite initial controversy, the use of GPR40 agonist appears to be the appropriate for increasing insulin release for the treatment of diabetes (see e.g. Diabetes 2008, 57, 2211; J. Med. Chem. 2007, 50, 2807). Typically, long term diabetes therapy leads to the gradual diminution of islet activity, so that after extended periods of treatment Type 2 diabetic patients need treatment with daily insulin injections instead. GPR40 agonists may have the potential to restore or preserve islet function, therefore, GPR40 agonists may be beneficial also in that that they may delay or prevent the diminution and loss of islet function in a Type 2 diabetic patient.

It is well established that the incretins GLP-1 (glucagon-like peptide-1) and GIP (glucose-dependent insulinotropic peptide; also known as gastric inhibitory peptide) stimulate insulin secretion and are rapidly inactivated in vivo by DPP-4. These peptidyl hormones are secreted by endocrine cells that are located in the epithelium of the small intestine. When these endocrine cells sense an increase in the concentration of glucose in the lumen of the digestive tract, they act as the trigger for incretin release. Incretins are carried through the circulation to beta cells in the pancreas and cause the beta cells to secrete more insulin in anticipation of an increase of blood glucose resulting from the digesting meal. Further studies indicating that the GPR40 modulatory role on the release of incretins from the enteroendocrine cells, including CCK, GLP-1, GIP, PYY, and possibly others, suggest that GPR40 modulators may contribute to enhanced insulin release from the pancreatic beta cells also indirectly by e.g. a synergistic effect of GLP-1 and possibly GIP on the insulin release, and the other release incretins may also contribute to an overall beneficial contribution of GPR40 modulation on metabolic diseases. The indirect contributions of GPR40 modulation on insulin release through the elevation of plasma levels of incretins may be further augmented by the coadministration of inhibitors of the enzymes responsible for the incretin degradation, such as inhibitors of DPP-4.

Insulin imbalances lead to conditions such as type II diabetes mellitus, a serious metabolic disease. The modulation of the function of GPR40 in modulating insulin secretion indicates the therapeutic agents capable of modulating GPR40 function could be useful for the treatment of disorders such as diabetes and conditions associated with the disease, including insulin resistance, obesity, cardiovascular disease and dyslipidemia.

OBJECT OF THE PRESENT INVENTION

The object of the present invention is to provide new compounds, hereinafter described as compounds of formula I, in particular new indanyloxydihydrobenzofuranylacetic acids, which are active with regard to the G-protein-coupled receptor GPR40, notably are agonists of the G-protein-coupled receptor GPR40.

A further object of the present invention is to provide new compounds, in particular new indanyloxydihydrobenzofuranylacetic acids, which have an activating effect on the G-protein-coupled receptor GPR40 in vitro and/or in vivo and possess suitable pharmacological and pharmacokinetic properties to use them as medicaments.

A further object of the present invention is to provide effective GPR40 agonists, in particular for the treatment of metabolic disorders, for example diabetes, dyslipidemia and/or obesity.

A further object of the present invention is to provide methods for treating a disease or condition mediated by the activation the G-protein-coupled receptor GPR40 in a patient.

A further object of the present invention is to provide a pharmaceutical composition comprising at least one compound according to the invention.

A further object of the present invention is to provide a combination of at least one compound according to the invention with one or more additional therapeutic agents.

Further objects of the present invention become apparent to the one skilled in the art by the description hereinbefore and in the following and by the examples.

GPR40 modulators are known in the art, for example, the compounds disclosed in WO 2004041266 (EP 1559422), WO 2007033002, WO 2009157418 and WO 2012072691. The indanyloxydihydrobenzofuranylacetic acids of the present invention may provide several advantages, such as enhanced potency, high metabolic and/or chemical stability, high selectivity and tolerability, enhanced solubility, and the possibility to form stable salts. In particular, the present invention provides compounds of superior stability in acidic aqueous media compared to related compounds disclosed in WO 2012072691.

SUMMARY OF THE INVENTION

In a first aspect the invention relates to compounds of formula I

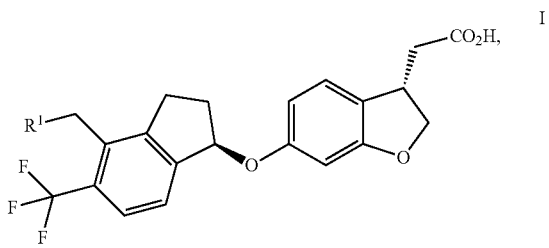

wherein
$R^1$ is selected from the group $R^1$-G1 consisting of a monocyclic or bicyclic group having 5 to 12 ring member atoms of which 4 to 11 ring members are C atoms and 1 to 3 ring members are heteroatoms selected from N and $NR^N$, or
1 or 2 ring members are heteroatoms selected from N and $NR^N$ and 1 ring member is selected from O and S, or
1 ring member is N and 2 ring members are independently selected from O and S, with the proviso that no O—O, S—S or S—O bond is formed,
  wherein the ring member atom attached to the —$CH_2$— group in formula I is a N atom,
  wherein 1 $CH_2$ ring member attached to a ring member N atom is optionally replaced by a —C(=O)— group,
  wherein the monocyclic or bicyclic group is saturated or partially unsaturated, with the proviso that in bicyclic groups the ring attached to the —$CH_2$— group in formula I must not be aromatic, and
  wherein the bicyclic group may be a fused, bridged or spiro ring system;
  wherein any of these groups is optionally and independently substituted with 1 to 3 $R^2$ groups;
$R^2$ is selected from the group $R^2$-G1 consisting of F, Cl, Br, I, $C_{1-4}$-alkyl, NC—, HO—$C_{1-4}$-alkyl, HO—, $C_{1-4}$-alkyl-O—, $C_{1-4}$-alkyl-O—$C_{1-4}$-alkyl, $C_{1-4}$-alkyl-S—, $C_{1-4}$-alkyl-S(=O)—, $C_{1-4}$-alkyl-S(=O)$_2$—, $C_{3-6}$-cycloalkyl-, and $C_{3-6}$-cycloalkyl-O—, wherein any alkyl and cycloalkyl group or submoiety is optionally substituted with 1 to 3 F atoms; and
$R^N$ is selected from the group $R^N$-G1 consisting of H, $C_{1-4}$-alkyl-, $C_{1-4}$-alkyl-C(O)—, and $C_{1-4}$-alkyl-O—O(O)—;
wherein in any definition mentioned hereinbefore and if not specified otherwise, any alkyl group or sub-group may be straight-chained or branched,
the isoforms, tautomers, stereoisomers, metabolites, prodrugs, solvates, hydrates, and the salts thereof, particularly the physiologically acceptable salts thereof with inorganic or organic acids or bases, or the combinations thereof.

The extension -Gn used within the definitions is meant to identify genus n of the respective substituent. For example, $R^1$-G1 defines genus 1 of the substituent $R^1$.

In a further aspect this invention relates to a pharmaceutical composition, comprising one or more compounds of general formula I or one or more pharmaceutically acceptable salts thereof according to the invention, optionally together with one or more inert carriers and/or diluents.

In a further aspect this invention relates to a method for treating diseases or conditions which are mediated by activating the G-protein-coupled receptor GPR40 in a patient in need thereof characterized in that a compound of general formula I or a pharmaceutically acceptable salt thereof is administered to the patient.

According to another aspect of the invention, there is provided a method for treating a metabolic disease or disorder, such as diabetes, dyslipidemia and/or obesity, in a patient in need thereof characterized in that a therapeutically effective amount of a compound of general formula I or a pharmaceutically acceptable salt thereof is administered to the patient.

According to another aspect of the invention, there is provided the use of a compound of the general formula I or a pharmaceutically acceptable salt thereof for the manufacture of a medicament for a therapeutic method as described hereinbefore and hereinafter.

According to another aspect of the invention, there is provided a compound of the general formula I or a pharmaceutically acceptable salt thereof for use in a therapeutic method as described hereinbefore and hereinafter.

In a further aspect this invention relates to a method for treating a disease or condition mediated by the activation of the G-protein-coupled receptor GPR40 in a patient that includes the step of administering to the patient in need of such treatment a therapeutically effective amount of a compound of the general formula I or a pharmaceutically acceptable salt thereof in combination with a therapeutically effective amount of one or more additional therapeutic agents.

In a further aspect this invention relates to the use of a compound of the general formula I or a pharmaceutically acceptable salt thereof in combination with one or more additional therapeutic agents for the treatment of diseases or conditions which are mediated by the activation of the G-protein-coupled receptor GPR40.

In a further aspect this invention relates to a pharmaceutical composition which comprises a compound according to general formula I or a pharmaceutically acceptable salt thereof and one or more additional therapeutic agents, optionally together with one or more inert carriers and/or diluents.

Other aspects of the invention become apparent to the one skilled in the art from the specification and the experimental part as described hereinbefore and hereinafter.

DETAILED DESCRIPTION

Unless otherwise stated, the groups, residues, and substituents, particularly $R^1$, $R^2$ and $R^N$ are defined as above and hereinafter. If residues, substituents, or groups occur several times in a compound, they may have the same or different meanings. Some preferred meanings of individual groups and substituents of the compounds according to the invention will be given hereinafter. Any and each of these definitions may be combined with each other.

$R^1$:

$R^1$-G1:

The group $R^1$ is preferably selected from the group $R^1$-G1 as defined hereinbefore.

$R^1$-G2:

According to one embodiment the group $R^1$ is selected from the group $R^1$-G2 consisting of a monocyclic or bicyclic group having 5 to 10 ring member atoms of which 4 to 9 ring members are C atoms and 1 to 3 ring members are heteroatoms selected from N and $NR^N$, or 1 or 2 ring members are heteroatoms selected from N and $NR^N$ and 1 ring member is O or S, wherein the ring member atom attached to the —$CH_2$— group in formula I is a N atom, wherein 1 $CH_2$ ring member attached to a ring member N atom is optionally replaced by a —C(=O)— group, wherein the monocyclic or bicyclic group is saturated or partially unsaturated, with the proviso that in bicyclic groups the ring attached to the —$CH_2$— group in formula I must not be aromatic, and wherein the bicyclic group may be a fused, bridged or spiro ring system;

wherein any of these groups is optionally and independently substituted with 1, 2, or 3 $R^2$ groups;

$R^1$-G3:

According to one embodiment the group $R^1$ is selected from the group $R^1$-G3 consisting of

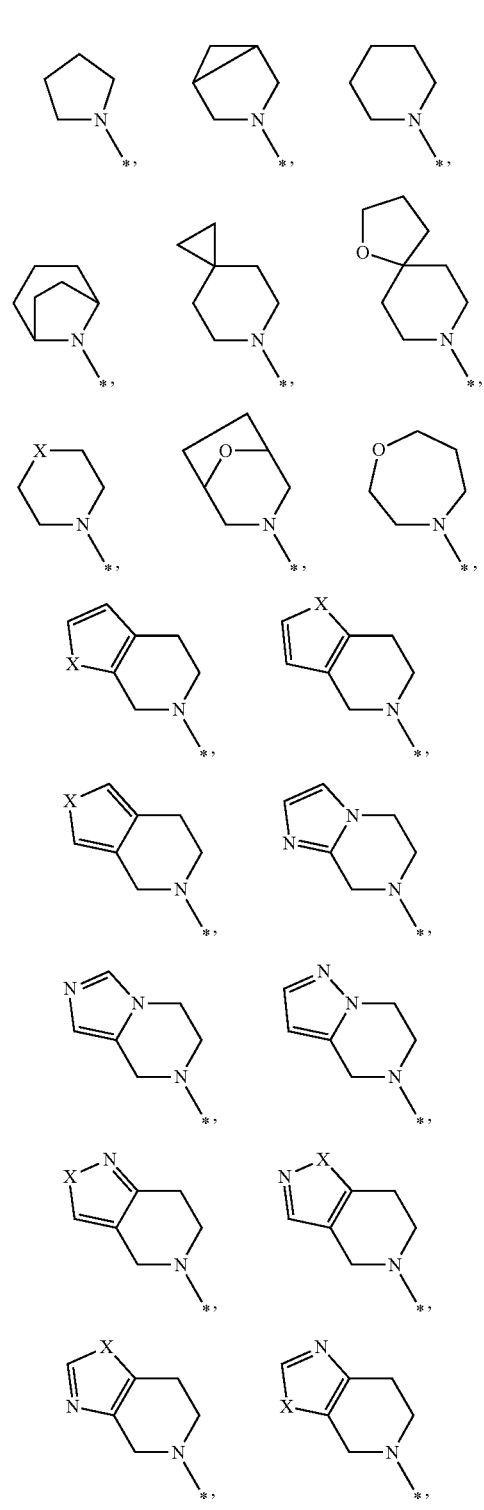

-continued

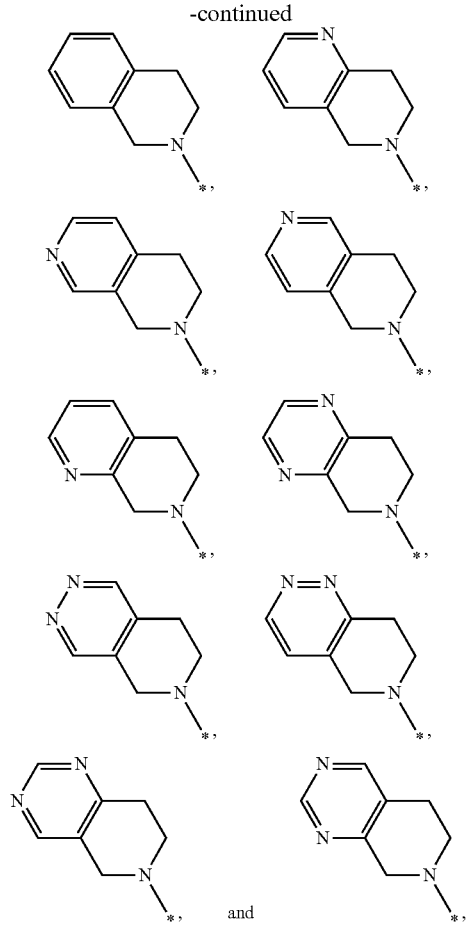

wherein X denotes NR$^N$, O, or S, and
wherein in any group 1 ring member CH$_2$ group adjacent to a ring member N atom is optionally replaced by a C(=O) group, and
wherein any group is optionally substituted with 1 to 3 groups independently selected from R$^2$.

R$^1$-G3a:
According to one embodiment the group R$^1$ is selected from the group R$^1$-G3a consisting of

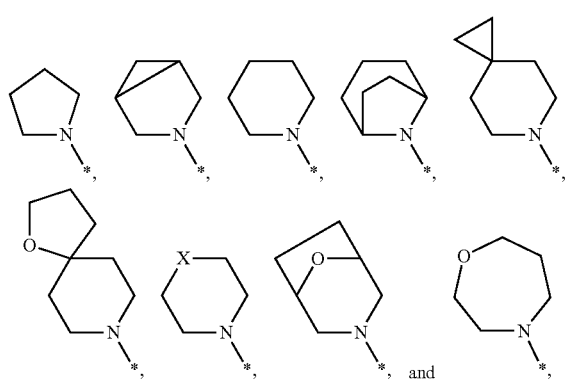

wherein X denotes NR$^N$, O, or S, and
wherein in any group 1 ring member CH$_2$ group adjacent to a ring member N atom is optionally replaced by C(=O), and wherein any group is optionally substituted with 1, 2, or 3 groups independently selected from R$^2$.

R$^1$-G3b:
According to one embodiment the group R$^1$ is selected from the group R$^1$-G3b consisting of

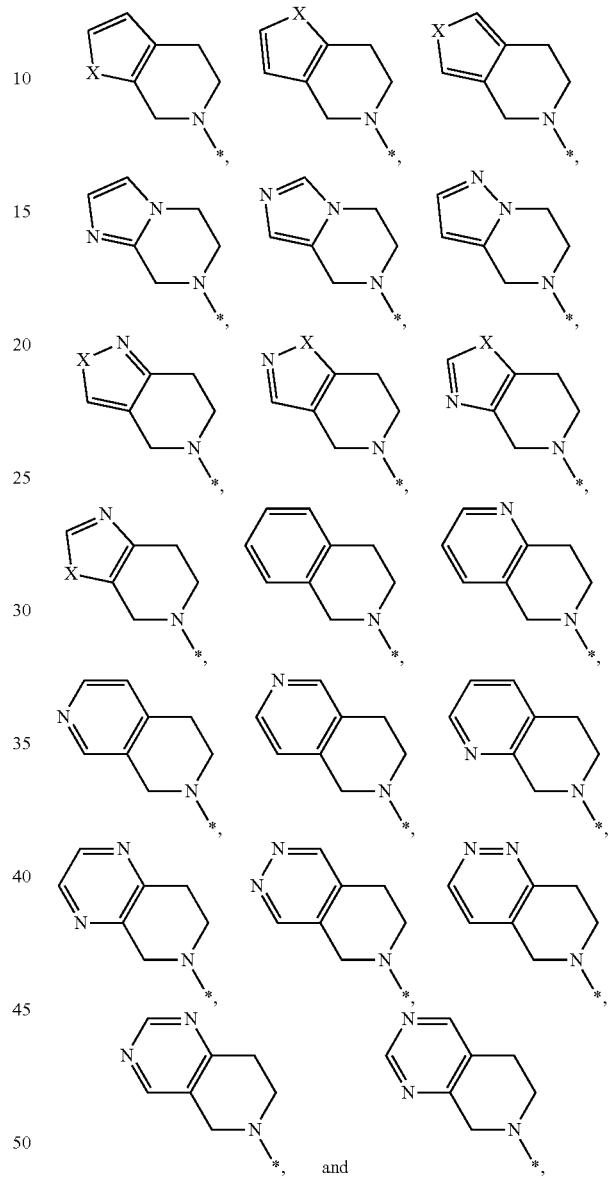

wherein X denotes NR$^N$, O, or S, and
wherein in any group 1 ring member CH$_2$ group adjacent to a ring member N atom is optionally replaced by C(=O), and wherein any group is optionally substituted with 1, 2, or 3 groups independently selected from R$^2$.

R$^1$-G4:
In another embodiment the group R$^1$ is selected from the group R$^1$-G4 consisting of a pyrrolidin-1-yl, 3-aza-bicyclo[3.1.0]hexan-3-yl, 8-aza-bicyclo[3.2.1]octan-8-yl, 6-aza-spiro[2.5]octan-6-yl, 1-oxa-8-aza-spiro[4.5]decan-8-yl, 8-oxa-3-aza-bicyclo[3.2.1]octan-3-yl, thiomorpholin-4-yl, and [1,4]oxazepan-4-yl ring;
a piperidin-1-yl ring, optionally substituted with 1 or 2 groups independently selected from F, H$_3$C—, HO—H$_2$C—, HO—, and H$_3$C—O—;

a piperazin-1-yl group, wherein the ring member N not attached to the —CH$_2$— group in formula I is substituted with R$^N$, and wherein 1 CH$_2$ ring member is optionally replaced by a —C(=O)— group;

a morpholin-4-yl ring, optionally substituted with 1 or 2 H$_3$C— groups; and a 4,5,6,7-tetrahydro-thieno[2,3-c]pyridin-6-yl, 5,6,7,8-tetrahydro-1H-imidazo[1,2-a]pyrazin-7-yl, 4,5,6,7-tetrahydropyrazolo[1,5-a]pyrazin-5-yl, 4,5,6,7-tetrahydro-2H-pyrazolo[4,3-c]pyridin-5-yl, 4,5,6,7-tetrahydro-oxazolo[4,5-c]pyridin-5-yl, 4,5,6,7-tetrahydro-isoxazolo[4,3-c]pyridin-5-yl, 4,5,6,7-tetrahydro-thiazolo[5,4-c]pyridin-5-yl, 1,2,3,4-tetrahydro-isoquinolin-2-yl, and 5,6,7,8-tetrahydro-[1,6]naphthyridin-6-yl ring, wherein each ring having a NH group is substituted with R$^N$ at this N, and each ring is optionally substituted with 1 H$_3$C— group.

R$^1$-G5:

In another embodiment the group R$^1$ is selected from the group R$^1$-G5 consisting of

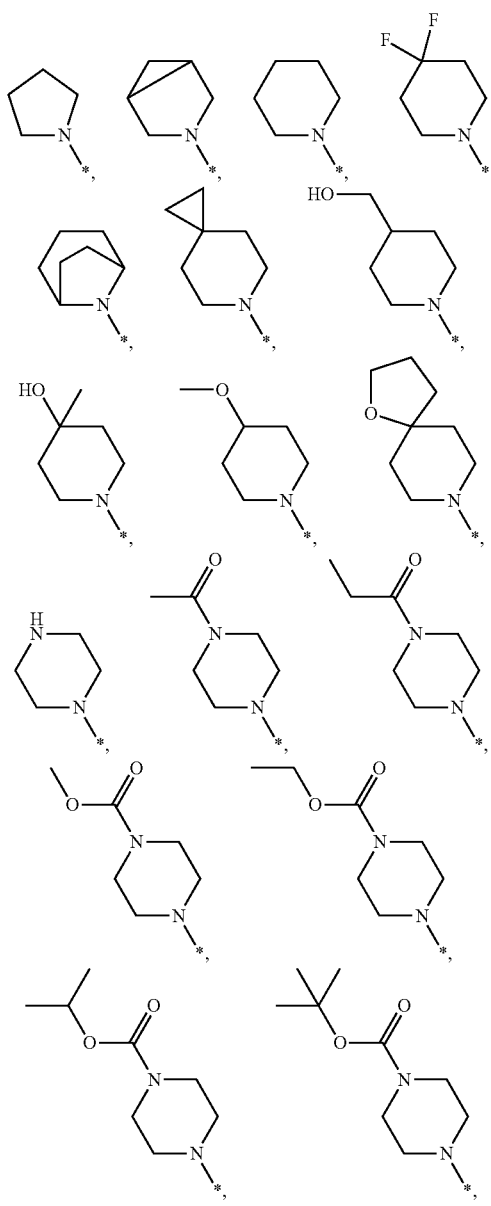

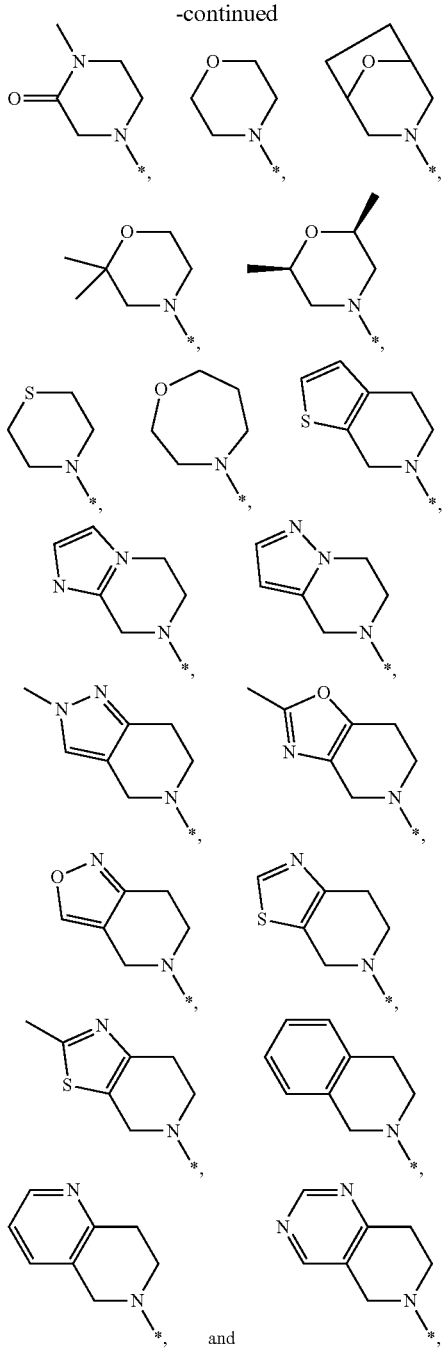

and

R$^2$:

R$^2$-G1:

The group R$^2$ is preferably selected from the group R$^2$-G1 as defined hereinbefore.

R$^2$-G2:

In another embodiment the group R$^2$ is selected from the group R$^2$-G2 consisting of F, Cl, C$_{1-3}$-alkyl, NC—, HO—C$_{1-3}$-alkyl, C$_{1-3}$-alkyl-O—C$_{1-3}$-alkyl, HO—, C$_{1-3}$-alkyl-O, H$_3$C—S(=O)—, H$_3$C—S(=O)$_2$—, C$_{3-6}$-cycloalkyl-, and C$_{3-6}$-cycloalkyl-O—, wherein any alkyl and cycloalkyl group or submoiety is optionally substituted with 1 to 3 F atoms.

R$^2$-G3:

In another embodiment the group R$^2$ is selected from the group R$^2$-G3 consisting of F, Cl, C$_{1-3}$-alkyl, F$_3$C—, NC—, HO—$C_{1-3}$-alkyl, $H_3C$—O—$C_{1-3}$-alkyl, HO—, $C_{1-3}$-alkyl-O, $F_2HC$—O—, $F_3C$—O—, $H_3C$—$S(=O)_2$—, $C_{3-6}$-cycloalkyl-, and $C_{3-6}$-cycloalkyl-O—.

$R^2$-G4:

In another embodiment the group $R^2$ is selected from the group $R^2$-G4 consisting of F, $C_{1-3}$-alkyl, $F_3C$—, HO—$CH_2$—, $H_3C$—O—$CH_2$—, NC—, HO—, $C_{1-3}$-alkyl-O—, and $H_3C$—$S(=O)_2$—.

$R^2$-G5:

In another embodiment the group $R^2$ is selected from the group $R^2$-G5 consisting of F, $H_3C$—, HO—$H_2C$—, HO—, and $H_3C$—O—.

$R^N$:

$R^N$-G1:

The group $R^N$ is preferably selected from the group $R^N$-G1 as defined hereinbefore.

$R^N$-G2:

In another embodiment the group $R^N$ is selected from the group $R^N$-G2 consisting of H, $H_3C$—, $H_3C$—$C(=O)$—, $H_3C$—$H_2C$—$C(=O)$—, and $C_{1-4}$-alkyl-O—$C(=O)$—.

Examples of preferred subgeneric embodiments (E) according to the present invention are set forth in the following table, wherein each substituent group of each embodiment is defined according to the definitions set forth hereinbefore and wherein all other substituents of the formula I are defined according to the definitions set forth hereinbefore:

| Embodiment | $R^1$— | $R^2$— | $R^N$— |
|---|---|---|---|
| E-1 | $R^1$—G1 | $R^2$—G1 | $R^N$—G1 |
| E-2 | $R^1$—G2 | $R^2$—G1 | $R^N$—G1 |
| E-3 | $R^1$—G3 | $R^2$—G1 | $R^N$—G1 |
| E-4 | $R^1$—G3 | $R^2$—G2 | $R^N$—G1 |
| E-5 | $R^1$—G3 | $R^2$—G2 | $R^N$—G2 |
| E-6 | $R^1$—G3 | $R^2$—G3 | $R^N$—G2 |
| E-7 | $R^1$—G3 | $R^2$—G4 | $R^N$—G2 |
| E-8 | $R^1$—G3 | $R^2$—G5 | $R^N$—G2 |
| E-9 | $R^1$—G4 | — | $R^N$—G2 |
| E-10 | $R^1$—G5 | — | — |

Preferred are those compounds of formula I, wherein $R^1$ is selected from the group consisting of

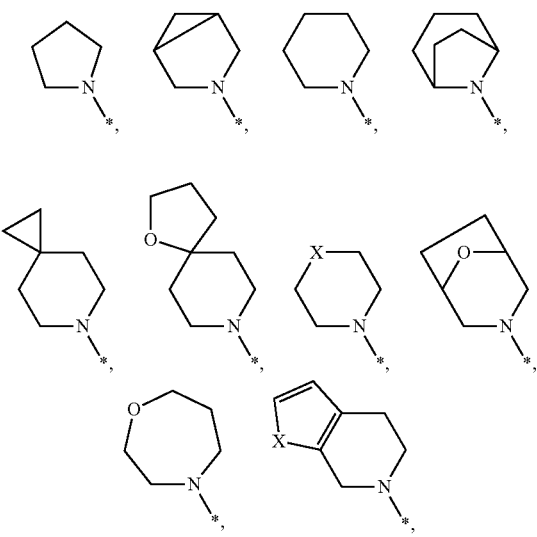

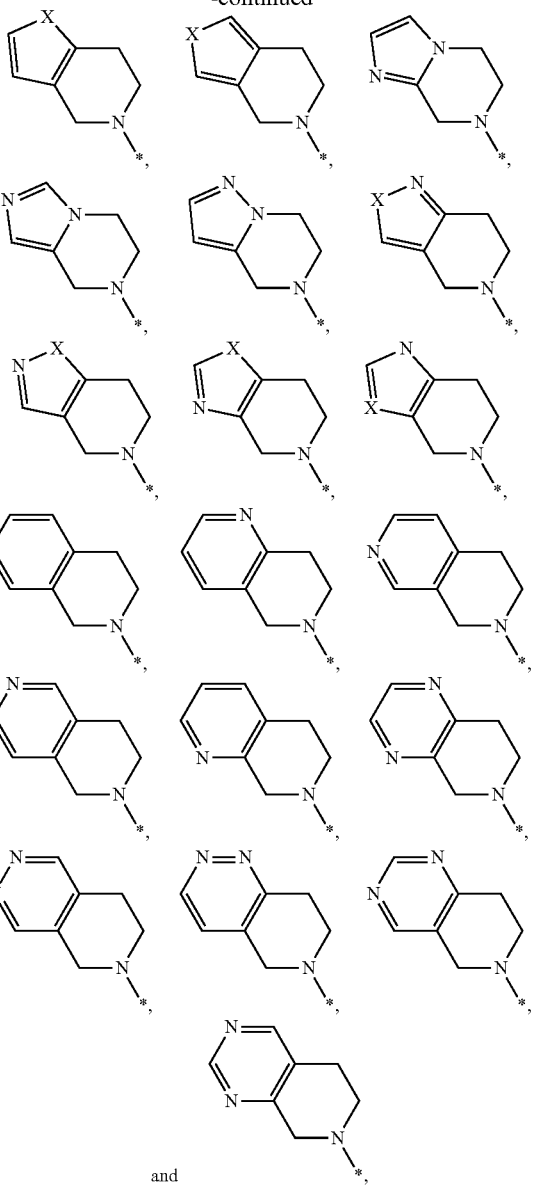

and wherein X denotes $NR^N$, O, or S, and wherein in any group 1 ring member $CH_2$ group adjacent to a ring member N atom is optionally replaced by a $C(=O)$ group, and wherein any group is optionally substituted with 1 to 3 groups independently selected from $R^2$;

$R^2$ is selected from the group consisting of F, Cl, $C_{1-3}$-alkyl, NC—, HO—$C_{1-3}$-alkyl, $C_{1-3}$-alkyl-O—$C_{1-3}$-alkyl, HO—, $C_{1-3}$-alkyl-O, $H_3C$—$S(=O)$—, $H_3C$—$S(=O)_2$—, $C_{3-6}$-cycloalkyl-, and $C_{3-6}$-cycloalkyl-O—, wherein any alkyl and cycloalkyl group or submoiety is optionally substituted with 1 to 3 F atoms; and $R^N$ is selected from the group consisting of H, $C_{1-4}$-alkyl-, $C_{1-4}$-alkyl-C(O)— and $C_{1-4}$-alkyl-O—C(O)—;

and the pharmaceutically acceptable salts thereof.

Particularly preferred compounds, including their tautomers and stereoisomers, the salts thereof, or any solvates or hydrates thereof, are described in the experimental section hereinafter.

The compounds according to the invention and their intermediates may be obtained using methods of synthesis which are known to the one skilled in the art and described in the literature of organic synthesis. Preferably the compounds are obtained analogously to the methods of preparation explained more fully hereinafter, in particular as described in the experimental section. In some cases the sequence adopted in carrying out the reaction schemes may be varied. Variants of these reactions that are known to the skilled man but are not described in detail here may also be used. The general processes for preparing the compounds according to the invention will become apparent to the skilled man on studying the schemes that follow. Starting compounds are commercially available or may be prepared by methods that are described in the literature or herein, or may be prepared in an analogous or similar manner. Before the reaction is carried out any corresponding functional groups in the compounds may be protected using conventional protecting groups. These protecting groups may be cleaved again at a suitable stage within the reaction sequence using methods familiar to the skilled man.

The compounds of the invention I are preferably accessed from a precursor 1 that bears the carboxylic acid protected as ester (Scheme 1); $R^1$ has the meaning as defined hereinbefore and hereinafter. The ester group may be hydrolysed in the presence of an acid, such as hydrochloric acid or sulfuric acid, or an alkali metal hydroxide, such as lithium hydroxide, sodium hydroxide, or potassium hydroxide, to yield the carboxylic acid. The hydrolysis is preferably conducted in aqueous solvents, such as water combined with tetrahydrofuran, 1,4-dioxane, alcohol, e.g. methanol, ethanol and isopropanol, or dimethyl sulfoxide, at 0 to 120° C. A tert-butyl ester is preferably cleaved under acidic conditions, e.g. trifluoroacetic acid or hydrochloric acid, in a solvent, such as dichloromethane, 1,4-dioxane, isopropanol or ethyl acetate. A benzyl ester is advantageously cleaved using hydrogen in the presence of a transition metal, preferably palladium on carbon. Benzyl esters bearing electron donating groups on the phenyl ring, such as methoxy, may also be removed under oxidative conditions; ceric ammonium nitrate (CAN) or 2,3-dichloro-5,6-dicyanoquinone (DDQ) are two commonly used reagents for this approach.

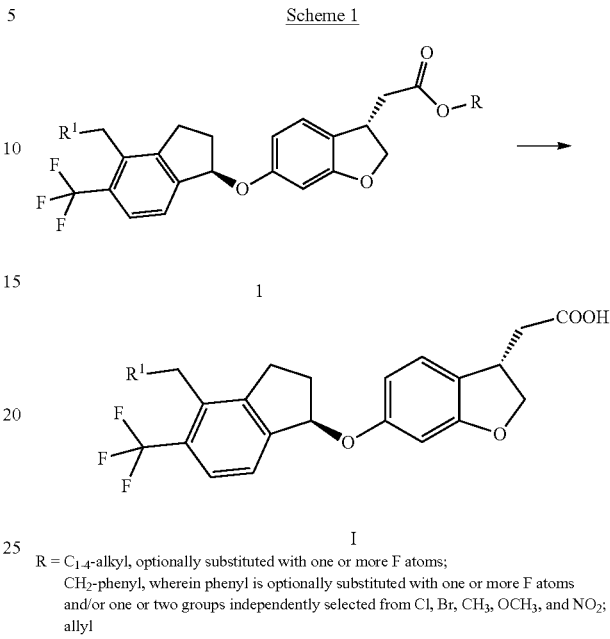

Scheme 1

$R = C_{1-4}$-alkyl, optionally substituted with one or more F atoms;
$CH_2$-phenyl, wherein phenyl is optionally substituted with one or more F atoms and/or one or two groups independently selected from Cl, Br, $CH_3$, $OCH_3$, and $NO_2$;
allyl Compound 1 may be assembled using building blocks 2, 3 and 4 (Scheme 2); $R^1$ has the meaning as defined hereinbefore and hereinafter.

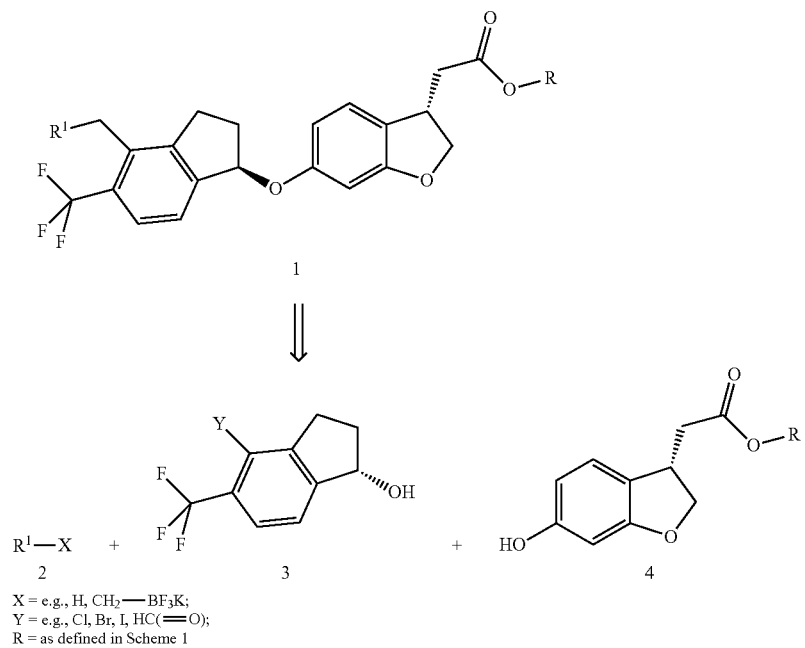

Scheme 2

X = e.g., H, $CH_2$—$BF_3K$;
Y = e.g., Cl, Br, I, HC(=O);
R = as defined in Scheme 1

Building blocks 3 and 4 may be combined in a stereoselective fashion employing the conditions of the Mitsunobu reaction or variations thereof (Scheme 3); $R^1$ has the meaning as defined hereinbefore and hereinafter. The reaction is usually conducted with a phosphine and an azodicarboxylic ester or amide in tetrahydrofuran, 1,4-dioxane, diethyl ether, toluene, benzene, dichloromethane, or mixtures thereof, at −30 to 100° C. Phosphines often used are triphenylphosphine and tributylphosphine, which are commonly combined with dimethyl azodicarboxylate, diethyl azodicarboxylate, diisopropyl azodicarboxylate, di-(4-chlorobenzyl) azodicarboxylate, dibenzyl azodicarboxylate, di-tert-butyl azodicarboxylate, azodicarboxylic acid bis-(dimethylamide), azodicarboxylic acid dipiperidide, or azodicarboxylic acid dimorpholide.

$CH_2$ unit to be coupled (Scheme 4, c)). The nucleophilic substitution of the leaving group, e.g. Cl, Br or I, with the secondary amine is preferably conducted in the presence of a base, e.g. potassium carbonate, in a solvent, e.g. N,N-dimethylformamide, at 0 to 100° C.

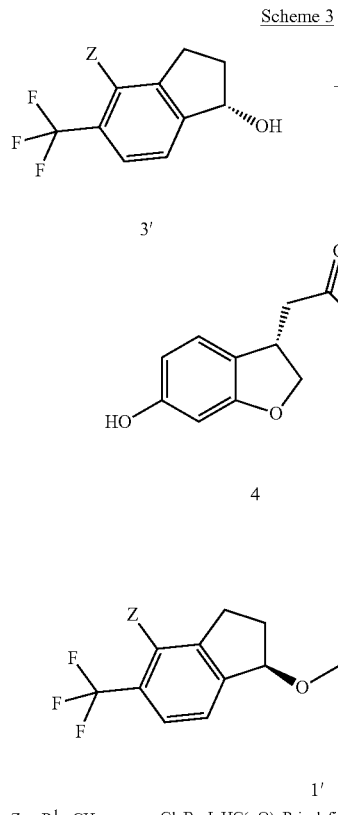

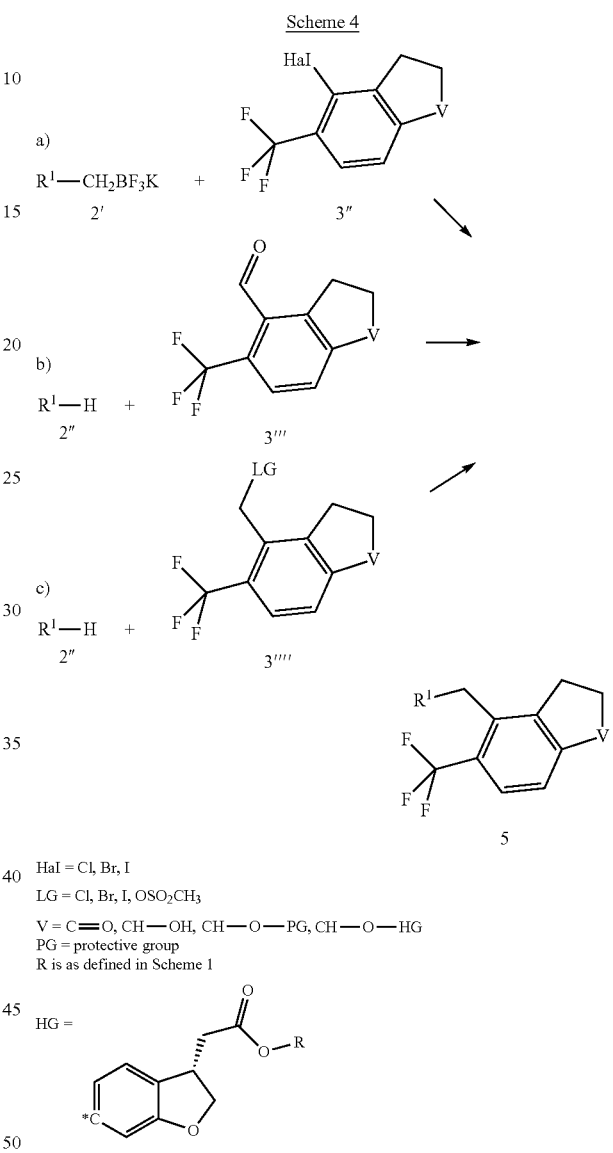

The group $R^1$ may be attached to the indane moiety via a $CH_2$ group starting from various precursors (Scheme 4); $R^1$ has the meaning as defined hereinbefore and hereinafter.

Transition metal catalyzed coupling of the indane part (3″) as electrophile, bearing a chlorine, bromine or iodine at the carbon atom to be coupled, and $R^1$—$CH_2$—$BF_3K$ (2′) as nucleophile is a preferred proceeding (Scheme 4, a)). The reaction is preferably conducted with a palladium derived catalyst, e.g. palladium acetate combined with 2-dicyclohexylphosphino-2′,4′,6′-triisopropyl-1,1′-biphenyl (X-Phos), in the presence of a base, e.g. cesium carbonate, in a mixture of water and tetrahydrofuran at 40 to 100° C.

Employing $R^1$ as a secondary amine, $R^1$—H (2″), and the indane part decorated with a formyl group (3‴) may link the two moieties upon reductive amination (Scheme 4, b)). The reaction is carried out with a reducing agent, e.g. sodium cyanoborohydride ($NaH_3BCN$), sodium triacetoxyborohydride ($NaHB(O_2CCH_3)_3$) or sodium borohydride ($NaBH_4$), optionally in the presence of an acid, e.g. acetic acid, in a solvent, e.g. 1,2-dichloroethane, at 0 to 60° C.

$R^1$ as a secondary amine, $R^1$—H (2″), may also be combined with the indane part (3″″) bearing a leaving group at the Intermediate 3 or derivatives thereof, as 3″″, may be obtained from indanone 7, which, in turn, may be prepared from phenylpropionic acid derivative 6 (Scheme 5). For the intramolecular acylation (Friedel-Crafts acylation), 6→7, a considerable number of approaches has been reported. The reaction may be performed starting with a carboxylic acid, carboxylic ester, carboxylic anhydride, carboxylic chloride or fluoride, or a nitrile using a Lewis acid as catalyst. The following Lewis acids are some of the more often used ones: hydrobromic acid, hydroiodic acid, hydrochloric acid, sulfuric acid, phosphoric acid, $P_4O_{10}$, trifluoroacetic acid, methanesulfonic acid, toluenesulfonic acid, trifluoromethanesulfonic acid, $ClSO_3H$, $Sc(OSO_2CF_3)_3$, $Tb(OSO_2CF_3)_3$, $SnCl_4$, $FeCl_3$, $AlBr_3$, $AlCl_3$, $SbCl_5$, $BCl_3$, $BF_3$, $ZnCl_2$, montmorillonites, $POCl_3$, and $PCl_5$. The reaction may be conducted, e.g., in dichloromethane, 1,2-dichloroethane, nitrobenzene, chlorobenzene, carbon disulfide, mixtures thereof, or without an additional solvent in an excess of the Lewis acid, at 0 to 180° C. Carboxylic acids are preferably reacted in polyphosphoric acid at 0 to 120° C., while carboxylic chlorides are preferably reacted with $AlCl_3$ in dichloromethane or 1,2-dichloroethane at 0 to 80° C.

The subsequent reduction of the keto group in compound 7 providing the alcohol 3"" in enantiomerically enriched or pure form may be accomplished using hydrogen or a hydrogen source, such as formate or silane, and a transition metal catalyst derived from, e.g., Ir, Rh, Ru or Fe and a chiral auxiliary. For instance, a ruthenium complex, such as chloro{[(1S,2S)-(−)-2-amino-1,2-diphenylethyl](4-toluenesulfonyl)-amido}-(mesitylene)ruthenium(II), may deliver the hydroxy compound 3"" with high enantiomeric excess using, e.g., formic acid in the presence of a base, e.g. triethylamine, in dichloromethane, at −20 to 60° C. Alternatively, boranes combined with an enantiomerically pure [1,3,2]oxazaborol may be used as reducing agent (Corey-Bakshi-Shibata reaction or Corey-Itsuno reaction). Borane (complexed with, e.g., dimethyl sulfide) and (R)- or (S)-3,3-diphenyl-1-methyltetrahydro-1H,3H-pyrrolo[1,2-c][1,3,2]oxazaborol in, e.g. dichloromethane, toluene, methanol, tetrahydrofuran, or mixtures thereof, at 0 to 60° C., are typical reaction conditions used for this approach.

Scheme 5

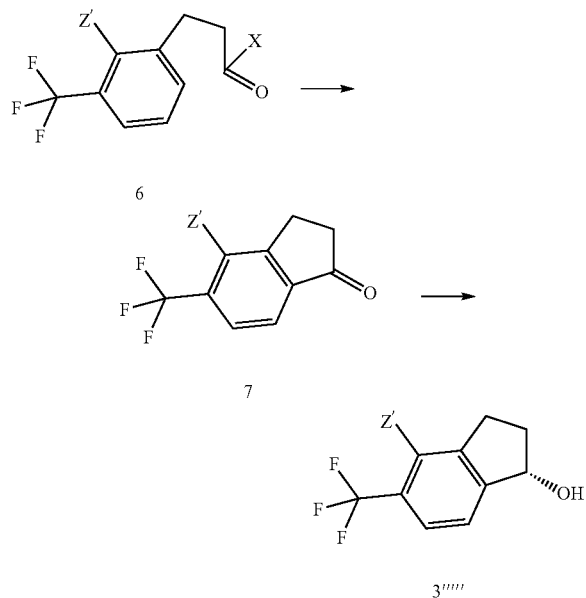

Z' = e.g., Cl, Br, I

The synthetic routes presented may rely on the use of protecting groups. For example, potentially reactive groups present, such as hydroxy, carbonyl, carboxy, amino, alkylamino, or imino, may be protected during the reaction by conventional protecting groups which are cleaved again after the reaction. Suitable protecting groups for the respective functionalities and their removal are well known to the one skilled in the art and are described in the literature of organic synthesis.

The compounds of general formula I may be resolved into their enantiomers and/or diastereomers as mentioned below. Thus, for example, cis/trans mixtures may be resolved into their cis and trans isomers and racemic compounds may be separated into their enantiomers.

The cis/trans mixtures may be resolved, for example, by chromatography into the cis and trans isomers thereof. The compounds of general formula I which occur as racemates may be separated by methods known per se into their optical antipodes and diastereomeric mixtures of compounds of general formula I may be resolved into their diastereomers by taking advantage of their different physico-chemical properties using methods known per se, e.g. chromatography and/or fractional crystallization; if the compounds obtained thereafter are racemates, they may be resolved into the enantiomers as mentioned below.

The racemates are preferably resolved by column chromatography on chiral phases or by crystallization from an optically active solvent or by reacting with an optically active substance which forms salts or derivatives such as esters or amides with the racemic compound. Salts may be formed with enantiomerically pure acids for basic compounds and with enantiomerically pure bases for acidic compounds. Diastereomeric derivatives are formed with enantiomerically pure auxiliary compounds, e.g. acids, their activated derivatives, or alcohols. Separation of the diastereomeric mixture of salts or derivatives thus obtained may be achieved by taking advantage of their different physico-chemical properties, e.g. differences in solubility; the free antipodes may be released from the pure diastereomeric salts or derivatives by the action of suitable agents. Optically active acids commonly used for such a purpose as well as optically active alcohols applicable as auxiliary residues are known to those skilled in the art.

As mentioned above, the compounds of formula I may be converted into salts, particularly for pharmaceutical use into the pharmaceutically acceptable salts. As used herein, "pharmaceutically acceptable salts" refer to derivatives of the disclosed compounds wherein the parent compound is modified by making acid or base salts thereof.

The compounds according to the invention are advantageously also obtainable using the methods described in the examples that follow, which may also be combined for this purpose with methods known to the skilled man from the literature.

TERMS AND DEFINITIONS

Terms not specifically defined herein should be given the meanings that would be given to them by one of skill in the art in light of the disclosure and the context. As used in the specification, however, unless specified to the contrary, the following terms have the meaning indicated and the following conventions are adhered to.

The terms "compound(s) according to this invention", "compound(s) of formula (I)", "compound(s) of the invention" and the like denote the compounds of the formula (I) according to the present invention including their tautomers, stereoisomers and mixtures thereof and the salts thereof, in particular the pharmaceutically acceptable salts thereof, and the solvates and hydrates of such compounds, including the solvates and hydrates of such tautomers, stereoisomers and salts thereof.

The terms "treatment" and "treating" embrace both preventative, i.e. prophylactic, or therapeutic, i.e. curative and/or palliative, treatment. Thus the terms "treatment" and "treating" comprise therapeutic treatment of patients having already developed said condition, in particular in manifest form. Therapeutic treatment may be symptomatic treatment in order to relieve the symptoms of the specific indication or causal treatment in order to reverse or partially reverse the conditions of the indication or to stop or slow down progression of the disease. Thus the compositions and methods of the present invention may be used for instance as therapeutic treatment over a period of time as well as for chronic therapy. In addition the terms "treatment" and "treating" comprise prophylactic treatment, i.e. a treatment of patients at risk to develop a condition mentioned hereinbefore, thus reducing said risk.

When this invention refers to patients requiring treatment, it relates primarily to treatment in mammals, in particular humans.

The term "therapeutically effective amount" means an amount of a compound of the present invention that (i) treats or prevents the particular disease or condition, (ii) attenuates, ameliorates, or eliminates one or more symptoms of the particular disease or condition, or (iii) prevents or delays the onset of one or more symptoms of the particular disease or condition described herein.

The terms "modulated" or "modulating", or "modulate(s)", as used herein, unless otherwise indicated, refer to the activation of the G-protein-coupled receptor GPR40 with one or more compounds of the present invention.

The terms "mediated" or "mediating" or "mediate", as used herein, unless otherwise indicated, refer to the (i) treatment, including prevention of the particular disease or condition, (ii) attenuation, amelioration, or elimination of one or more symptoms of the particular disease or condition, or (iii) prevention or delay of the onset of one or more symptoms of the particular disease or condition described herein.

The term "substituted" as used herein, means that any one or more hydrogens on the designated atom, radical or moiety is replaced with a selection from the indicated group, provided that the atom's normal valence is not exceeded, and that the substitution results in an acceptably stable compound.

In the groups, radicals, or moieties defined below, the number of carbon atoms is often specified preceding the group, for example, $C_{1-6}$-alkyl means an alkyl group or radical having 1 to 6 carbon atoms. In general, for groups comprising two or more subgroups, the last named subgroup is the radical attachment point, for example, the substituent "aryl-$C_{1-3}$-alkyl-" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail.

An asterisk may be used in sub-formulas to indicate the bond which is connected to the core molecule as defined.

The numeration of the atoms of a substituent starts with the atom which is closest to the core or to the group to which the substituent is attached.

For example, the term "3-carboxypropyl-group" represents the following substituent:

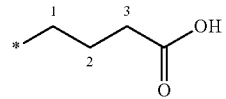

wherein the carboxy group is attached to the third carbon atom of the propyl group. The terms "1-methylpropyl-", "2,2-dimethylpropyl-" or "cyclopropylmethyl-" group represent the following groups:

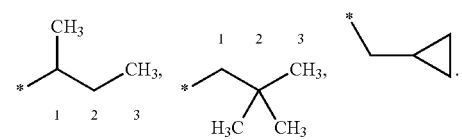

The asterisk may be used in sub-formulas to indicate the bond which is connected to the core molecule as defined.

In a definition of a group the term "wherein each X, Y and Z group is optionally substituted with" and the like denotes that each group X, each group Y and each group Z either each as a separate group or each as part of a composed group may be substituted as defined. For example a definition "$R^{ex}$ denotes H, $C_{1-3}$-alkyl, $C_{3-6}$-cycloalkyl, $C_{3-6}$-cycloalkyl-$C_{1-3}$-alkyl or $C_{1-3}$-alkyl-O—, wherein each alkyl group is optionally substituted with one or more $L^{ex}$." or the like means that in each of the beforementioned groups which comprise the term alkyl, i.e. in each of the groups $C_{1-3}$-alkyl, $C_{3-6}$-cycloalkyl-$C_{1-3}$-alkyl and $C_{1-3}$-alkyl-O—, the alkyl moiety may be substituted with $L^{ex}$ as defined.

Unless specifically indicated, throughout the specification and the appended claims, a given chemical formula or name shall encompass tautomers and all stereo, optical and geometrical isomers (e.g. enantiomers, diastereomers, E/Z isomers etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof.

Salts of other acids than those mentioned above which for example are useful for purifying or isolating the compounds of the present invention (e.g. trifluoro acetate salts) also comprise a part of the invention.

The term halogen generally denotes fluorine, chlorine, bromine and iodine.

The term "$C_{1-n}$-alkyl", wherein n is an integer from 1 to n, either alone or in combination with another radical denotes an acyclic, saturated, branched or linear hydrocarbon radical with 1 to n C atoms. For example the term $C_{1-5}$-alkyl embraces the radicals $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$.

The term "$C_{3-n}$-carbocyclyl" as used either alone or in combination with another radical, denotes a monocyclic, bicyclic or tricyclic, saturated or unsaturated hydrocarbon radical with 3 to n C atoms. The hydrocarbon radical is preferably nonaromatic. Preferably the 3 to n C atoms form one or two rings. In case of a bicyclic or tricyclic ring system the rings may be attached to each other via a single bond or may be fused or may form a spirocyclic or bridged ring system. For example the term $C_{3-10}$-carbocyclyl includes $C_{3-10}$-cycloalkyl, $C_{3-10}$-cycloalkenyl, octahydropentalenyl, octahydroindenyl, decahydronaphthyl, indanyl, tetrahydronaphthyl. Most preferably the term $C_{3-n}$-carbocyclyl denotes $C_{3-n}$-cycloalkyl, in particular $C_{3-7}$-cycloalkyl.

The term "$C_{3-n}$-cycloalkyl", wherein n is an integer 4 to n, either alone or in combination with another radical denotes a cyclic, saturated, unbranched hydrocarbon radical with 3 to n C atoms. The cyclic group may be mono-, bi-, tri- or spirocyclic, most preferably monocyclic. Examples of such cycloalkyl groups include cyclopropyl, cyclobutyl, cyclopentyl, cyclohexyl, cycloheptyl, cyclooctyl, cyclononyl, cyclododecyl, bicyclo[3.2.1]octyl, spiro[4.5]decyl, norpinyl, norbonyl, norcaryl, adamantyl, etc.

Many of the terms given above may be used repeatedly in the definition of a formula or group and in each case have one of the meanings given above, independently of one another.

Chemical Stability

Degradation kinetics is used to simulate chemical stability of compounds in the acidic part of the gastro intestinal tract. The compounds of the invention show superior chemical stability in acidic aqueous media (pH value ca. 1.2) compared to the bulk of compounds explicitly disclosed in WO 2012072691. Their application as medical drugs to treat human diseases is therefore less restricted and troublesome.

The chemical stability of the compounds of the invention at pH value of ca. 1.2 is determined as follows:

Compound is dissolved in an HPLC vial either in a mixture of acetonitrile/0.1 M aqueous HCl (2:3; pH ca. 1.2) or in a mixture of acetonitrile/McIlvaine buffer pH 7.4 (2:3) to get a concentration of approximately 0.25 mg/ml. The vial was then transferred into an HPLC autosampler system and maintained at a temperature of 37° C. A first sample is taken and injected immediately into a standard HPLC system with a UV DAD detector. Further samples are injected after 2, 4, 6, 8 and 10 hours. Degradation of the compound is measured by determining the recovery rate of compound [%] for each injection using an HPLC standard gradient method. Therefore the peak area of the main peak for the first injection ($AU_{t0}$) is determined and set as 100%. Peak area of the main peak is determined also for the further injections ($AU_{tn}$, n=2, 4, 6, 8, 10) and expressed as fraction of ($AU_{t0}$)/($AU_{tn}$, n=2, 4, 6, 8, 10) [%].

The recovery rate of the compounds according to the invention after 2 h at pH value of ca. 1.2 determined as described above is typically above 95%, preferably above 98%.

The following table compares the recovery rate after 2 h at pH value of ca. 1.2 of compounds according to the invention and compounds of WO 2012072691.

| Example in this invention | Recovery rate after 2 h | Example in WO 2012072691 | Recovery rate after 2 h |
| --- | --- | --- | --- |
| 1 | >99% | 2 | 88% |
| 6 | >99% | 25 | 98% |
|   |   | 29 | 1% |
|   |   | 32 | 2% |
|   |   | 37 | 95% |
|   |   | 42 | 0% |
|   |   | 43 | 0% |
|   |   | 60 | 74% |
|   |   | 64 | 82% |
|   |   | 68 | 82% |
|   |   | 84 | 81% |

Chemical structures of the examples of case WO 2012072691 listed in the table above:

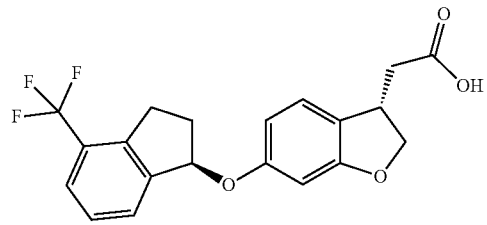

Example 2

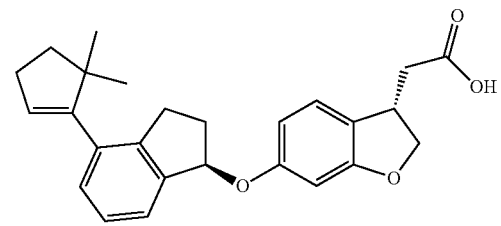

Example 42

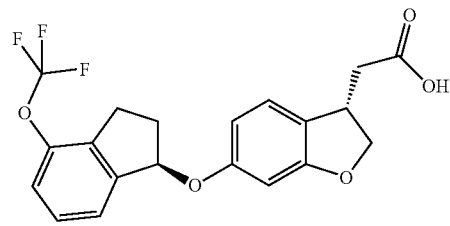

Example 25

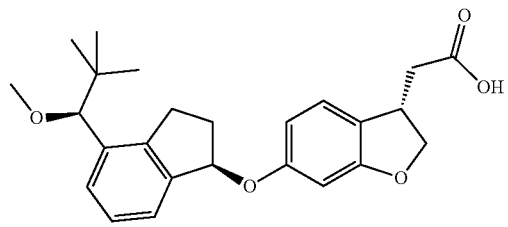

Example 29

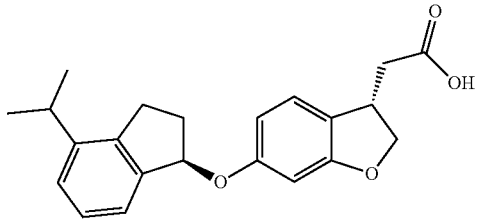

Example 32

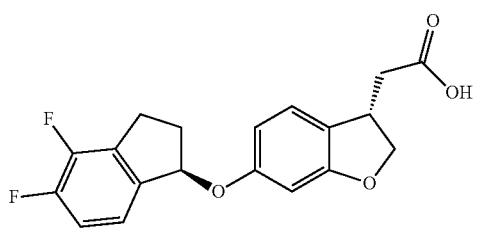

Example 37

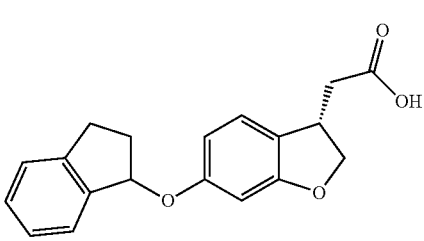

Example 43

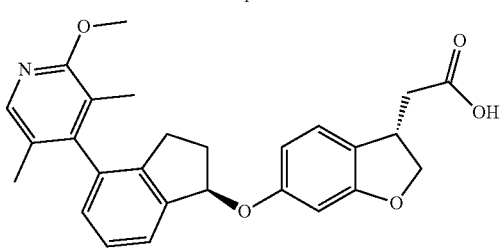

Example 60

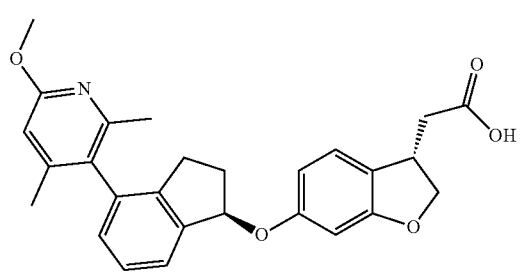

Example 64

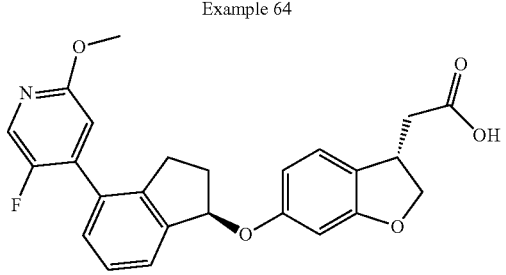

Example 68

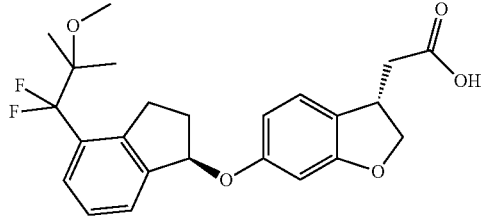

Example 84

Pharmacological Activity

The activity of the compounds of the invention may be demonstrated using the following assay:

$IP_1$ accumulation measurements using the IPOne assay system—1321N1 cells stably expressing human GPR40 receptor (Euroscreen, Belgium) are seeded 24 h before the assay in white 384-well plates in culture medium containing 10% FCS, 1% Na-Pyruvate and 400 μg/mL G418. $IP_1$ is assayed according to the manufacturer's description (Cisbio Bioassays, France). In brief, the assay is started by substitution of the culture medium by stimulation buffer (Hepes 10 mM, $CaCl_2$ 1 mM, $MgCl_2$ 0.5 mM, KCl 4.2 mM, NaCl 146 mM, glucose 5.5 mM and LiCl 50 mM, pH 7.4). Cells are stimulated for 1 h at 37° C., 5% $CO_2$ by addition of the compounds that are diluted in stimulation buffer containing LiCl. Assays are stopped by adding HTRF-conjugates (IP1-d2 and Anti-IP1 cryptate Tb) and lysis buffer, provided by the manufacturer. After an incubation time of 1 h at room temperature plates are measured using an EnVision™, Perkin Elmer. The obtained fluorescence ratios at 665/615 nM are then used to calculate the $pEC_{50}$ values using Assay Explorer 3.3 Software (Accelrys, Inc.) by interpolation using an $IP_1$ reference curve and subsequent sigmoidal curve fitting allowing for a variable hill slope.

The compounds according to the invention typically have $EC_{50}$ values in the range from about 1 nM to about 10 μM, preferably less than 1 μM, more preferably less than 100 nM.

$EC_{50}$ values for compounds according to the invention are shown in the following table. The number of the compound corresponds to the number of the Example in the experimental section.

| Example | $EC_{50}$ [nM] | Example | $EC_{50}$ [nM] | Example | $EC_{50}$ [nM] | Example | $EC_{50}$ [nM] |
|---|---|---|---|---|---|---|---|
| 1 | 3 | 2 | 20 | 3 | 3 | 4 | 92 |
| 5 | 5 | 6 | 2 | 7 | 3 | 8 | 5 |
| 9 | 3 | 10 | 5 | 11 | 6 | 12 | 20 |
| 13 | 9 | 14 | 15 | 15 | 468 | 16 | 16 |
| 17 | 4 | 18 | 11 | 19 | 7 | 20 | 9 |
| 21 | 12 | 22 | 14 | 23 | 7 | 24 | 14 |
| 25 | 15 | 26 | 26 | 27 | 17 | 28 | 4 |
| 29 | 3 | 30 | 3 | 31 | 2 | 32 | 2 |
| 33 | 2 | 34 | 3 | 35 | 3 | | |

In view of their ability to modulate the activity of the G-protein-coupled receptor GPR40, in particular an agonistic activity, the compounds of general formula I according to the invention, including the corresponding salts thereof, are theoretically suitable for the treatment of all those diseases or conditions which may be affected or which are mediated by the activation of the G-protein-coupled receptor GPR40.

Accordingly, the present invention relates to a compound of general formula I as a medicament.

Furthermore, the present invention relates to the use of a compound of general formula I or a pharmaceutical composition according to this invention for the treatment and/or prevention of diseases or conditions which are mediated by the activation of the G-protein-coupled receptor GPR40 in a patient, preferably in a human.

In yet another aspect the present invention relates to a method for treating a disease or condition mediated by the activation of the G-protein-coupled receptor GPR40 in a mammal that includes the step of administering to a patient, preferably a human, in need of such treatment a therapeutically effective amount of a compound or a pharmaceutical composition of the present invention.

Diseases and conditions mediated by agonists of the G-protein-coupled receptor GPR40 embrace metabolic diseases or conditions. According to one aspect the compounds and pharmaceutical compositions of the present invention are particularly suitable for treating diabetes mellitus, in particular Type 2 diabetes, Type 1 diabetes, complications of diabetes (such as e.g. retinopathy, nephropathy or neuropathies, diabetic foot, ulcers or macroangiopathies), metabolic acidosis or ketosis, reactive hypoglycaemia, hyperinsulinaemia, glucose metabolic disorder, insulin resistance, metabolic syndrome, dyslipidaemias of different origins, atherosclerosis and related diseases, obesity, high blood pressure, chronic heart failure, oedema and hyperuricaemia.

The compounds and pharmaceutical compositions of the present invention are also suitable for preventing beta-cell degeneration such as e.g. apoptosis or necrosis of pancreatic beta cells. The compounds and pharmaceutical compositions of the present invention are also suitable for improving or restoring the functionality of pancreatic cells, and also for increasing the number and size of pancreatic beta cells.

Therefore according to another aspect the invention relates to compounds of formula I and pharmaceutical compositions according to the invention for use in preventing, delaying, slowing the progression of and/or treating metabolic diseases, particularly in improving the glycaemic control and/or beta cell function in the patient.

In another aspect the invention relates to compounds of formula I and pharmaceutical compositions according to the invention for use in preventing, delaying, slowing the progression of and/or treating type 2 diabetes, overweight, obesity, complications of diabetes and associated pathological conditions.

In addition the compounds and pharmaceutical compositions according to the invention are suitable for use in one or more of the following therapeutic processes:

for preventing, delaying, slowing the progression of or treating metabolic diseases, such as for example type 1 diabetes, type 2 diabetes, insufficient glucose tolerance, insulin resistance, hyperglycaemia, hyperlipidaemia, hypercholesterolaemia, dyslipidaemia, syndrome X, metabolic syndrome, obesity, high blood pressure, chronic systemic inflammation, retinopathy, neuropathy, nephropathy, atherosclerosis, endothelial dysfunction or bone-related diseases (such as osteoporosis, rheumatoid arthritis or osteoarthritis);

for improving glycaemic control and/or reducing fasting plasma glucose, postprandial plasma glucose and/or the glycosylated haemoglobin HbA1c;

for preventing, delaying, slowing or reversing the progression of disrupted glucose tolerance, insulin resistance and/or metabolic syndrome to type 2 diabetes;

for preventing, delaying, slowing the progression of or treating a condition or a disease selected from among the complications of diabetes, such as for example retinopathy, nephropathy or neuropathies, diabetic foot, ulcers or macroangiopathies;

for reducing weight or preventing weight gain or assisting weight loss;

for preventing or treating the degradation of pancreatic beta cells and/or improving and/or restoring the functionality of pancreatic beta cells and/or restoring the functionality of pancreatic insulin secretion;

for maintaining and/or improving insulin sensitivity and/or preventing or treating hyperinsulinaemia and/or insulin resistance.

In particular, the compounds and pharmaceutical compositions according to the invention are suitable for the treatment of obesity, diabetes (comprising type 1 and type 2 diabetes, preferably type 2 diabetes mellitus) and/or complications of diabetes (such as for example retinopathy, nephropathy or neuropathies, diabetic foot, ulcers or macroangiopathies).

The compounds according to the invention are most particularly suitable for treating type 2 diabetes mellitus.

The dose range of the compounds of general formula I applicable per day is usually from 0.001 to 10 mg per kg body weight, for example from 0.01 to 8 mg per kg body weight of the patient. Each dosage unit may conveniently contain from 0.1 to 1000 mg, for example 0.5 to 500 mg.

The actual therapeutically effective amount or therapeutic dosage will of course depend on factors known by those skilled in the art such as age and weight of the patient, route of administration and severity of disease. In any case the compound or composition will be administered at dosages and in a manner which allows a therapeutically effective amount to be delivered based upon patient's unique condition.

The compounds, compositions, including any combinations with one or more additional therapeutic agents, according to the invention may be administered by oral, transdermal, inhalative, parenteral or sublingual route. Of the possible methods of administration, oral or intravenous administration is preferred.

Pharmaceutical Compositions

Suitable preparations for administering the compounds of formula I, optionally in combination with one or more further therapeutic agents, will be apparent to those with ordinary skill in the art and include for example tablets, pills, capsules, suppositories, lozenges, troches, solutions, syrups, elixirs, sachets, injectables, inhalatives and powders etc. Oral formulations, particularly solid forms such as e.g. tablets or capsules are preferred. The content of the pharmaceutically active compound(s) is advantageously in the range from 0.1 to 90 wt.-%, for example from 1 to 70 wt.-% of the composition as a whole.

Suitable tablets may be obtained, for example, by mixing one or more compounds according to formula I with known excipients, for example inert diluents, carriers, disintegrants, adjuvants, surfactants, binders and/or lubricants. The tablets may also consist of several layers. The particular excipients, carriers and/or diluents that are suitable for the desired preparations will be familiar to the skilled man on the basis of his specialist knowledge. The preferred ones are those that are suitable for the particular formulation and method of administration that are desired. The preparations or formulations according to the invention may be prepared using methods known per se that are familiar to the skilled man, such as for example by mixing or combining at least one compound of formula I according to the invention, or a pharmaceutically acceptable salt of such a compound, and one or more excipients, carriers and/or diluents.

Combination Therapy

The compounds of the invention may further be combined with one or more, preferably one additional therapeutic agent. According to one embodiment the additional therapeutic agent is selected from the group of therapeutic agents useful in the treatment of diseases or conditions described hereinbefore, in particular associated with metabolic diseases or conditions such as for example diabetes mellitus, obesity, diabetic complications, hypertension, hyperlipidemia. Additional therapeutic agents which are suitable for such combinations include in particular those which for example potentiate the therapeutic effect of one or more active substances with respect to one of the indications mentioned and/or which allow the dosage of one or more active substances to be reduced.

Therefore a compound of the invention may be combined with one or more additional therapeutic agents selected from the group consisting of antidiabetic agents, agents for the treatment of overweight and/or obesity and agents for the treatment of high blood pressure, heart failure and/or atherosclerosis.

Antidiabetic agents are for example metformin, sulphonylureas, nateglinide, repaglinide, thiazolidinediones, PPAR-(alpha, gamma or alpha/gamma) agonists or modulators, alpha-glucosidase inhibitors, DPPIV inhibitors, SGLT2-inhibitors, insulin and insulin analogues, GLP-1 and GLP-1 analogues or amylin and amylin analogues, cycloset, 11β-HSD inhibitors. Other suitable combination partners are inhibitors of protein tyrosinephosphatase 1, substances that affect deregulated glucose production in the liver, such as e.g. inhibitors of glucose-6-phosphatase, or fructose-1,6-bisphosphatase, glycogen phosphorylase, glucagon receptor antagonists and inhibitors of phosphoenol pyruvate carboxykinase, glycogen synthase kinase or pyruvate dehydrokinase, alpha2-antagonists, CCR-2 antagonists or glucokinase activators. One or more lipid lowering agents are also suitable as combination partners, such as for example HMG-CoA-reductase inhibitors, fibrates, nicotinic acid and the derivatives thereof, PPAR-(alpha, gamma or alpha/gamma) agonists or modulators, PPAR-delta agonists, ACAT inhibitors or cholesterol absorption inhibitors such as, bile acid-binding substances such as, inhibitors of ileac bile acid transport, MTP inhibitors, or HDL-raising compounds such as CETP inhibitors or ABC1 regulators.

Therapeutic agents for the treatment of overweight and/or obesity are for example antagonists of the cannabinoid1 receptor, MCH-1 receptor antagonists, MC4 receptor agonists, NPY5 or NPY2 antagonists, β3-agonists, leptin or leptin mimetics, agonists of the 5HT2c receptor.

Therapeutic agents for the treatment of high blood pressure, chronic heart failure and/or atherosclerosis are for example A-II antagonists or ACE inhibitors, ECE inhibitors, diuretics, β-blockers, Ca-antagonists, centrally acting antihypertensives, antagonists of the alpha-2-adrenergic receptor, inhibitors of neutral endopeptidase, thrombocyte aggregation inhibitors and others or combinations thereof are suitable. Angiotensin II receptor antagonists are preferably used for the treatment or prevention of high blood pressure and complications of diabetes, often combined with a diuretic such as hydrochlorothiazide.

The dosage for the combination partners mentioned above is usually ⅕ of the lowest dose normally recommended up to 1/1 of the normally recommended dose.

Preferably, compounds of the present invention and/or pharmaceutical compositions comprising a compound of the present invention optionally in combination with one or more additional therapeutic agents are administered in conjunction with exercise and/or a diet.

Therefore, in another aspect, this invention relates to the use of a compound according to the invention in combination with one or more additional therapeutic agents described hereinbefore and hereinafter for the treatment of diseases or conditions which may be affected or which are mediated by the activation of the G-protein-coupled receptor GPR40, in particular diseases or conditions as described hereinbefore and hereinafter.

In yet another aspect the present invention relates a method for treating a disease or condition mediated by the activation of the G-protein-coupled receptor GPR40 in a patient that includes the step of administering to the patient, preferably a human, in need of such treatment a therapeutically effective amount of a compound of the present invention in combination with a therapeutically effective amount of one or more additional therapeutic agents described in hereinbefore and hereinafter, The use of the compound according to the invention in combination with the additional therapeutic agent may take place simultaneously or at staggered times.

The compound according to the invention and the one or more additional therapeutic agents may both be present together in one formulation, for example a tablet or capsule, or separately in two identical or different formulations, for example as a so-called kit-of-parts.

Consequently, in another aspect, this invention relates to a pharmaceutical composition which comprises a compound according to the invention and one or more additional therapeutic agents described hereinbefore and hereinafter, optionally together with one or more inert carriers and/or diluents.

Other features and advantages of the present invention will become apparent from the following more detailed Examples which illustrate, by way of example, the principles of the invention.

EXAMPLES

Preliminary Remarks

As a rule, $^1$H-NMR and/or mass spectra have been obtained for the compounds prepared. The $R_f$ values are determined using Merck silica gel 60 $F_{254}$ plates and UV light at 254 nm.

The terms "ambient temperature" and "room temperature" are used interchangeably and designate a temperature of about 20° C.

Analytical HPLC parameters employed for characterization of products (TFA denotes trifluoroacetic acid and FA denotes formic acid):

| Method: | 1 |
|---|---|
| Device: | Agilent 1200 with DA and MS detector |
| Column: | XBridge C18, 3 × 30 mm, 2.5 μm |
| Column Supplier: | Waters |

| Gradient/ Solvent Time [min] | % Solvent [H$_2$O, 0.1% FA] | % Solvent [Acetonitrile] | Flow [ml/min] | Temperature [° C.] |
|---|---|---|---|---|
| 0.00 | 97 | 3 | 2.2 | 60 |
| 0.20 | 97 | 3 | 2.2 | 60 |
| 1.20 | 0 | 100 | 2.2 | 60 |

| | | | | |
|---|---|---|---|---|
| 1.25 | 0 | 100 | 3 | 60 |
| 1.40 | 0 | 100 | 3 | 60 |

| Method: | 2 |
|---|---|
| Device: | Agilent 1200 with DA and MS detector |
| Column: | XBridge C18, 3 × 30 mm, 2.5 μm |
| Column Supplier: | Waters |

| Gradient/ Solvent Time [min] | % Solvent [H₂O, 0.1% TFA] | % Solvent [Acetonitrile] | Flow [mL/min] | Temperature [° C.] |
|---|---|---|---|---|
| 0.00 | 50 | 50 | 2.2 | 60 |
| 0.20 | 50 | 50 | 2.2 | 60 |
| 1.20 | 0 | 100 | 2.2 | 60 |
| 1.25 | 0 | 100 | 3 | 60 |
| 1.40 | 0 | 100 | 3 | 60 |

| Method: | 3 |
|---|---|
| Device: | Agilent 1200 with DA and MS detector |
| Column: | XBridge C18, 3 × 30 mm, 2.5 μm |
| Column Supplier: | Waters |

| Gradient/ Solvent Time [min] | % Solvent [H₂O, 0.1% NH₃] | % Solvent [Acetonitrile] | Flow [ml/min] | Temperature [° C.] |
|---|---|---|---|---|
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

| Method: | 4 |
|---|---|
| Device: | Agilent 1200 with DA and MS detector |
| Column: | XBridge C18, 3 × 30 mm, 2.5 μm |
| Column Supplier: | Waters |

| Gradient/ Solvent Time [min] | % Solvent [H₂O, 0.1% TFA] | % Solvent [Acetonitrile] | Flow [mL/min] | Temperature [° C.] |
|---|---|---|---|---|
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

| Method: | 5 |
|---|---|
| Device: | Agilent 1200 with DA and MS detector |
| Column: | XBridge C18, 3 × 30 mm, 2.5 μm |
| Column Supplier: | Waters |

| Gradient/ Solvent Time [min] | % Solvent [H₂O, 0.1% NH₃] | % Solvent [Acetonitrile] | Flow [ml/min] | Temperature [° C.] |
|---|---|---|---|---|
| 0.00 | 50 | 50 | 2.2 | 60 |
| 0.20 | 50 | 50 | 2.2 | 60 |
| 1.20 | 0 | 100 | 2.2 | 60 |
| 1.25 | 0 | 100 | 3 | 60 |
| 1.40 | 0 | 100 | 3 | 60 |

| Method: | 6 |
|---|---|
| Device: | Agilent 1200 with DA and MS detector |
| Column: | Sunfire, 3 × 30 mm, 2.5 μm |
| Column Supplier: | Waters |

| Gradient/ Solvent Time [min] | % Solvent [H₂O, 0.1% TFA] | % Solvent [Acetonitrile] | Flow [mL/min] | Temperature [° C.] |
|---|---|---|---|---|
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

| Method: | 7 |
|---|---|
| Device: | Agilent 1100 with DA and MS detector |
| Column: | XBridge C18, 4.6 × 30 mm, 3.5 μm |
| Column Supplier: | Waters |

| Gradient/ Solvent Time [min] | % Solvent [H₂O, 0.1% FA] | % Solvent [Methanol] | Flow ml/min] | Temperature [° C.] |
|---|---|---|---|---|
| 0.0 | 50 | 50 | 4 | 60 |
| 0.15 | 50 | 50 | 4 | 60 |
| 1.7 | 0 | 100 | 4 | 60 |
| 2.25 | 0 | 100 | 4 | 60 |

| Method: | 8 |
|---|---|
| Device: | Agilent 1100 with DAD and Waters MS detector |
| Column: | XBridge C18, 4.6 × 30 mm, 3.5 μm |
| Column Supplier: | Waters |

| Gradient/ Solvent Time [min] | % Solvent [H₂O, 0.1% NH₄OH] | % Solvent [Acetonitrile] | Flow [ml/min] | Temperature [° C.] |
|---|---|---|---|---|
| 0.0 | 98 | 2 | 2.5 | 60 |
| 1.5 | 0 | 100 | 2.5 | 60 |
| 1.8 | 0 | 100 | 2.5 | 60 |

The Examples that follow are intended to illustrate the present invention without restricting it:

Intermediate 1

[(S)-6-Hydroxy-2,3-dihydro-benzofuran-3-yl]acetic acid methyl ester

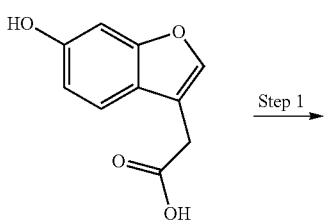

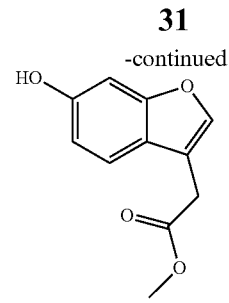

Step 2 →

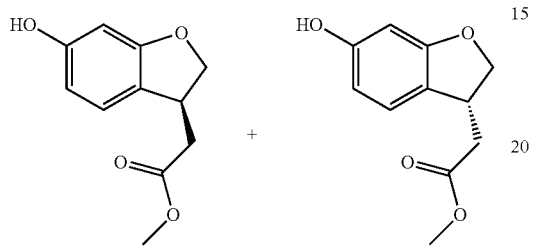

Step 1: (6-hydroxy-benzofuran-3-yl)-acetic acid methyl ester

A mixture of (6-hydroxy-benzofuran-3-yl)-acetic acid (for preparation see WO 2008001931; 14.0 g), concentrated sulfuric acid (5 mL), and methanol (250 mL) is stirred at reflux temperature for 4 h. After cooling to room temperature, the mixture is concentrated. Ethyl acetate is added to the residue, and the resulting mixture is washed with water, saturated aqueous $NaHCO_3$ solution and brine and dried ($MgSO_4$). The solvent is evaporated, and the residue is chromatographed on silica gel (cyclohexane/ethyl acetate 2:1→1:2) to give the title compound. Mass spectrum ($ESI^+$): m/z=207 $[M+H]^+$.

Step 2: (6-hydroxy-2,3-dihydro-benzofuran-3-yl)-acetic acid methyl ester

A mixture of (6-hydroxy-benzofuran-3-yl)-acetic acid methyl ester (5.00 g), 10% palladium on carbon (0.50 g), and methanol (50 mL) is shaken under hydrogen atmosphere (3 bar) at room temperature for 3 h. The catalyst is separated by filtration and the filtrate is concentrated. The residue is chromatographed on silica gel (cyclohexane/ethyl acetate 4:1→1:1) to give the racemic title compound. Mass spectrum ($ESI^+$): m/z=209 $[M+H]^+$.

The enantiomers may be separated by SFC on chiral phase (column: Daicel ADH, 5 μm, 250 mm×20 mm; eluent: $scCO_2$/(isopropanol+0.2% diethylamine) 80:20, 70 mL/min):

(S)-(6-Hydroxy-2,3-dihydro-benzofuran-3-yl)-acetic acid methyl ester: $t_R$=2.33 min.

(R)-(6-Hydroxy-2,3-dihydro-benzofuran-3-yl)-acetic acid methyl ester: $t_R$=2.75 min.

Alternatively, the pure enantiomer may be obtained as described in WO 2008001931.

Intermediate 2

{(S)-6-[(R)-4-Bromo-5-trifluoromethyl-indan-1-yloxy]-2,3-dihydro-benzofuran-3-yl}-acetic acid methyl ester

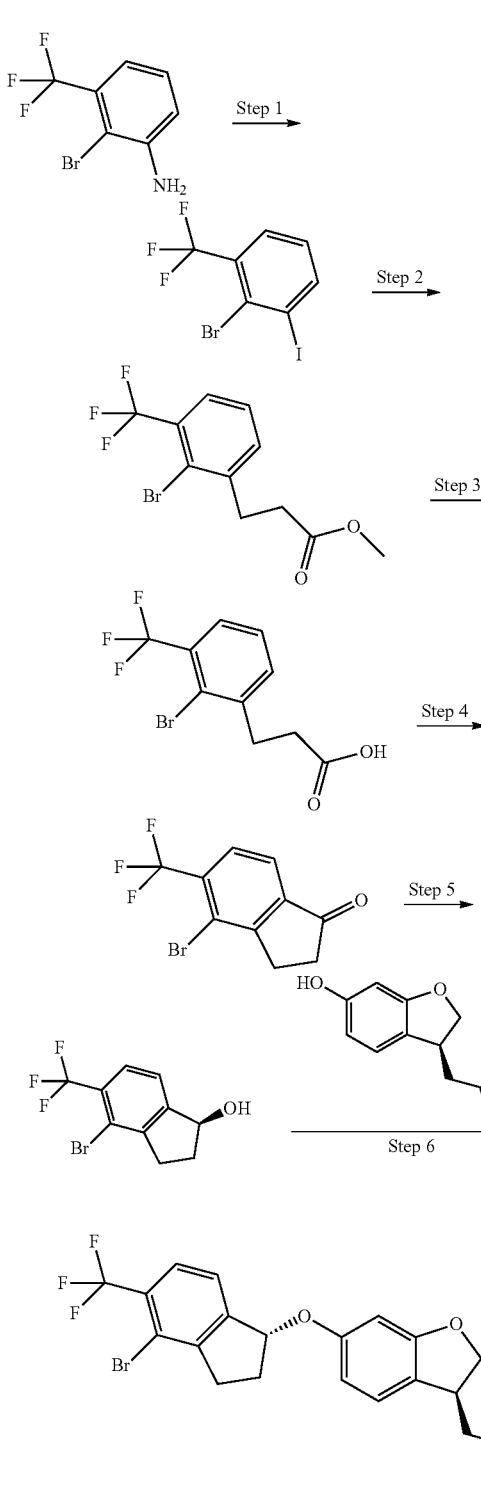

Step 1: 2-bromo-1-iodo-3-trifluoromethyl-benzene

An ice-cold solution of NaNO$_2$ (0.15 g) in water (0.5 mL) is added to a mixture of 2-bromo-3-trifluoromethyl-aniline (0.48 g), concentrated H$_2$SO$_4$ (2 mL), and water (1.8 mL) at ca. 5° C. The mixture is stirred in the cooling bath for 20 min and then poured into a solution of KI (0.56 g) and I$_2$ (0.56 g) in water (0.5 mL). After gas evolution ceases, the mixture is heated to 40° C. and stirred at this temperature for 1 h. The mixture is cooled to room temperature and aqueous Na$_2$SO$_3$ solution is added. The resulting mixture is extracted with ethyl acetate, and the combined extracts are dried (Na$_2$SO$_4$) and concentrated. The solvent is evaporated and the residue is chromatographed (cyclohexane/ethyl acetate 95:5→90:10) to give the title compound.

Step 2: 3-(2-bromo-3-trifluoromethyl-phenyl)-propionic acid methyl ester

A microwave suited vial charged with a stir bar, 2-bromo-1-iodo-3-trifluoromethyl-benzene (4.04 g), N,N-diisopropyl-ethylamine (4.0 mL), acrolein dimethyl acetal (1.76 g), tetrabutylammonium chloride (3.30 g), and dry N,N-dimethylformamide (10 mL) is purged with Ar for 5 min. Palladium(II) acetate (0.13 g) is added, the vial is sealed, and the mixture is stirred for 20 min at 120° C. in a microwave oven. After cooling to room temperature, the mixture is diluted with ethyl acetate, and the resulting mixture is washed with 1 M aqueous HCl solution and brine and dried (Na$_2$SO$_4$). The solvent is evaporated, and the residue is chromatographed (cyclohexane/ethyl acetate 90:10) to give the title compound.

Step 3: 3-(2-bromo-3-trifluoromethyl-phenyl)-propionic acid

The title compound is prepared from 3-(2-bromo-3-trifluoromethyl-phenyl)-propionic acid methyl ester following a procedure analogous to that described in Example 1; the title compound is precipitated from an acidic aqueous solution (pH ca. 4). LC (method 7): $t_R$=0.93 min; Mass spectrum (ESI$^-$): m/z=295/297 (Br) [M−H]$^-$.

Step 4: 4-bromo-5-trifluoromethyl-indan-1-one

Oxalyl chloride (6.8 mL) and N,N-dimethylformamide (0.1 mL) are added to a solution of 3-(2-bromo-3-trifluoromethyl-phenyl)-propionic acid (15.7 g) in dichloromethane (150 mL) at room temperature. The solution is stirred at reflux temperature for 2 h and then concentrated. Trifluoromethanesulfonic acid (60 ml) is added to the residue, and the resulting mixture is stirred at 55° C. for 4 h. After cooling to room temperature, the mixture is poured into ice-cold water, and the resulting mixture is stirred for 5 min. The precipitate formed is separated by filtration, washed with water, and dissolved in ethyl acetate. The solution is washed with aqueous NaHCO$_3$ solution, dried (Na$_2$SO$_4$), and concentrated. The residue is chromatographed on silica gel (cyclohexane/ethyl acetate 90:10→80:20) to afford the title compound. LC (method 4): $t_R$=1.04 min.

Step 5: (S)-4-bromo-5-trifluoromethyl-indan-1-ol

Formic acid (4.8 mL) is added to a solution of triethylamine (15.2 mL) in dichloromethane (100 mL) chilled in an ice bath. 4-Bromo-5-trifluoromethyl-indanone (10.0 g) dissolved in dichloromethane (40 ml) is added, and the flask is purged with Ar for 5 min. Chloro{[(1S,2S)-(−)-2-amino-1,2-diphenylethyl](4-toluenesulfonyl)amido}-(mesitylene)ruthenium (II) (0.50 g; alternatively, the catalyst is formed in situ from N-[(1S,2S)-2-amino-1,2-diphenylethyl]-4-methylbenzenesulfonamide and dichloro(p-cymene)-ruthenium(II) dimer) is added, and the mixture is stirred at room temperature overnight. The mixture is diluted with dichloromethane and washed with water and brine and dried (MgSO$_4$). The solvent is evaporated and the residue is chromatographed on silica gel (cyclohexane/ethyl acetate 80:20→20:80) to give the title compound. LC (method 4): $t_R$=1.00 min; Mass spectrum (ESI$^-$): m/z=279/281 (Br) [M−H]$^-$.

Step 6: {(S)-6-[(R)-4-bromo-5-trifluoromethyl-indan-1-yloxy]-2,3-dihydro-benzofuran-3-yl}-acetic acid methyl ester A solution of di-tert-butyl azodicarboxylate (6.3 g) in tetrahydrofuran (20 mL) is added dropwise over 45 min to a solution of [(S)-6-hydroxy-2,3-dihydro-benzofuran-3-yl]-acetic acid methyl ester (4.71 g), (S)-4-bromo-5-trifluoromethyl-indan-1-ol (6.00 g), and tri-n-butyl-phosphine (6.9 mL) in tetrahydrofuran (50 mL) at −10° C. The resulting solution is stirred in the cooling bath for 2.5 h and then diluted with water. The resulting mixture is extracted with ethyl acetate. The combined extracts are dried (MgSO$_4$) and concentrated. The residue is chromatographed on silica gel (cyclohexane/ethyl acetate 90:10→70:30) to give the title compound. LC (method 2): $t_R$=0.85 min; Mass spectrum (ESI$^+$): m/z=471/473 (Br) [M+H]$^+$.

Intermediate 3

{(S)-6-[(R)-4-Morpholin-4-ylmethyl-5-trifluoromethyl-indan-1-yloxy]-2,3-dihydro-benzofuran-3-yl}-acetic acid methyl ester

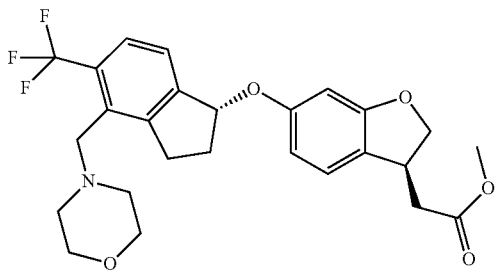 [SMILES: COC(=O)C[C@@H]1COc2cc(O[C@@H]3CCc4c3ccc(C(F)(F)F)c4CN3CCOCC3)ccc21]

A flask charged with a stir bar, {(S)-6-[(R)-4-bromo-5-trifluoromethyl-indan-1-yloxy]-2,3-dihydro-benzofuran-3-yl}-acetic acid methyl ester (120 mg), potassium morpholin-4-ylmethyltrifluoroborate (58 mg), Cs$_2$CO$_3$ (0.25 g), tetrahydrofuran (2.5 mL) and water (0.25 mL) is purged with Ar for 5 min. Palladium(II) acetate (4 mg) and 2-dicyclohexylphosphino-2',4',6'-triisopropyl-1,1'-biphenyl (X-Phos, 41 mg) are added, the flask is sealed, and the mixture is heated to 80° C. The mixture is stirred at this temperature overnight. After cooling to room temperature, water is added and the mixture is extracted with ethyl acetate. The combined extract is washed with brine, dried (Na$_2$SO$_4$), and concentrated. The residue is chromatographed on silica gel (cyclohexane/ethyl acetate) to give the title compound. LC (method 1): $t_R$=1.07 min; Mass spectrum (ESI⁺): m/z=492 [M+H]⁺.

Intermediate 4

{(S)-6-[(R)-4-(4-tert-Butoxycarbonyl-piperazin-1-ylmethyl)-5-trifluoromethyl-indan-1-yloxy]-2,3-dihydro-benzofuran-3-yl}-acetic acid methyl ester

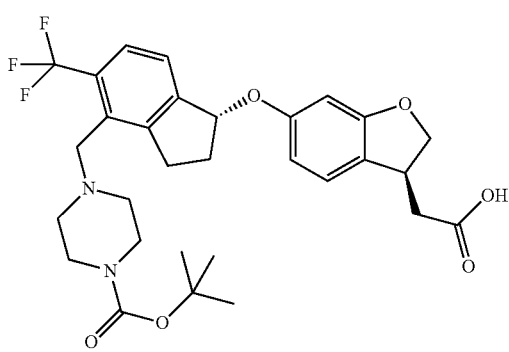 [SMILES: CC(C)(C)OC(=O)N1CCN(Cc2c(C(F)(F)F)ccc3c2CC[C@H]3Oc2ccc3c(c2)OC[C@H]3CC(=O)O)CC1]

The title compound is prepared from {(S)-6-[(R)-4-bromo-5-trifluoromethyl-indan-1-yloxy]-2,3-dihydro-benzofuran-3-yl}-acetic acid methyl ester and potassium (4-tert-butoxycarbonyl-piperazin-1-yl)methyltrifluoroborate following a procedure analogous to that described for Intermediate 3. LC (method 1): $t_R$=1.26 min; Mass spectrum (ESI⁺): m/z=591 [M+H]⁺.

Intermediate 5

{(S)-6-[(R)-4-Thiomorpholin-4-ylmethyl-5-trifluoromethyl-indan-1-yloxy]-2,3-dihydro-benzofuran-3-yl}-acetic acid methyl ester

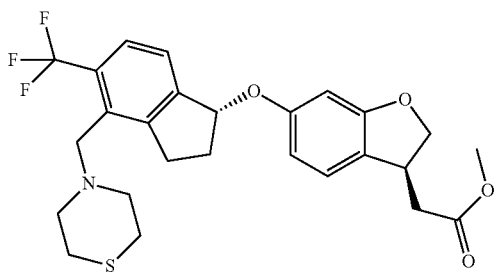 [SMILES: COC(=O)C[C@@H]1COc2cc(O[C@@H]3CCc4c3ccc(C(F)(F)F)c4CN3CCSCC3)ccc21]

The title compound is prepared from {(S)-6-[(R)-4-bromo-5-trifluoromethyl-indan-1-yloxy]-2,3-dihydro-benzofuran-3-yl}-acetic acid methyl ester and (thiomorpholinium-4-ylmethyl)trifluoroborate following a procedure analogous to that described for Intermediate 3. LC (method 1): $t_R$=1.19 min; Mass spectrum (ESI⁺): m/z=508 [M+H]⁺.

Intermediate 6

{(S)-6-[(R)-4-Pyrrolidin-1-ylmethyl-5-trifluoromethyl-indan-1-yloxy]-2,3-dihydro-benzofuran-3-yl}-acetic acid methyl ester

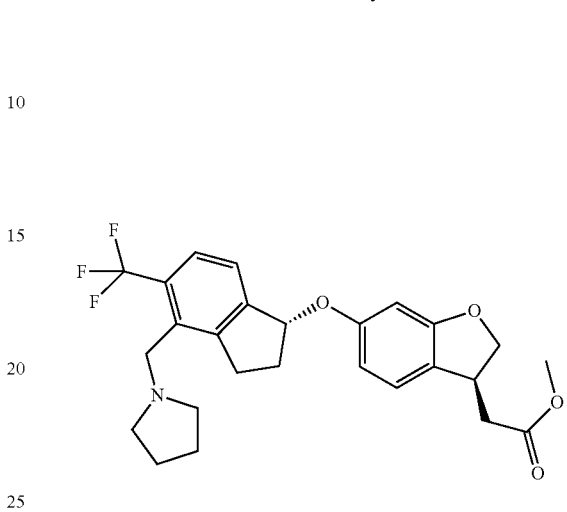

The title compound is prepared from {(S)-6-[(R)-4-bromo-5-trifluoromethyl-indan-1-yloxy]-2,3-dihydro-benzofuran-3-yl}-acetic acid methyl ester and potassium pyrrolidin-1-ylmethyltrifluoroborate following a procedure analogous to that described for Intermediate 3. LC (method 1): $t_R$=0.92 min; Mass spectrum (ESI⁺): m/z=476 [M+H]⁺.

Intermediate 7

{(S)-6-[(R)-4-Piperidin-1-ylmethyl-5-trifluoromethyl-indan-1-yloxy]-2,3-dihydro-benzofuran-3-yl}-acetic acid methyl ester

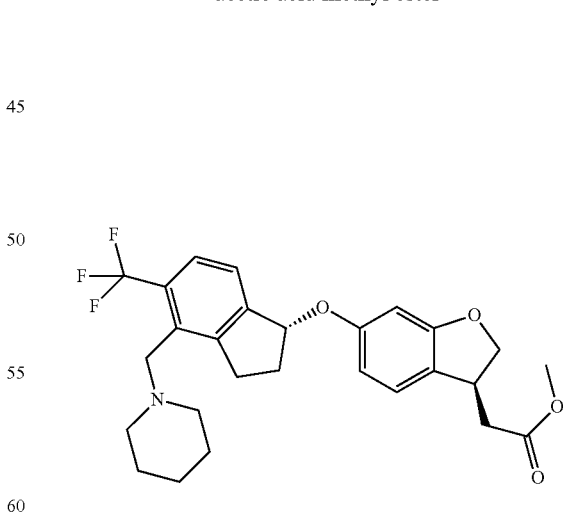

The title compound is prepared from {(S)-6-[(R)-4-bromo-5-trifluoromethyl-indan-1-yloxy]-2,3-dihydro-benzofuran-3-yl}-acetic acid methyl ester and potassium piperidin-1-ylmethyltrifluoroborate following a procedure analogous to that described for Intermediate 3. LC (method 5): $t_R$=1.15 min; Mass spectrum (ESI⁺): m/z=490 [M+H]⁺.

Intermediate 8

Potassium (2-methyl-4,5,6,7-tetrahydro-thiazolo[5,4-c]pyridin-5-yl)methyltrifluoroborate

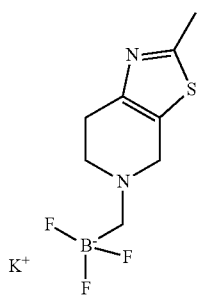

A mixture of 2-methyl-4,5,6,7-tetrahydro-thiazolo[5,4-c]pyridine (3.00 g), potassium bromomethyltrifluoroborate (3.91 g), KHCO₃ (1.95 g), KI (0.32 g), and tetrahydrofuran (25 mL) is stirred at reflux temperature for 4 h. After cooling to room temperature, the solvent is evaporated and the residue is suspended in acetone. The insoluble salts are separated by filtration and the filtrate is treated with diethyl ether. The precipitate is separated by filtration and dried to give the title compound (alternatively, the crude product is purified by chromatography on silica gel using dichloromethane and methanol as eluent). Mass spectrum (ESI⁻): m/z=235 [M]⁻.

Intermediate 9

{(S)-6-[(R)-4-(2-Methyl-4,5,6,7-tetrahydro-thiazolo[5,4-c]pyridin-5-ylmethyl)-5-trifluoromethyl-indan-1-yloxy]-2,3-dihydro-benzofuran-3-yl}-acetic acid methyl ester

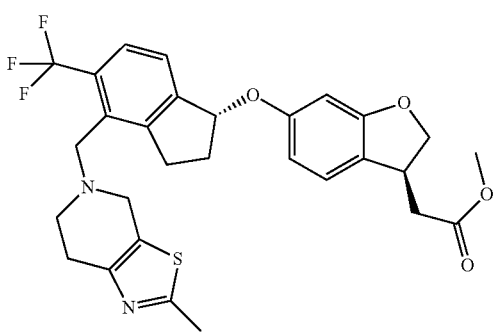 [SMILES: COC(=O)C[C@@H]1COc2cc(O[C@@H]3CCc4c3ccc(C(F)(F)F)c4CN3CCc4nc(C)sc4C3)ccc21]

The title compound is prepared from {(S)-6-[(R)-4-bromo-5-trifluoromethyl-indan-1-yloxy]-2,3-dihydro-benzofuran-3-yl}-acetic acid methyl ester and potassium (2-methyl-4,5,6,7-tetrahydro-thiazolo[5,4-c]pyridin-1-yl)methyltrifluoroborate following a procedure analogous to that described for Intermediate 3. LC (method 1): $t_R$=1.02 min; Mass spectrum (ESI⁺): m/z=559 [M+H]⁺.

Intermediate 10

4,4-Difluoro-piperidinium-1-yl)methyltrifluoroborate

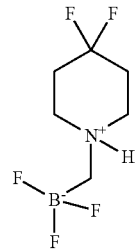

The title compound is prepared from potassium bromomethyltrifluoroborate and 4,4-difluoro-piperidine following a procedure analogous to that described for Intermediate 8; the crude product is purified by chromatography on silica gel (dichloromethane/methanol). Mass spectrum (ESI⁻): m/z=202 [M]⁻.

Intermediate 11

{(S)-6-[(R)-4-(4,4-Difluoro-piperidin-1-yl-methyl)-5-trifluoromethyl-indan-1-yloxy]-2,3-dihydro-benzofuran-3-yl}-acetic acid methyl ester

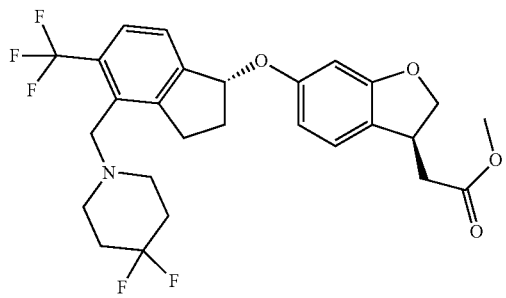 [SMILES: COC(=O)C[C@@H]1COc2cc(O[C@@H]3CCc4c3ccc(C(F)(F)F)c4CN3CCC(F)(F)CC3)ccc21]

The title compound is prepared from {(S)-6-[(R)-4-bromo-5-trifluoromethyl-indan-1-yloxy]-2,3-dihydro-benzofuran-3-yl}-acetic acid methyl ester and (4,4-difluoropiperidinium-1-yl)methyltrifluoroborate following a procedure analogous to that described for Intermediate 3. LC (method 1): $t_R$=1.27 min; Mass spectrum (ESI⁺): m/z=526 [M+H]⁺.

Intermediate 12

6-Azonia-spiro[2.5]octan-6-yl)methyltrifluoroborate

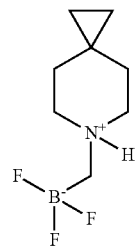

The title compound is prepared from potassium bromomethyltrifluoroborate and 6-aza-spiro[2.5]octane following a procedure analogous to that described for Intermediate 8; the crude product is purified by chromatography on silica gel (dichloromethane/methanol). Mass spectrum (ESI⁻): m/z=192 [M]⁻.

Intermediate 13

{(S)-6-[(R)-4-(6-Aza-spiro[2.5]oct-6-ylmethyl)-5-trifluoromethyl-indan-1-yloxy]-2,3-dihydro-benzofuran-3-yl}-acetic acid methyl ester

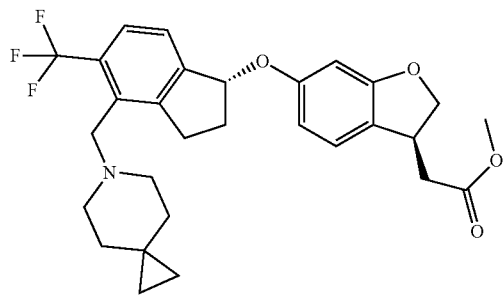 [SMILES: COC(=O)C[C@@H]1COc2cc(O[C@@H]3CCc4c3ccc(C(F)(F)F)c4CN3CCC4(CC3)CC4)ccc21]

The title compound is prepared from {(S)-6-[(R)-4-bromo-5-trifluoromethyl-indan-1-yloxy]-2,3-dihydro-benzofuran-3-yl}-acetic acid methyl ester and (6-azonia-spiro[2.5]octan-6-yl)methyltrifluoroborate following a procedure analogous to that described for Intermediate 3. LC (method 1): $t_R$=0.96 min; Mass spectrum (ESI⁺): m/z=516 [M+H]⁺.

Intermediate 14

[1,4]Oxazepanium-4-yl)methyltrifluoroborate

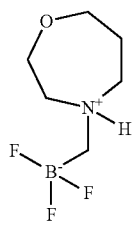 [SMILES: F[B-](F)(F)C[NH+]1CCCOCC1]

The title compound is prepared from potassium bromomethyltrifluoroborate and [1,4]oxazepane following a procedure analogous to that described for Intermediate 8; the crude product is purified by chromatography on silica gel (dichloromethane/methanol). Mass spectrum (ESI⁻): m/z=182 [M]⁻.

Intermediate 15

{(S)-6-[(R)-4-[1,4]Oxazepan-4-ylmethyl-5-trifluoromethyl-indan-1-yloxy]-2,3-dihydro-benzofuran-3-yl}-acetic acid methyl ester

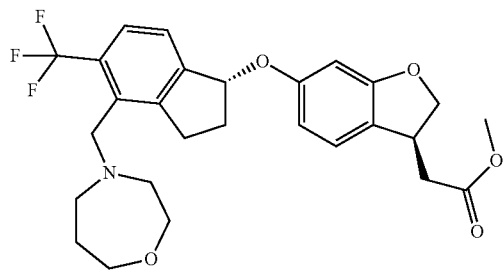 [SMILES: COC(=O)C[C@@H]1COc2cc(O[C@@H]3CCc4c3ccc(C(F)(F)F)c4CN3CCCOCC3)ccc21]

The title compound is prepared from {(S)-6-[(R)-4-bromo-5-trifluoromethyl-indan-1-yloxy]-2,3-dihydro-benzofuran-3-yl}-acetic acid methyl ester and ([1,4]oxazepanium-4-yl)methyltrifluoroborate following a procedure analogous to that described for Intermediate 3. LC (method 1): $t_R$=0.94 min; Mass spectrum (ESI⁺): m/z=506 [M+H]⁺.

Intermediate 16

4-Methoxy-piperidinium-1-yl)methyltrifluoroborate

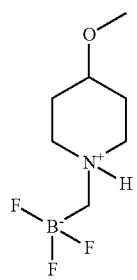

The title compound is prepared from potassium bromomethyltrifluoroborate and 4-methoxy-piperidine following a procedure analogous to that described for Intermediate 8; the crude product is purified by chromatography on silica gel (dichloromethane/methanol).

Intermediate 17

{(S)-6-[(R)-4-(4-Methoxy-piperidin-1-ylmethyl)-5-trifluoromethyl-indan-1-yloxy]-2,3-dihydro-benzofuran-3-yl}-acetic acid methyl ester

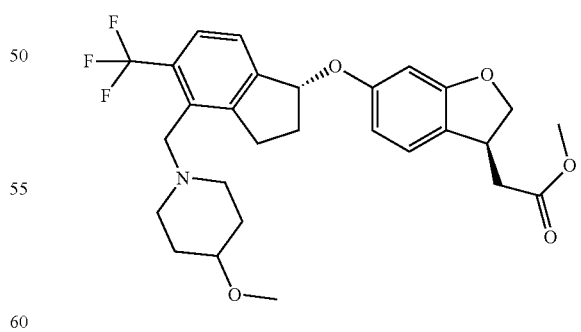

The title compound is prepared from {(S)-6-[(R)-4-bromo-5-trifluoromethyl-indan-1-yloxy]-2,3-dihydro-benzofuran-3-yl}-acetic acid methyl ester and (4-methoxy-piperidinium-1-yl)methyltrifluoroborate following a procedure analogous to that described for Intermediate 3. LC (method 1): $t_R$=0.91 min; Mass spectrum (ESI⁺): m/z=520 [M+H]⁺.

Intermediate 18

1-Oxa-8-azonia-spiro[4.5]dec-8-yl)methyltrifluoroborate

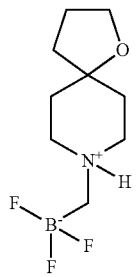 [SMILES: F[B-](F)(F)C[NH+]1CCC2(CCCO2)CC1]

The title compound is prepared from potassium bromomethyltrifluoroborate and 1-oxa-8-aza-spiro[4.5]decane following a procedure analogous to that described for Intermediate 8; the crude product is purified by chromatography on silica gel (dichloromethane/methanol). Mass spectrum (ESI⁻): m/z=222 [M]⁻.

Intermediate 19

{(S)-6-[(R)-4-(1-Oxa-8-aza-spiro[4.5]dec-8-ylmethyl)-5-trifluoromethyl-indan-1-yloxy]-2,3-dihydro-benzofuran-3-yl}-acetic acid methyl ester

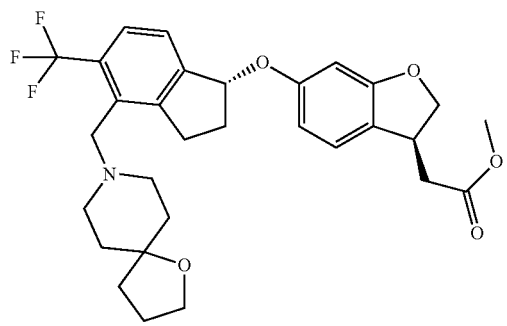 [SMILES: COC(=O)C[C@@H]1COc2cc(O[C@@H]3CCc4c3ccc(C(F)(F)F)c4CN3CCC4(CCCO4)CC3)ccc21]

The title compound is prepared from {(S)-6-[(R)-4-bromo-5-trifluoromethyl-indan-1-yloxy]-2,3-dihydro-benzofuran-3-yl}-acetic acid methyl ester and (1-oxa-8-azonia-spiro[4.5]dec-8-yl)methyltrifluoroborate following a procedure analogous to that described for Intermediate 3. LC (method 1): $t_R$=0.93 min; Mass spectrum (ESI⁺): m/z=546 [M+H]⁺.

Intermediate 20

3-Azonia-bicyclo[3.1.0]hex-3-yl)methyltrifluoroborate

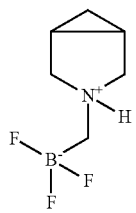 [SMILES: F[B-](F)(F)C[NH+]1CC2CC2C1]

The title compound is prepared from potassium bromomethyltrifluoroborate and 3-aza-bicyclo[3.1.0]hexane following a procedure analogous to that described for Intermediate 8; the crude product is purified by chromatography on silica gel (dichloromethane/methanol). Mass spectrum (ESI⁻): m/z=164 [M]⁻.

Intermediate 21

{(S)-6-[(R)-4-(3-Aza-bicyclo[3.1.0]hex-3-ylmethyl)-5-trifluoromethyl-indan-1-yloxy]-2,3-dihydro-benzofuran-3-yl}-acetic acid methyl ester

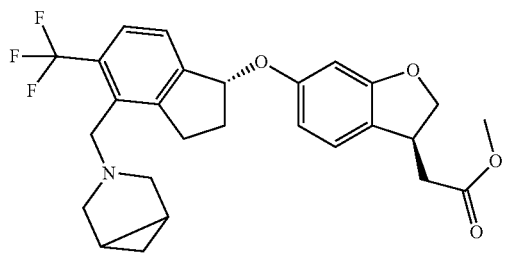 [SMILES: COC(=O)C[C@@H]1COc2cc(O[C@@H]3CCc4c3ccc(C(F)(F)F)c4CN3CC4CC4C3)ccc21]

The title compound is prepared from {(S)-6-[(R)-4-bromo-5-trifluoromethyl-indan-1-yloxy]-2,3-dihydro-benzofuran-3-yl}-acetic acid methyl ester and (3-azonia-bicyclo[3.1.0] hex-3-yl)methyltrifluoroborate following a procedure analogous to that described for Intermediate 3. LC (method 1): $t_R$=0.96 min; Mass spectrum (ESI⁺): m/z=488 [M+H]⁺.

Intermediate 22

4-Hydroxymethyl-piperidinium-1-yl)methyltrifluoroborate

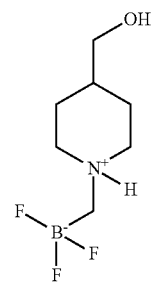

The title compound is prepared from potassium bromomethyltrifluoroborate and 4-hydroxymethyl-piperidine following a procedure analogous to that described for Intermediate 8; the crude product is purified by chromatography on silica gel (dichloromethane/methanol).

Intermediate 23

{(S)-6-[(R)-4-(4-Hydroxymethyl-piperidin-1-ylmethyl)-5-trifluoromethyl-indan-1-yloxy]-2,3-dihydro-benzofuran-3-yl}-acetic acid methyl ester

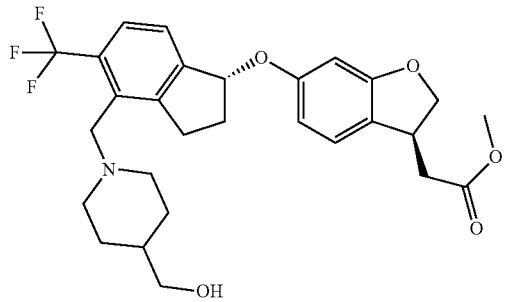 [SMILES: COC(=O)C[C@@H]1COc2cc(O[C@@H]3CCc4c3ccc(C(F)(F)F)c4CN3CCC(CO)CC3)ccc21]

The title compound is prepared from {(S)-6-[(R)-4-bromo-5-trifluoromethyl-indan-1-yloxy]-2,3-dihydro-benzofuran-3-yl}-acetic acid methyl ester and (4-hydroxymethyl-piperidinium-1-yl)methyltrifluoroborate following a procedure analogous to that described for Intermediate 3.

Intermediate 24

4-Hydroxy-4-methyl-piperidinium-1-yl)methyltrifluoroborate

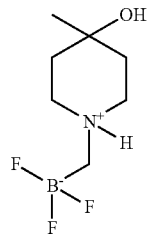

The title compound is prepared from potassium bromomethyltrifluoroborate and 4-hydroxy-4-methyl-piperidine following a procedure analogous to that described for Intermediate 8; the crude product is purified by chromatography on silica gel (dichloromethane/methanol). Mass spectrum (ESI⁻): m/z=196 [M]⁻.

Intermediate 25

{(S)-6-[(R)-4-(4-Hydroxy-4-methyl-piperidin-1-ylmethyl)-5-trifluoromethyl-indan-1-yloxy]-2,3-dihydro-benzofuran-3-yl}-acetic acid methyl ester

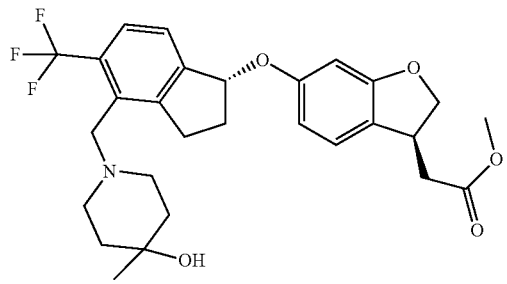 [SMILES: COC(=O)C[C@@H]1COc2cc(O[C@@H]3CCc4c3ccc(C(F)(F)F)c4CN3CCC(C)(O)CC3)ccc21]

The title compound is prepared from {(S)-6-[(R)-4-bromo-5-trifluoromethyl-indan-1-yloxy]-2,3-dihydro-benzofuran-3-yl}-acetic acid methyl ester and (4-hydroxy-4-methyl-piperidinium-1-yl)methyltrifluoroborate following a procedure analogous to that described for Intermediate 3. LC (method 1): $t_R$=0.86 min; Mass spectrum (ESI⁺): m/z=520 [M+H]⁺.

Intermediate 26

{(S)-6-[(R)-4-piperazin-1-ylmethyl-5-trifluoromethyl-indan-1-yloxy]-2,3-dihydro-benzofuran-3-yl}-acetic acid methyl ester

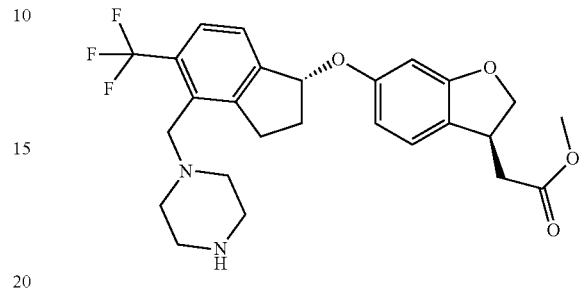

4 M HCl in 1,4-dioxane (5 mL) is added to a solution of {(S)-6-[(R)-4-(4-tert-butoxycarbonyl-piperazin-1-ylmethyl)-5-trifluoromethyl-indan-1-yloxy]-2,3-dihydro-benzofuran-3-yl}-acetic acid methyl ester (0.42 g) in dichloromethane (5 mL) at room temperature. The solution is stirred at room temperature for 2.5 h. The solution is basified with aqueous K₂CO₃ solution and extracted with dichloromethane. The combined extract is dried (Na₂SO₄) and concentrated to give the crude title compound that is used without further purification in subsequent transformations. LC (method 4): $t_R$=0.98 min; Mass spectrum (ESI⁺): m/z=491 [M+H]⁺.

Intermediate 27

{(S)-6-[(R)-4-(4-Methoxycarbonyl-piperazin-1-ylmethyl)-5-trifluoromethyl-indan-1-yloxy]-2,3-dihydro-benzofuran-3-yl}-acetic acid methyl ester

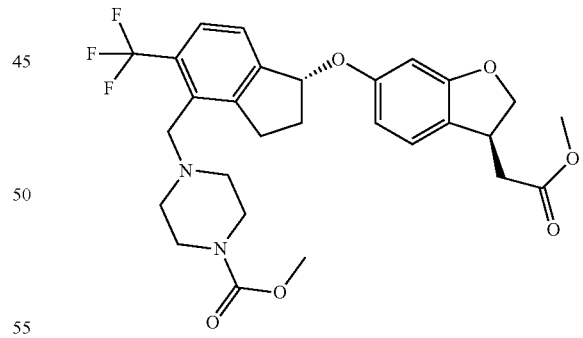

Methyl chloroformate (11 μL) is added to a solution of {(S)-6-[(R)-4-piperazin-1-ylmethyl-5-trifluoromethyl-indan-1-yloxy]-2,3-dihydro-benzofuran-3-yl}-acetic acid methyl ester (60 mg) and triethylamine (68 μL) in dichloromethane (2 mL) chilled in an ice bath. The cooling bath is removed and the solution is stirred at room temperature for 2 h. Water is added and the resulting mixture is extracted with dichloromethane. The combined extracts are washed with brine and dried (Na₂SO₄). The solvent is evaporated and the residue is chromatographed on reversed phase (HPLC; acetonitrile/water) to give the title compound. LC (method 4): $t_R$=0.99 min; Mass spectrum (ESI$^+$): m/z=549 [M+H]$^+$.

Intermediate 28 cis-2,6-Dimethyl-morpholinium-4-yl)methyltrifluoroborate

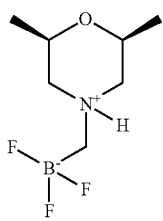

The title compound is prepared from potassium bromomethyltrifluoroborate and cis-2,6-dimethyl-morpholine following a procedure analogous to that described for Intermediate 8; the crude product is purified by chromatography on silica gel (dichloromethane/methanol). Mass spectrum (ESI$^-$): m/z=196 [M]$^-$.

Intermediate 29

{(S)-6-[(R)-4-(cis-2,6-Dimethyl-morpholin-4-ylmethyl)-5-trifluoromethyl-indan-1-yloxy]-2,3-dihydro-benzofuran-3-yl}-acetic acid methyl ester

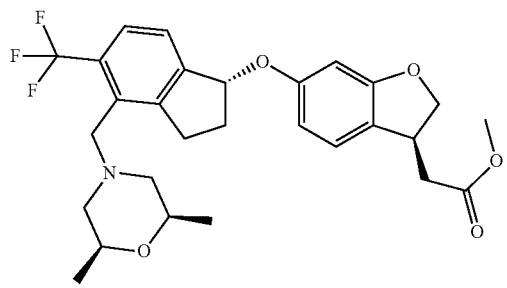 [SMILES: COC(=O)C[C@@H]1COc2cc(O[C@@H]3CCc4c3ccc(C(F)(F)F)c4CN3C[C@@H](C)O[C@@H](C)C3)ccc21]

The title compound is prepared from {(S)-6-[(R)-4-bromo-5-trifluoromethyl-indan-1-yloxy]-2,3-dihydro-benzofuran-3-yl}-acetic acid methyl ester and (cis-2,6-dimethyl-morpholinium-4-yl)methyltrifluoroborate following a procedure analogous to that described for Intermediate 3.

Intermediate 30

Azepanium-1-ylmethyltrifluoroborate

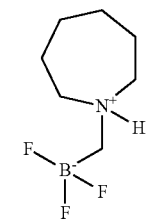 [SMILES: F[B-](F)(F)C[NH+]1CCCCCC1]

The title compound is prepared from potassium bromomethyltrifluoroborate and azepane following a procedure analogous to that described for Intermediate 8; the crude product is purified by chromatography on silica gel (dichloromethane/methanol). Mass spectrum (ESI$^-$): m/z=180 [M]$^-$.

Intermediate 31

{(S)-6-[(R)-4-Azepan-1-ylmethyl-5-trifluoromethyl-indan-1-yloxy]-2,3-dihydro-benzofuran-3-yl}-acetic acid methyl ester

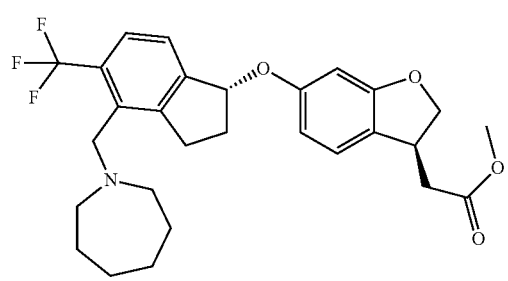 [SMILES: COC(=O)C[C@@H]1COc2cc(O[C@@H]3CCc4c3ccc(C(F)(F)F)c4CN3CCCCCC3)ccc21]

The title compound is prepared from {(S)-6-[(R)-4-bromo-5-trifluoromethyl-indan-1-yloxy]-2,3-dihydro-benzofuran-3-yl}-acetic acid methyl ester and azepanium-1-ylmethyltrifluoroborate following a procedure analogous to that described for Intermediate 3. LC (method 3): $t_R$=1.35 min; Mass spectrum (ESI$^+$): m/z=504 [M+H]$^+$.

Intermediate 32

{(S)-6-[(R)-4-(4-Ethoxycarbonyl-piperazin-1-ylmethyl)-5-trifluoromethyl-indan-1-yloxy]-2,3-dihydro-benzofuran-3-yl}-acetic acid methyl ester

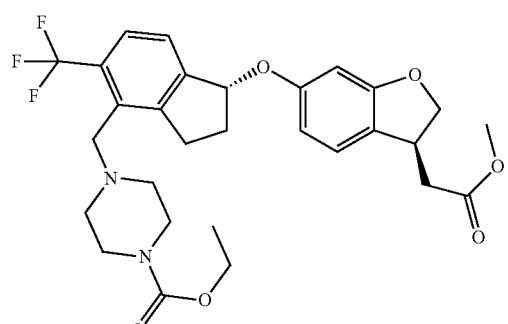

The title compound is prepared from ethyl chloroformate and {(S)-6-[(R)-4-piperazin-1-ylmethyl-5-trifluoromethyl-indan-1-yloxy]-2,3-dihydro-benzofuran-3-yl}-acetic acid methyl ester following a procedure analogous to that

Intermediate 33

{(S)-6-[(R)-4-(4-Propionyl-piperazin-1-ylmethyl)-5-trifluoromethyl-indan-1-yloxy]-2,3-dihydro-benzofuran-3-yl}-acetic acid methyl ester

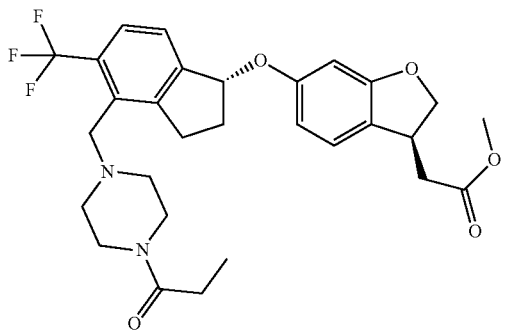 [SMILES: CCC(=O)N1CCN(Cc2c(C(F)(F)F)ccc3c2CC[C@H]3Oc2ccc3c(c2)OC[C@H]3CC(=O)OC)CC1]

The title compound is prepared from propionyl chloride and {(S)-6-[(R)-4-piperazin-1-ylmethyl-5-trifluoromethyl-indan-1-yloxy]-2,3-dihydro-benzofuran-3-yl}-acetic acid methyl ester following a procedure analogous to that described for Intermediate 27; pyridine instead of triethylamine is used. LC (method 4): $t_R$=0.97 min; Mass spectrum (ESI$^+$): m/z=547 [M+H]$^+$.

Intermediate 34

{(S)-6-[(R)-4-(4-Isopropoxycarbonyl-piperazin-1-ylmethyl)-5-trifluoromethyl-indan-1-yloxy]-2,3-dihydro-benzofuran-3-yl}-acetic acid methyl ester

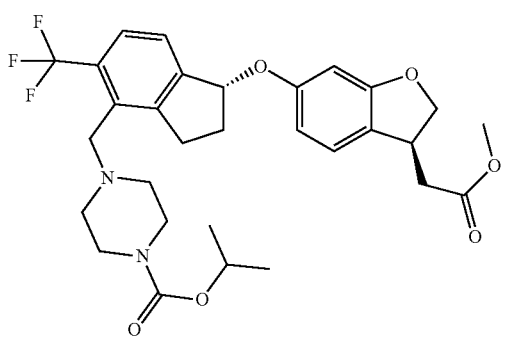 [SMILES: COC(=O)C[C@@H]1COc2cc(O[C@@H]3CCc4c3ccc(C(F)(F)F)c4CN3CCN(C(=O)OC(C)C)CC3)ccc21]

The title compound is prepared from isopropyl chloroformate and {(S)-6-[(R)-4-piperazin-1-ylmethyl-5-trifluoromethyl-indan-1-yloxy]-2,3-dihydro-benzofuran-3-yl}-acetic acid methyl ester following a procedure analogous to that described for Intermediate 27. LC (method 4): $t_R$=1.05 min; Mass spectrum (ESI$^+$): m/z=577 [M+H]$^+$.

Intermediate 35

2,2-Dimethyl-morpholinium-4-yl)methyltrifluoroborate

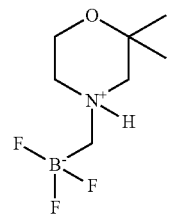

The title compound is prepared from potassium bromomethyltrifluoroborate and 2,2-dimethyl-morpholine following a procedure analogous to that described for Intermediate 8; the crude product is purified by chromatography on silica gel (dichloromethane/methanol). Mass spectrum (ESI$^-$): m/z=196 [M]$^-$.

Intermediate 36

{(S)-6-[(R)-4-(2,2-Dimethyl-morpholin-4-ylmethyl)-5-trifluoromethyl-indan-1-yloxy]-2,3-dihydro-benzofuran-3-yl}-acetic acid methyl ester

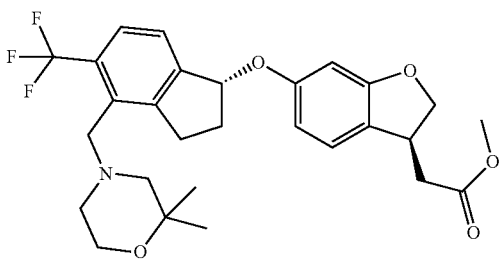 [SMILES: COC(=O)C[C@@H]1COc2cc(O[C@@H]3CCc4c3ccc(C(F)(F)F)c4CN3CCOC(C)(C)C3)ccc21]

The title compound is prepared from {(S)-6-[(R)-4-bromo-5-trifluoromethyl-indan-1-yloxy]-2,3-dihydro-benzofuran-3-yl}-acetic acid methyl ester and (2,2-dimethyl-morpholinium-4-yl)methyltrifluoroborate following a procedure analogous to that described for Intermediate 3. LC (method 3): $t_R$=1.27 min; Mass spectrum (ESI$^+$): m/z=520 [M+H]$^+$.

Intermediate 37

{(S)-6-[(R)-5-Trifluoromethyl-4-vinyl-indan-1-yloxy]-2,3-dihydro-benzofuran-3-yl}-acetic acid methyl ester

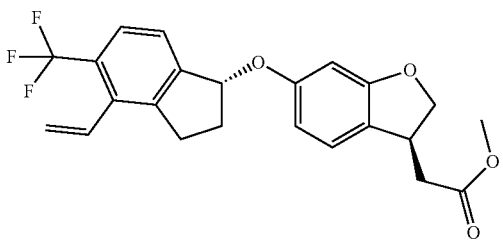 [SMILES: C=Cc1c(C(F)(F)F)ccc2c1CC[C@H]2Oc1ccc2c(c1)OC[C@H]2CC(=O)OC]

A flask charged with a stir bar, {(S)-6-[(R)-4-bromo-5-trifluoromethyl-indan-1-yloxy]-2,3-dihydro-benzofuran-3- yl}-acetic acid methyl ester (1.00 g), vinylboronic acid pinacol ester (0.39 g), K$_3$PO$_4$ (1.80 g), toluene (8 mL) and water (0.8 mL) is purged with Ar for 10 min. Palladium(II) acetate (24 mg) and dicyclohexyl-(2',6'-dimethoxybiphenyl-2-yl)-phosphine (S-Phos, 87 mg) are added, the flask is sealed, and the mixture is heated to 100° C. The mixture is stirred at this temperature overnight. After cooling to room temperature, water is added and the mixture is extracted with ethyl acetate. The combined extract is washed with brine, dried (charcoal/Na$_2$SO$_4$), and concentrated. The crude product is submitted to the next reaction step without further purification. LC (method 4): t$_R$=1.26 min; Mass spectrum (ESI$^+$): m/z=441 [M+Na]$^+$.

Intermediate 38

{(S)-6-[(R)-4-Formyl-5-trifluoromethyl-indan-1-yloxy]-2,3-dihydro-benzofuran-3-yl}-acetic acid methyl ester

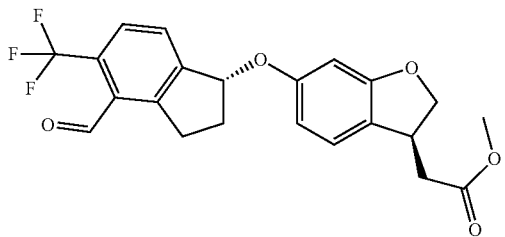 [SMILES: COC(=O)C[C@@H]1COc2cc(O[C@@H]3CCc4c3ccc(C(F)(F)F)c4C=O)ccc21]

NaIO$_4$ (1.80 g) and OsO$_4$ (4% in water, 50 µL) are added to a mixture of {(S)-6-[(R)-5-trifluoromethyl-4-vinyl-indan-1-yloxy]-2,3-dihydro-benzofuran-3-yl}-acetic acid methyl ester (1.25 g), tetrahydrofuran (16 mL), and water (4 mL) at room temperature. The mixture is stirred at 50° C. overnight. After cooling to room temperature, water is added and the mixture is extracted with ethyl acetate. The combined extract is washed with brine, dried (Na$_2$SO$_4$), and concentrated. The residue is chromatographed on silica gel (cyclohexane/ethyl acetate) to give the title compound. LC (method 4): t$_R$=1.19 min; Mass spectrum (ESI$^+$): m/z=421 [M+H]$^+$.

Intermediate 39

{(S)-6-[(R)-4-(8-Oxa-3-aza-bicyclo[3.2.1]oct-3-ylmethyl)-5-trifluoromethyl-indan-1-yloxy]-2,3-dihydro-benzofuran-3-yl}-acetic acid methyl ester

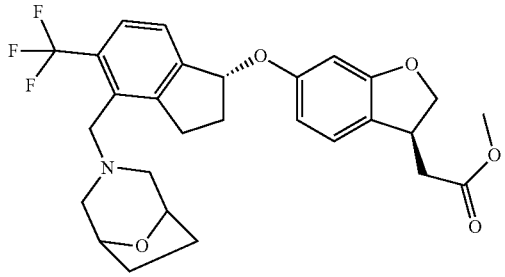 [SMILES: COC(=O)C[C@@H]1COc2cc(O[C@@H]3CCc4c3ccc(C(F)(F)F)c4CN3CC4CCC(C3)O4)ccc21]

NaHB(O$_2$CCH$_3$)$_3$ (30 mg) is added to a mixture of {(S)-6-[(R)-4-formyl-5-trifluoromethyl-indan-1-yloxy]-2,3-dihydro-benzofuran-3-yl}-acetic acid methyl ester (20 mg), 8-oxa-3-aza-bicyclo[3.2.1]octane hydrochloride (14 mg), sodium acetate (4 mg), and 1,2-dichloroethane (1 mL) at room temperature. The mixture is stirred at room temperature overnight. 1 M aqueous HCl solution is added, the resulting mixture is stirred for 10 min, and then water is added. The mixture is basified with aqueous K$_2$CO$_3$ solution and extracted with ethyl acetate. The combined extract is washed with brine, dried (Na$_2$SO$_4$), and concentrated to give the title compound. LC (method 4): t$_R$=1.15 min; Mass spectrum (ESI$^+$): m/z=518 [M+H]$^+$.

Intermediate 40

{(S)-6-[(R)-4-Hydroxymethyl-5-trifluoromethyl-indan-1-yloxy]-2,3-dihydro-benzofuran-3-yl}-acetic acid methyl ester

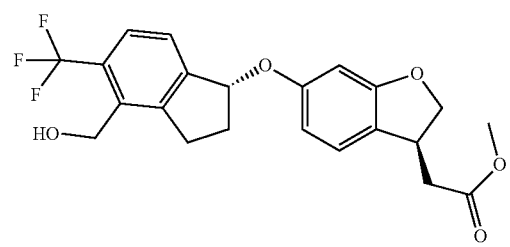 [SMILES: COC(=O)C[C@@H]1COc2cc(O[C@@H]3CCc4c3ccc(C(F)(F)F)c4CO)ccc21]

NaBH$_4$ (18 mg) is added to a solution of {(S)-6-[(R)-4-formyl-5-trifluoromethyl-indan-1-yloxy]-2,3-dihydro-benzofuran-3-yl}-acetic acid methyl ester (0.20 g) in tetrahydrofuran (4 mL) and water (1 mL) at room temperature. The mixture is stirred at room temperature for 30 min. 1 N aqueous HCl solution is added and the mixture is extracted with ethyl acetate. The combined extract is washed with brine, dried (Na$_2$SO$_4$), and concentrated to give the title compound. The crude product is submitted to the next reaction step without further purification. LC (method 4): t$_R$=1.09 min; Mass spectrum (ESI$^+$): m/z=445 [M+Na]$^+$.

Intermediate 41

{(S)-6-[(R)-4-Bromomethyl-5-trifluoromethyl-indan-1-yloxy]-2,3-dihydro-benzofuran-3-yl}-acetic acid methyl ester

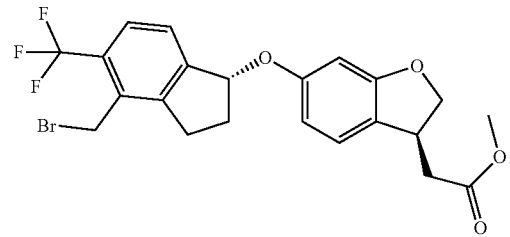 [SMILES: COC(=O)C[C@@H]1COc2cc(O[C@@H]3CCc4c3ccc(C(F)(F)F)c4CBr)ccc21]

Methylsulfonyl bromide (0.96 mL) is added to a solution of {(S)-6-[(R)-4-hydroxymethyl-5-trifluoromethyl-indan-1-yloxy]-2,3-dihydro-benzofuran-3-yl}-acetic acid methyl ester (2.00 g) and triethylamine (1.98 mL) in dichloromethane (20 mL) chilled in an ice bath. The cooling bath is removed, and the solution is stirred at room temperature overnight. More dichloromethane is added, and the resulting solution is washed with aqueous NaHCO$_3$ solution and brine, dried (Na$_2$SO$_4$), and concentrated. The residue is chromatographed on silica gel (cyclohexane/ethyl acetate) to give the title compound. LC (method 4): $t_R$=1.24 min.

Intermediate 42

{(S)-6-[(R)-4-(8-Aza-bicyclo[3.2.1]oct-8-ylmethyl)-5-trifluoromethyl-indan-1-yloxy]-2,3-dihydro-benzofuran-3-yl}-acetic acid methyl ester

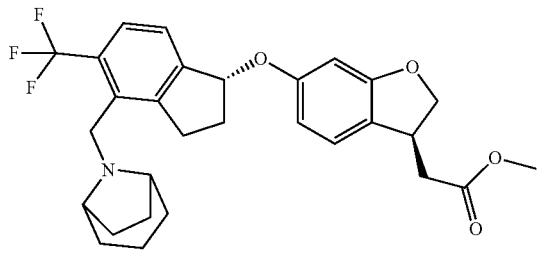 [SMILES: COC(=O)C[C@@H]1COc2cc(O[C@@H]3CCc4c3ccc(C(F)(F)F)c4CN3C4CCCC3CC4)ccc21]

8-Aza-bicyclo[3.2.1]octane (19 mg), KI (27 mg), and K$_2$CO$_3$ (45 mg) are added to a solution of {(S)-6-[(R)-4-bromomethyl-5-trifluoromethyl-indan-1-yloxy]-2,3-dihydro-benzofuran-3-yl}-acetic acid methyl ester (80 mg) in N,N-dimethylformamide (2 mL) at room temperature. The resulting mixture is stirred at room temperature overnight. Water and brine are added and the mixture is extracted with ethyl acetate. The combined extracts are dried (Na$_2$SO$_4$) and concentrated to give the crude title compound that is submitted to the next reaction step without further purification. LC (method 6): $t_R$=0.93 min; Mass spectrum (ESI$^+$): m/z=516 [M+H]$^+$.

Intermediate 43

{(S)-6-[(R)-4-(7,8-Dihydro-[1,6]naphthyridin-6-ylmethyl)-5-trifluoromethyl-indan-1-yloxy]-2,3-dihydro-benzofuran-3-yl}-acetic acid methyl ester

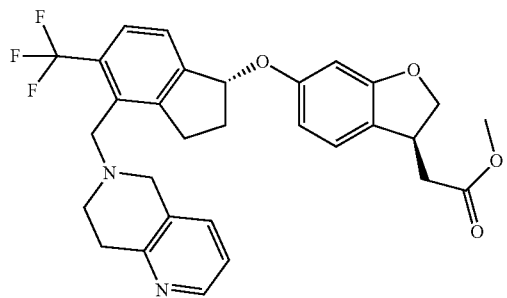

The title compound is prepared from {(S)-6-[(R)-4-bromomethyl-5-trifluoromethyl-indan-1-yloxy]-2,3-dihydro-benzofuran-3-yl}-acetic acid methyl ester and 7,8-dihydro-[1,6]naphthyridine following a procedure analogous to that described for Intermediate 42. LC (method 1): $t_R$=1.01 min; Mass spectrum (ESI$^+$): m/z=539 [M+H]$^+$.

Intermediate 44

{(S)-6-[(R)-4-(3,4-Dihydro-isoquinolin-2-ylmethyl)-5-trifluoromethyl-indan-1-yloxy]-2,3-dihydro-benzofuran-3-yl}-acetic acid methyl ester

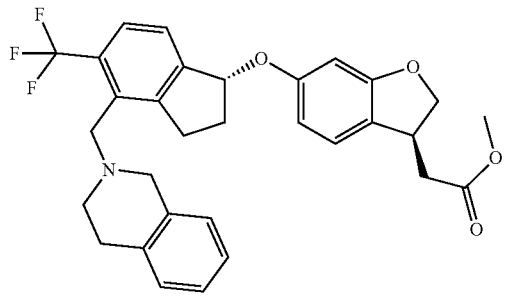 [SMILES: COC(=O)C[C@@H]1COc2cc(O[C@@H]3CCc4c3ccc(C(F)(F)F)c4CN3CCc4ncccc4C3)ccc21]

The title compound is prepared from {(S)-6-[(R)-4-bromomethyl-5-trifluoromethyl-indan-1-yloxy]-2,3-dihydro-benzofuran-3-yl}-acetic acid methyl ester and 3,4-dihydro-isoquinoline following a procedure analogous to that described for Intermediate 42. Mass spectrum (ESI$^+$): m/z=538 [M+H]$^+$.

Intermediate 45

{(S)-6-[(R)-4-(6,7-Dihydro-thiazolo[5,4-c]pyridin-5-ylmethyl)-5-trifluoromethyl-indan-1-yloxy]-2,3-dihydro-benzofuran-3-yl}-acetic acid methyl ester

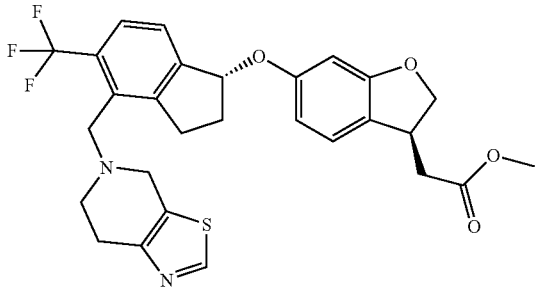 [SMILES: COC(=O)C[C@@H]1COc2cc(O[C@@H]3CCc4c3ccc(C(F)(F)F)c4CN3CCc4ncsc4C3)ccc21]

The title compound is prepared from {(S)-6-[(R)-4-bromomethyl-5-trifluoromethyl-indan-1-yloxy]-2,3-dihydro-benzofuran-3-yl}-acetic acid methyl ester and 4,5,6,7-tetrahydro-thiazolo[5,4-c]pyridine following a procedure analogous to that described for Intermediate 42. LC (method 1): $t_R$=1.16 min; Mass spectrum (ESI$^+$): m/z=545 [M+H]$^+$.

Intermediate 46

{(S)-6-[(R)-4-(2-Methyl-2,4,6,7-tetrahydro-pyrazolo[4,3-c]pyridin-5-ylmethyl)-5-trifluoromethyl-indan-1-yloxy]-2,3-dihydro-benzofuran-3-yl}-acetic acid methyl ester

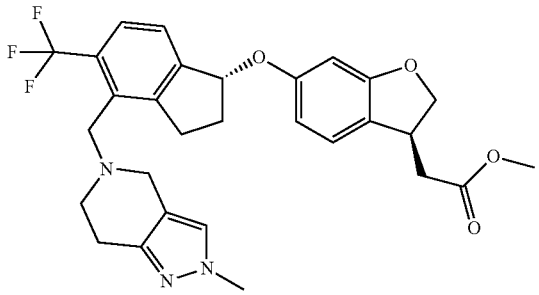 [SMILES: COC(=O)C[C@@H]1COc2cc(O[C@@H]3CCc4c3ccc(C(F)(F)F)c4CN3CCc4nn(C)cc4C3)ccc21]

The title compound is prepared from {(S)-6-[(R)-4-bromomethyl-5-trifluoromethyl-indan-1-yloxy]-2,3-dihydro-benzofuran-3-yl}-acetic acid methyl ester and 2-methyl-4,5,6,7-tetrahydro-2H-pyrazolo[4,3-c]pyridine following a procedure analogous to that described for Intermediate 42. LC (method 1): $t_R$=0.92 min; Mass spectrum (ESI$^+$): m/z=542 [M+H]$^+$.

Intermediate 47

7,8-Dihydro-pyrido[4,3-d]pyrimidin-6-yl)methyltrifluoroborate

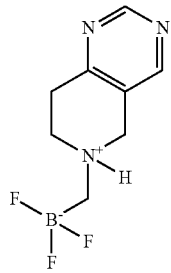

The title compound is prepared from potassium bromomethyltrifluoroborate and 5,6,7,8-tetrahydro-pyrido[4,3-d]pyrimidine following a procedure analogous to that described for Intermediate 8; the crude product is purified by chromatography on silica gel (dichloromethane/methanol). Mass spectrum (ESI$^-$): m/z=216 [M]$^-$.

Intermediate 48

{(S)-6-[(R)-4-(7,8-Dihydro-pyrido[4,3-d]pyrimidin-6-ylmethyl)-5-trifluoromethyl-indan-1-yloxy]-2,3-dihydro-benzofuran-3-yl}-acetic acid methyl ester

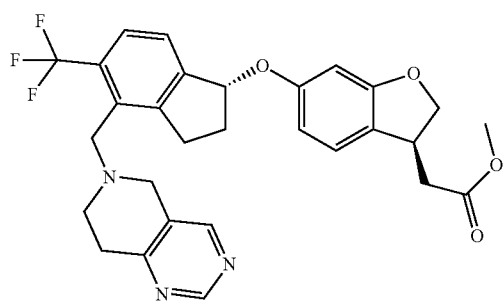 [SMILES: COC(=O)C[C@@H]1COc2cc(O[C@@H]3CCc4c3ccc(C(F)(F)F)c4CN3CCc4ncncc4C3)ccc21]

The title compound is prepared from {(S)-6-[(R)-4-bromomethyl-5-trifluoromethyl-indan-1-yloxy]-2,3-dihydro-benzofuran-3-yl}-acetic acid methyl ester and (7,8-dihydro-pyrido[4,3-d]pyrimidin-6-yl)methyltrifluoroborate following a procedure analogous to that described for Intermediate 3. LC (method 1): $t_R$=1.13 min; Mass spectrum (ESI$^+$): m/z=540 [M+H]$^+$.

Example 1

{(S)-6-[(R)-4-Morpholin-4-ylmethyl-5-trifluoromethyl-indan-1-yloxy]-2,3-dihydro-benzofuran-3-yl}-acetic acid

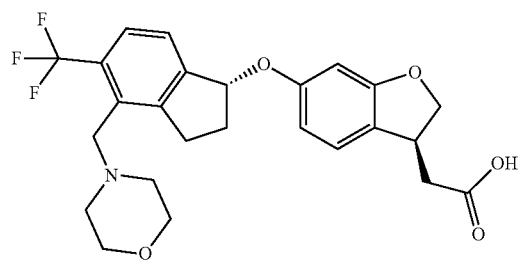 [SMILES: O=C(O)C[C@@H]1COc2cc(O[C@@H]3CCc4c3ccc(C(F)(F)F)c4CN3CCOCC3)ccc21]

4 M aqueous NaOH solution (0.20 mL) is added to a solution of {(S)-6-[(R)-4-morpholin-4-ylmethyl-5-trifluoromethyl-indan-1-yloxy]-2,3-dihydro-benzofuran-3-yl}-acetic acid methyl ester (91 mg) in methanol (1 mL) and tetrahydrofuran (1 mL) at room temperature. The mixture is stirred at room temperature for 3 h. The organic solvent is evaporated, water is added to the residue, and the resulting solution is neutralized with 1 M aqueous HCl solution. The solution is stirred at room temperature for 1 h. The precipitate formed is separated by filtration, washed with water, and dried to give the title compound (if the title compound does not precipitate, the solution is concentrated, and the residue is purified by HPLC on reversed phase using acetonitrile and water as eluent). LC (method 1): $t_R$=0.94 min; Mass spectrum (ESI$^+$): m/z=478 [M+H]$^+$.

Example 2

{(S)-6-[(R)-4-(4-tert-Butoxycarbonyl-piperazin-1-ylmethyl)-5-trifluoromethyl-indan-1-yloxy]-2,3-dihydro-benzofuran-3-yl}-acetic acid

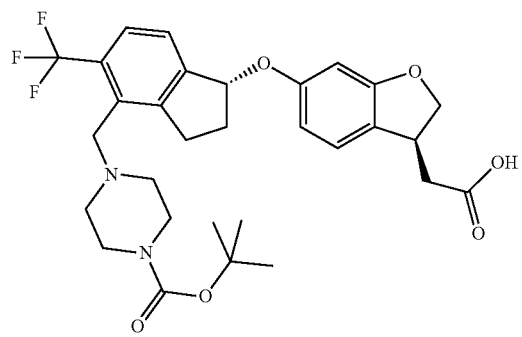 [SMILES: CC(C)(C)OC(=O)N1CCN(Cc2c(C(F)(F)F)ccc3c2CC[C@H]3Oc2ccc3c(c2)OC[C@H]3CC(=O)O)CC1]

The title compound is prepared from {(S)-6-[(R)-4-(4-tert-butoxycarbonyl-piperazin-1-ylmethyl)-5-trifluoromethyl-indan-1-yloxy]-2,3-dihydro-benzofuran-3-yl}-acetic acid methyl ester following a procedure analogous to that described for Example 1. LC (method 1): $t_R$=1.18 min; Mass spectrum (ESI−): m/z=575 [M−H]−.

Example 3

{(S)-6-[(R)-4-Thiomorpholin-4-ylmethyl-5-trifluoromethyl-indan-1-yloxy]-2,3-dihydro-benzofuran-3-yl}-acetic acid

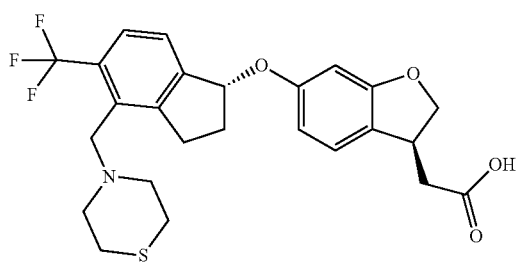 [SMILES: O=C(O)C[C@@H]1COc2cc(O[C@@H]3CCc4c3ccc(C(F)(F)F)c4CN3CCSCC3)ccc21]

The title compound is prepared from {(S)-6-[(R)-4-thiomorpholin-4-ylmethyl-5-trifluoromethyl-indan-1-yloxy]-2,3-dihydro-benzofuran-3-yl}-acetic acid methyl ester following a procedure analogous to that described for Example 1. LC (method 1): $t_R$=1.06 min; Mass spectrum (ESI+): m/z=494 [M+H]+.

Example 4

{(S)-6-[(R)-4-Pyrrolidin-1-ylmethyl-5-trifluoromethyl-indan-1-yloxy]-2,3-dihydro-benzofuran-3-yl}-acetic acid

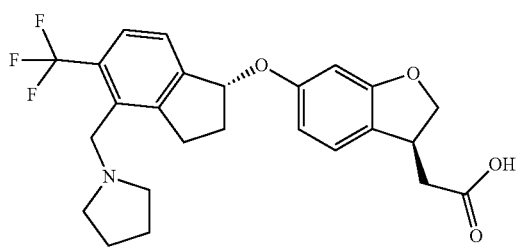 [SMILES: O=C(O)C[C@@H]1COc2cc(O[C@@H]3CCc4c3ccc(C(F)(F)F)c4CN3CCCC3)ccc21]

The title compound is prepared from {(S)-6-[(R)-4-pyrrolidin-1-ylmethyl-5-trifluoromethyl-indan-1-yloxy]-2,3-dihydro-benzofuran-3-yl}-acetic acid methyl ester following a procedure analogous to that described for Example 1. LC (method 1): $t_R$=0.84 min; Mass spectrum (ESI+): m/z=462 [M+H]+.

Example 5

{(S)-6-[(R)-4-Piperidin-1-ylmethyl-5-trifluoromethyl-indan-1-yloxy]-2,3-dihydro-benzofuran-3-yl}-acetic acid

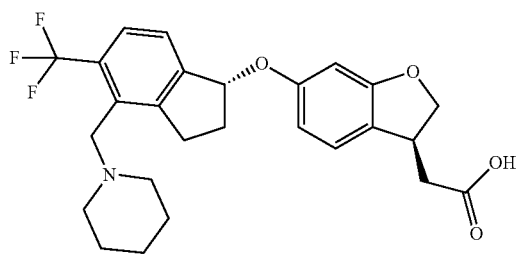 [SMILES: O=C(O)C[C@@H]1COc2cc(O[C@@H]3CCc4c3ccc(C(F)(F)F)c4CN3CCCCC3)ccc21]

The title compound is prepared from {(S)-6-[(R)-4-piperidin-1-ylmethyl-5-trifluoromethyl-indan-1-yloxy]-2,3-dihydro-benzofuran-3-yl}-acetic acid methyl ester following a procedure analogous to that described for Example 1. LC (method 4): $t_R$=0.86 min; Mass spectrum (ESI+): m/z=476 [M+H]+.

Example 6

{(S)-6-[(R)-4-(2-Methyl-4,5,6,7-tetrahydro-thiazolo[5,4-c]pyridin-5-ylmethyl)-5-trifluoromethyl-indan-1-yloxy]-2,3-dihydro-benzofuran-3-yl}-acetic acid

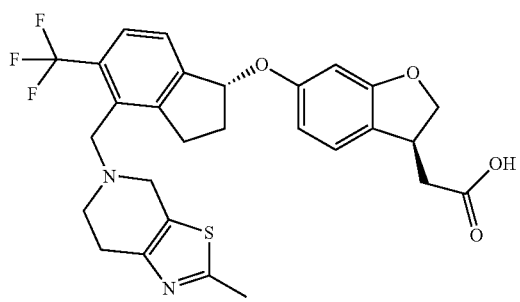 [SMILES: Cc1nc2c(s1)CN(Cc1c(C(F)(F)F)ccc3c1CC[C@H]3Oc1ccc3c(c1)OC[C@H]3CC(=O)O)CC2]

The title compound is prepared from {(S)-6-[(R)-4-(2-methyl-4,5,6,7-tetrahydro-thiazolo[5,4-c]pyridin-5-ylmethyl)-5-trifluoromethyl-indan-1-yloxy]-2,3-dihydro-benzofuran-3-yl}-acetic acid methyl ester following a procedure analogous to that described for Example 1. LC (method 6): $t_R$=0.91 min; Mass spectrum (ESI$^+$): m/z=545 [M+H]$^+$.

Example 7

{(S)-6-[(R)-4-(4,4-Difluoro-piperidin-1-ylmethyl)-5-trifluoromethyl-indan-1-yloxy]-2,3-dihydro-benzofuran-3-yl}-acetic acid

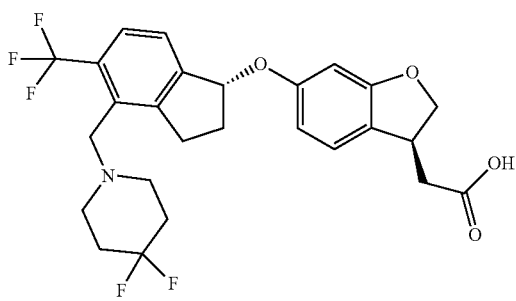 [SMILES: O=C(O)C[C@@H]1COc2cc(O[C@@H]3CCc4c3ccc(C(F)(F)F)c4CN3CCC(F)(F)CC3)ccc21]

The title compound is prepared from {(S)-6-[(R)-4-(4,4-difluoro-piperidin-1-ylmethyl)-5-trifluoromethyl-indan-1-yloxy]-2,3-dihydro-benzofuran-3-yl}-acetic acid methyl ester following a procedure analogous to that described for Example 1. LC (method 1): $t_R$=1.19 min; Mass spectrum (ESI$^+$): m/z=512 [M+H]$^+$.

Example 8

{(S)-6-[(R)-4-(6-Aza-spiro[2.5]oct-6-ylmethyl)-5-trifluoromethyl-indan-1-yloxy]-2,3-dihydro-benzofuran-3-yl}-acetic acid

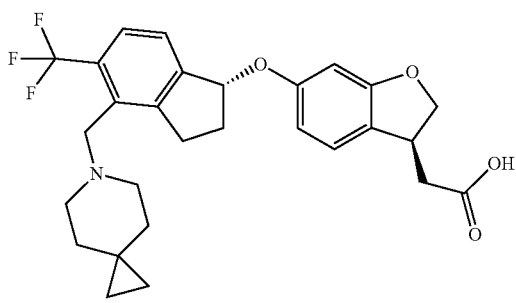 [SMILES: O=C(O)C[C@@H]1COc2cc(O[C@@H]3CCc4c3ccc(C(F)(F)F)c4CN3CCC4(CC3)CC4)ccc21]

The title compound is prepared from {(S)-6-[(R)-4-(6-aza-spiro[2.5]oct-6-ylmethyl)-5-trifluoromethyl-indan-1-yloxy]-2,3-dihydro-benzofuran-3-yl}-acetic acid methyl ester following a procedure analogous to that described for Example 1. LC (method 1): $t_R$=0.87 min; Mass spectrum (ESI$^+$): m/z=502 [M+H]$^+$.

Example 9

{(S)-6-[(R)-[1,4]Oxazepan-4-ylmethyl-5-trifluoromethyl-indan-1-yloxy]-2,3-dihydro-benzofuran-3-yl}-acetic acid

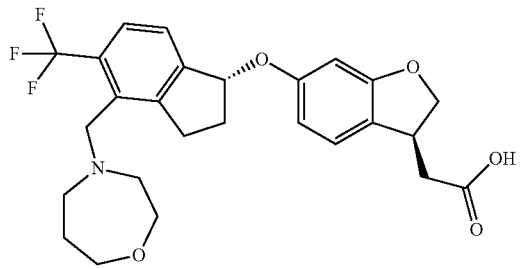 [SMILES: O=C(O)C[C@@H]1COc2cc(O[C@@H]3CCc4c3ccc(C(F)(F)F)c4CN3CCCOCC3)ccc21]

The title compound is prepared from {(S)-6-[(R)-4-[1,4]oxazepan-4-ylmethyl-5-trifluoromethyl-indan-1-yloxy]-2,3-dihydro-benzofuran-3-yl}-acetic acid methyl ester following a procedure analogous to that described for Example 1. LC (method 1): $t_R$=0.85 min; Mass spectrum (ESI$^+$): m/z=492 [M+H]$^+$.

Example 10

{(S)-6-[(R)-4-(4-Methoxy-piperidin-1-ylmethyl)-5-trifluoromethyl-indan-1-yloxy]-2,3-dihydro-benzofuran-3-yl}-acetic acid

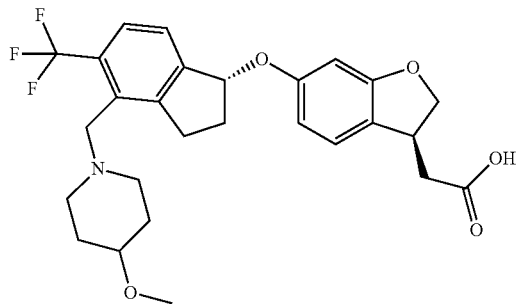 [SMILES: COC1CCN(Cc2c(C(F)(F)F)ccc3c2CC[C@H]3Oc2ccc3c(c2)OC[C@H]3CC(=O)O)CC1]

The title compound is prepared from {(S)-6-[(R)-4-(4-methoxy-piperidin-1-ylmethyl)-5-trifluoromethyl-indan-1-yloxy]-2,3-dihydro-benzofuran-3-yl}-acetic acid methyl ester following a procedure analogous to that described for Example 1. Mass spectrum (ESI$^+$): m/z=506 [M+H]$^+$.

Example 11

{(S)-6-[(R)-4-(1-Oxa-8-aza-spiro[4.5]dec-8-ylmethyl)-5-trifluoromethyl-indan-1-yloxy]-2,3-dihydro-benzofuran-3-yl}-acetic acid

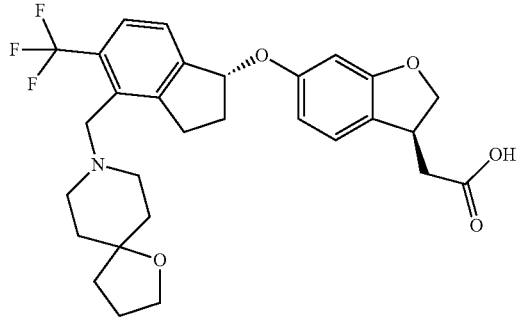 [SMILES: O=C(O)C[C@@H]1COc2cc(O[C@@H]3CCc4c3ccc(C(F)(F)F)c4CN3CCC4(CCCO4)CC3)ccc21]

The title compound is prepared from {(S)-6-[(R)-4-(1-oxa-8-aza-spiro[4.5]dec-8-ylmethyl)-5-trifluoromethyl-indan-1-yloxy]-2,3-dihydro-benzofuran-3-yl}-acetic acid methyl ester following a procedure analogous to that described for Example 1. LC (method 1): $t_R$=0.87 min; Mass spectrum (ESI$^+$): m/z=532 [M+H]$^+$.

Example 12

{(S)-6-[(R)-4-(3-Aza-bicyclo[3.1.0]hex-3-ylmethyl)-5-trifluoromethyl-indan-1-yloxy]-2,3-dihydro-benzofuran-3-yl}-acetic acid

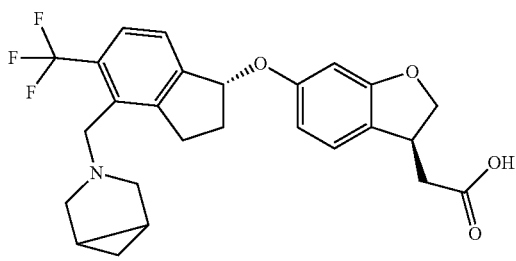 [SMILES: O=C(O)C[C@@H]1COc2cc(O[C@@H]3CCc4c3ccc(C(F)(F)F)c4CN3CC4CC4C3)ccc21]

The title compound is prepared from {(S)-6-[(R)-4-(3-aza-bicyclo[3.1.0]hex-3-ylmethyl)-5-trifluoromethyl-indan-1-yloxy]-2,3-dihydro-benzofuran-3-yl}-acetic acid methyl ester following a procedure analogous to that described for Example 1. LC (method 1): $t_R$=0.89 min; Mass spectrum (ESI$^+$): m/z=474 [M+H]$^+$.

Example 13

{(S)-6-[(R)-4-(4-Hydroxymethyl-piperidin-1-ylmethyl)-5-trifluoromethyl-indan-1-yloxy]-2,3-dihydro-benzofuran-3-yl}-acetic acid

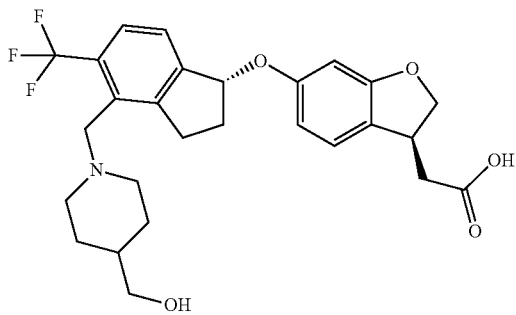 [SMILES: O=C(O)C[C@@H]1COc2cc(O[C@@H]3CCc4c3ccc(C(F)(F)F)c4CN3CCC(CO)CC3)ccc21]

The title compound is prepared from {(S)-6-[(R)-4-(4-hydroxymethyl-piperidin-1-ylmethyl)-5-trifluoromethyl-indan-1-yloxy]-2,3-dihydro-benzofuran-3-yl}-acetic acid methyl ester following a procedure analogous to that described for Example 1. LC (method 1): $t_R$=0.85 min; Mass spectrum (ESI$^+$): m/z=506 [M+H]$^+$.

Example 14

{(S)-6-[(R)-4-(4-Hydroxy-4-methyl-piperidin-1-ylmethyl)-5-trifluoromethyl-indan-1-yloxy]-2,3-dihydro-benzofuran-3-yl}-acetic acid

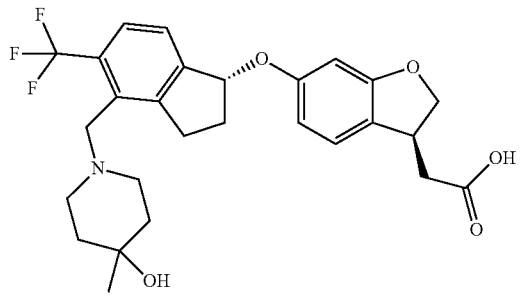 [SMILES: CC1(O)CCN(Cc2c(C(F)(F)F)ccc3c2CC[C@H]3Oc2ccc3c(c2)OC[C@H]3CC(=O)O)CC1]

The title compound is prepared from {(S)-6-[(R)-4-(4-hydroxy-4-methyl-piperidin-1-ylmethyl)-5-trifluoromethyl-indan-1-yloxy]-2,3-dihydro-benzofuran-3-yl}-acetic acid methyl ester following a procedure analogous to that described for Example 1. LC (method 1): $t_R$=0.78 min; Mass spectrum (ESI$^+$): m/z=506 [M+H]$^+$.

Example 15

{(S)-6-[(R)-4-piperazin-1-ylmethyl-5-trifluoromethyl-indan-1-yloxy]-2,3-dihydro-benzofuran-3-yl}-acetic acid

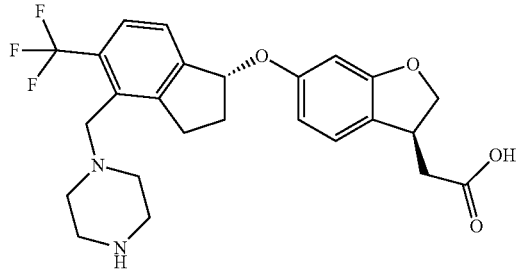 [SMILES: O=C(O)C[C@@H]1COc2cc(O[C@@H]3CCc4c3ccc(C(F)(F)F)c4CN3CCNCC3)ccc21]

The title compound is prepared from {(S)-6-[(R)-4-piperazin-1-ylmethyl-5-trifluoromethyl-indan-1-yloxy]-2,3-dihydro-benzofuran-3-yl}-acetic acid methyl ester following a procedure analogous to that described for Example 1. LC (method 4): $t_R$=0.91 min; Mass spectrum (ESI$^+$): m/z=477 [M+H]$^+$.

Example 16

{(S)-6-[(R)-4-(4-Acetyl-piperazin-1-ylmethyl)-5-trifluoromethyl-indan-1-yloxy]-2,3-dihydro-benzofuran-3-yl}-acetic acid

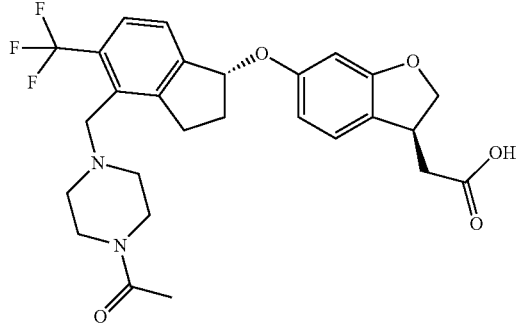 [SMILES: CC(=O)N1CCN(Cc2c(C(F)(F)F)ccc3c2CC[C@H]3Oc2ccc3c(c2)OC[C@H]3CC(=O)O)CC1]

Acetic anhydride (0.03 mL) is added to a solution of {(S)-6-[(R)-4-piperazin-1-ylmethyl-5-trifluoromethyl-indan-1-yloxy]-2,3-dihydro-benzofuran-3-yl}-acetic acid (0.22 g) and N,N-diisopropyl-ethylamine (0.11 mL) in acetonitrile (5 mL) at room temperature. The solution is stirred at room temperature for 1.5 h. 4 M aqueous NaOH solution (0.1 mL) is added and the solution is stirred for another 30 min. Water is added and the resulting solution is acidified with 4 M HCl solution (pH ca. 3-4). The resulting mixture is extracted with ethyl acetate, and the combined extracts are washed with brine and dried ($Na_2SO_4$). The solvent is evaporated and the residue is chromatographed on silica gel (cyclohexane/ethyl acetate) to give the title compound. LC (method 1): $t_R$=0.95 min; Mass spectrum (ESI$^+$): m/z=519 [M+H]$^+$.

Example 17

{(S)-6-[(R)-4-(4-Methoxycarbonyl-piperazin-1-ylmethyl)-5-trifluoromethyl-indan-1-yloxy]-2,3-dihydro-benzofuran-3-yl}-acetic acid

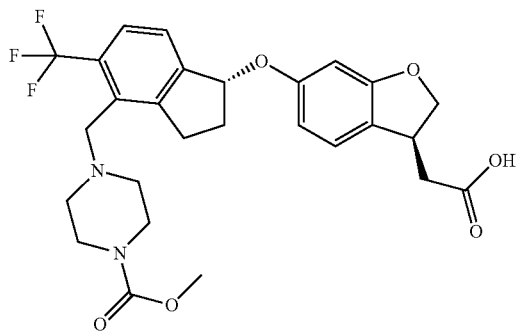 [SMILES: COC(=O)N1CCN(Cc2c(C(F)(F)F)ccc3c2CC[C@H]3Oc2ccc3c(c2)OC[C@H]3CC(=O)O)CC1]

The title compound is prepared from {(S)-6-[(R)-4-(4-methoxycarbonyl-piperazin-1-ylmethyl)-5-trifluoromethyl-indan-1-yloxy]-2,3-dihydro-benzofuran-3-yl}-acetic acid methyl ester following a procedure analogous to that described for Example 1. LC (method 4): $t_R$=0.90 min; Mass spectrum (ESI$^+$): m/z=535 [M+H]$^+$.

Example 18

{(S)-6-[(R)-4-(cis-2,6-Dimethyl-morpholin-4-ylmethyl)-5-trifluoromethyl-indan-1-yloxy]-2,3-dihydro-benzofuran-3-yl}-acetic acid

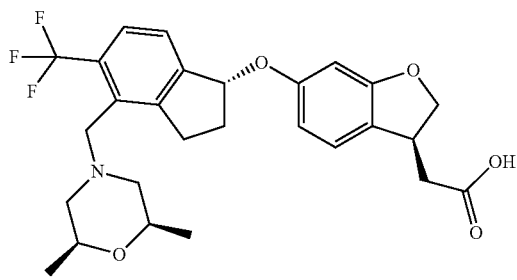 [SMILES: C[C@@H]1CN(Cc2c(C(F)(F)F)ccc3c2CC[C@H]3Oc2ccc3c(c2)OC[C@H]3CC(=O)O)C[C@H](C)O1]

The title compound is prepared from {(S)-6-[(R)-4-(cis-2,6-dimethyl-morpholin-4-ylmethyl)-5-trifluoromethyl-indan-1-yloxy]-2,3-dihydro-benzofuran-3-yl}-acetic acid methyl ester following a procedure analogous to that described for Example 1. LC (method 1): $t_R$=1.06 min; Mass spectrum (ESI$^+$): m/z=506 [M+H]$^+$.

Example 19

{(S)-6-[(R)-4-Azepan-1-ylmethyl-5-trifluoromethyl-indan-1-yloxy]-2,3-dihydro-benzofuran-3-yl}-acetic acid

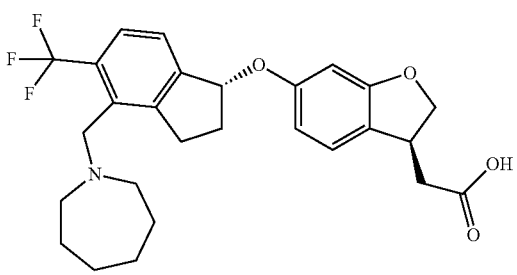 [SMILES: O=C(O)C[C@@H]1COc2cc(O[C@@H]3CCc4c3ccc(C(F)(F)F)c4CN3CCCCCC3)ccc21]

The title compound is prepared from {(S)-6-[(R)-4-azepan-1-ylmethyl-5-trifluoromethyl-indan-1-yloxy]-2,3-dihydro-benzofuran-3-yl}-acetic acid methyl ester following a procedure analogous to that described for Example 1. LC (method 3): $t_R$=0.95 min; Mass spectrum (ESI$^+$): m/z=490 [M+H]$^+$.

Example 20

{(S)-6-[(R)-4-(4-Ethoxycarbonyl-piperazin-1-ylmethyl)-5-trifluoromethyl-indan-1-yloxy]-2,3-dihydro-benzofuran-3-yl}-acetic acid

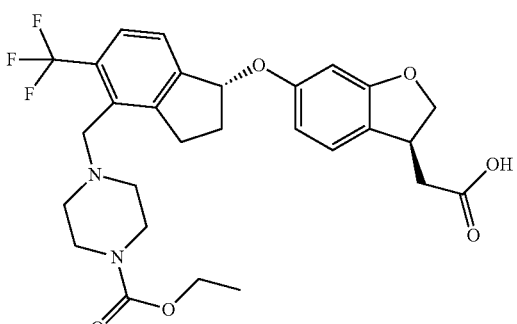

The title compound is prepared from {(S)-6-[(R)-4-(4-ethoxycarbonyl-piperazin-1-ylmethyl)-5-trifluoromethyl-indan-1-yloxy]-2,3-dihydro-benzofuran-3-yl}-acetic acid methyl ester following a procedure analogous to that described for Example 1. LC (method 4): $t_R$=0.94 min; Mass spectrum (ESI$^+$): m/z=549 [M+H]$^+$.

Example 21

{(S)-6-[(R)-4-(4-Propionyl-piperazin-1-ylmethyl)-5-trifluoromethyl-indan-1-yloxy]-2,3-dihydro-benzofuran-3-yl}-acetic acid

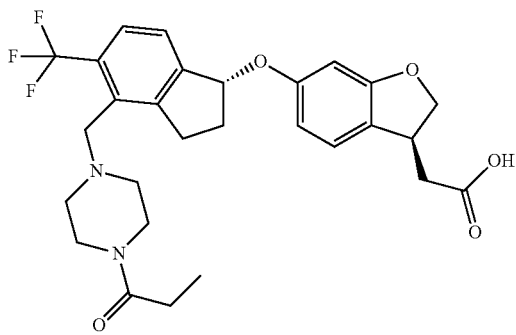 [SMILES: CCC(=O)N1CCN(Cc2c(C(F)(F)F)ccc3c2CC[C@H]3Oc2ccc3c(c2)OC[C@H]3CC(=O)O)CC1]

The title compound is prepared from {(S)-6-[(R)-4-(4-propionyl-piperazin-1-ylmethyl)-5-trifluoromethyl-indan-1-yloxy]-2,3-dihydro-benzofuran-3-yl}-acetic acid methyl ester following a procedure analogous to that described for Example 1. LC (method 4): $t_R$=0.87 min; Mass spectrum (ESI$^+$): m/z=533 [M+H]$^+$.

Example 22

{(S)-6-[(R)-4-(4-Isopropoxycarbonyl-piperazin-1-ylmethyl)-5-trifluoromethyl-indan-1-yloxy]-2,3-dihydro-benzofuran-3-yl}-acetic acid

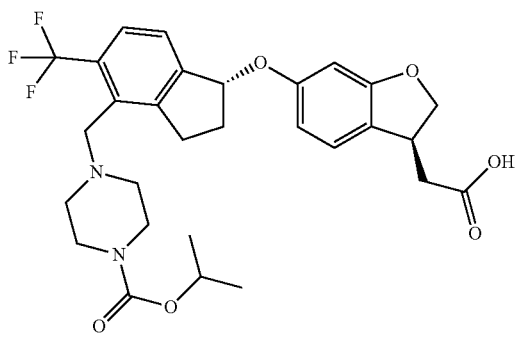 [SMILES: CC(C)OC(=O)N1CCN(Cc2c(C(F)(F)F)ccc3c2CC[C@H]3Oc2ccc3c(c2)OC[C@H]3CC(=O)O)CC1]

The title compound is prepared from {(S)-6-[(R)-4-(4-isopropoxycarbonyl-piperazin-1-ylmethyl)-5-trifluoromethyl-indan-1-yloxy]-2,3-dihydro-benzofuran-3-yl}-acetic acid methyl ester following a procedure analogous to that described for Example 1. LC (method 4): $t_R$=0.96 min; Mass spectrum (ESI$^+$): m/z=563 [M+H]$^+$.

Example 23

{(S)-6-[(R)-4-(2,2-Dimethyl-morpholin-4-ylmethyl)-5-trifluoromethyl-indan-1-yloxy]-2,3-dihydro-benzofuran-3-yl}-acetic acid

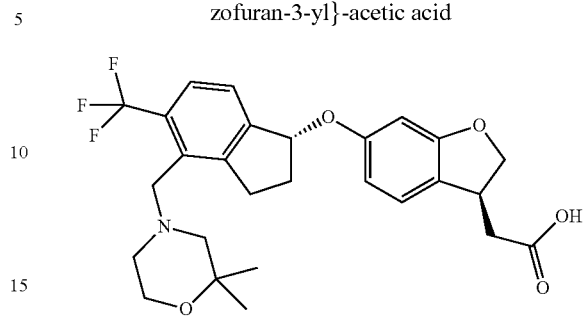

The title compound is prepared from {(S)-6-[(R)-4-(2,2-dimethyl-morpholin-4-ylmethyl)-5-trifluoromethyl-indan-1-yloxy]-2,3-dihydro-benzofuran-3-yl}-acetic acid methyl ester following a procedure analogous to that described for Example 1. LC (method 8): $t_R$=0.80 min; Mass spectrum (ESI$^+$): m/z=506 [M+H]$^+$.

Example 24

{(S)-6-[(R)-4-(8-Oxa-3-aza-bicyclo[3.2.1]oct-3-ylmethyl)-5-trifluoromethyl-indan-1-yloxy]-2,3-dihydro-benzofuran-3-yl}-acetic acid

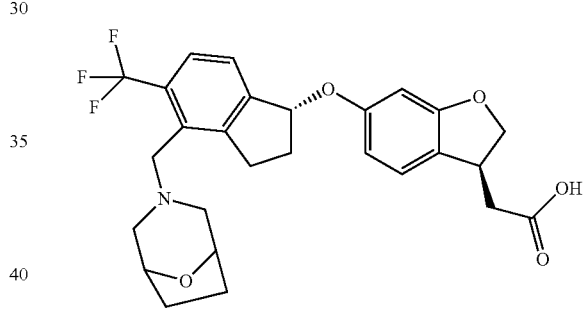

The title compound is prepared from {(S)-6-[(R)-4-(8-oxa-3-aza-bicyclo[3.2.1]oct-3-ylmethyl)-5-trifluoromethyl-indan-1-yloxy]-2,3-dihydro-benzofuran-3-yl}-acetic acid methyl ester following a procedure analogous to that described for Example 1. LC (method 4): $t_R$=1.15 min; Mass spectrum (ESI$^+$): m/z=504 [M+H]$^+$.

Example 25

{(S)-6-[(R)-4-(8-Aza-bicyclo[3.2.1]oct-8-ylmethyl)-5-trifluoromethyl-indan-1-yloxy]-2,3-dihydro-benzofuran-3-yl}-acetic acid

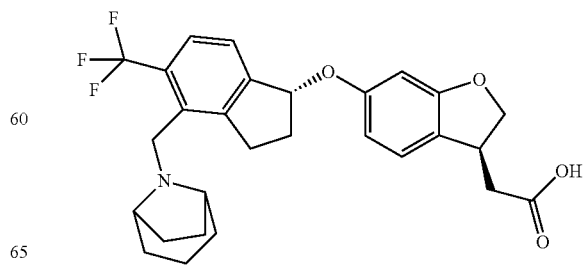

The title compound is prepared from {(S)-6-[(R)-4-(8-aza-bicyclo[3.2.1]oct-8-ylmethyl)-5-trifluoromethyl-indan-1-yloxy]-2,3-dihydro-benzofuran-3-yl}-acetic acid methyl ester following a procedure analogous to that described for Example 1. LC (method 4): $t_R$=0.90 min; Mass spectrum (ESI$^+$): m/z=502 [M+H]$^+$.

Example 26

{(S)-6-[(R)-4-(4-Methyl-3-oxo-piperazin-1-ylmethyl)-5-trifluoromethyl-indan-1-yloxy]-2,3-dihydro-benzofuran-3-yl}-acetic acid

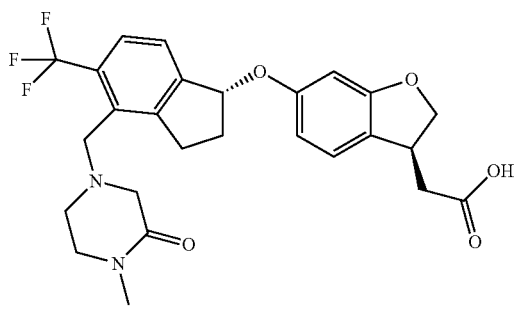 [SMILES: CN1CCN(Cc2c(C(F)(F)F)ccc3c2CC[C@H]3Oc2ccc3c(c2)OC[C@H]3CC(=O)O)CC1=O]

The methyl ester of the title compound, {(S)-6-[(R)-4-(4-methyl-3-oxo-piperazin-1-ylmethyl)-5-trifluoromethyl-indan-1-yloxy]-2,3-dihydro-benzofuran-3-yl}-acetic acid methyl ester, is prepared from {(S)-6-[(R)-4-bromomethyl-5-trifluoromethyl-indan-1-yloxy]-2,3-dihydro-benzofuran-3-yl}-acetic acid methyl ester and 1-methyl-piperazin-2-one following a procedure analogous to that described for Intermediate 42. The crude product is directly submitted to the saponification conditions described for Example 1 to give the title compound upon chromatography on reversed phase (HPLC; acetonitrile/water). LC (method 6): $t_R$=1.03 min; Mass spectrum (ESI$^+$): m/z=505 [M+H]$^+$.

Example 27

{(S)-6-[(R)-4-(5,6-Dihydro-8H-imidazo[1,2-a]pyrazin-7-ylmethyl)-5-trifluoromethyl-indan-1-yloxy]-2,3-dihydro-benzofuran-3-yl}-acetic acid

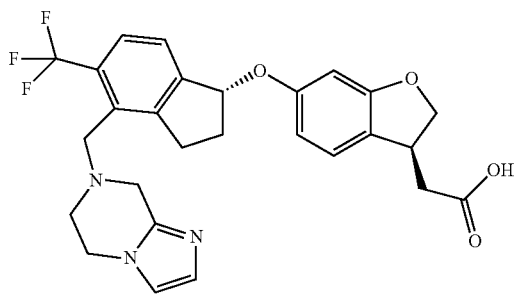 [SMILES: O=C(O)C[C@@H]1COc2cc(O[C@@H]3CCc4c3ccc(C(F)(F)F)c4CN3CCn4ccnc4C3)ccc21]

The methyl ester of the title compound, {(S)-6-[(R)-4-(5,6-dihydro-8H-imidazo[1,2-a]pyrazin-7-ylmethyl)-5-trifluoromethyl-indan-1-yloxy]-2,3-dihydro-benzofuran-3-yl}-acetic acid methyl ester, is prepared from {(S)-6-[(R)-4-bromomethyl-5-trifluoromethyl-indan-1-yloxy]-2,3-dihydro-benzofuran-3-yl}-acetic acid methyl ester and 5,6,7,8-tetrahydro-imidazo[1,2-a]pyrazine following a procedure analogous to that described for Intermediate 42. The crude product is directly submitted to the saponification conditions described for Example 1 to give the title compound upon chromatography on reversed phase (HPLC; acetonitrile/water). LC (method 6): $t_R$=0.76 min; Mass spectrum (ESI$^+$): m/z=514 [M+H]$^+$.

Example 28

{(S)-6-[(R)-4-(7,8-Dihydro-[1,6]naphthyridin-6-ylmethyl)-5-trifluoromethyl-indan-1-yloxy]-2,3-dihydro-benzofuran-3-yl}-acetic acid

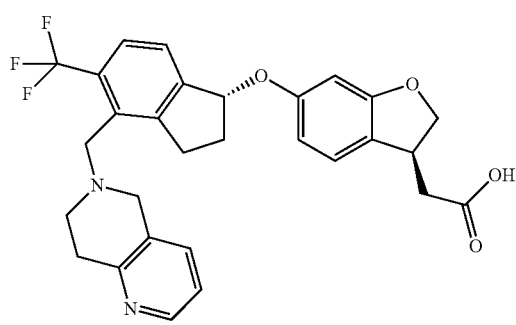 [SMILES: O=C(O)C[C@@H]1COc2cc(O[C@@H]3CCc4c3ccc(C(F)(F)F)c4CN3CCc4ncccc4C3)ccc21]

The title compound is prepared from {(S)-6-[(R)-4-(7,8-dihydro-[1,6]naphthyridin-6-ylmethyl)-5-trifluoromethyl-indan-1-yloxy]-2,3-dihydro-benzofuran-3-yl}-acetic acid methyl ester following a procedure analogous to that described for Example 1. LC (method 1): $t_R$=0.93 min; Mass spectrum (ESI$^+$): m/z=525 [M+H]$^+$.

Example 29

{(S)-6-[(R)-4-(3,4-Dihydro-isoquinolin-2-ylmethyl)-5-trifluoromethyl-indan-1-yloxy]-2,3-dihydro-benzofuran-3-yl}-acetic acid

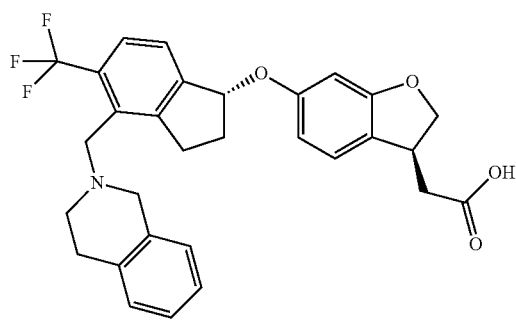 [SMILES: O=C(O)C[C@@H]1COc2cc(O[C@@H]3CCc4c3ccc(C(F)(F)F)c4CN3CCc4ccccc4C3)ccc21]

The title compound is prepared from {(S)-6-[(R)-4-(3,4-dihydro-isoquinolin-2-ylmethyl)-5-trifluoromethyl-indan-1-yloxy]-2,3-dihydro-benzofuran-3-yl}-acetic acid methyl ester following a procedure analogous to that described for Example 1. LC (method 1): $t_R$=1.01 min; Mass spectrum (ESI$^+$): m/z=524 [M+H]$^+$.

Example 30

{(S)-6-[(R)-4-(6,7-Dihydro-thiazolo[5,4-c]pyridin-5-ylmethyl)-5-trifluoromethyl-indan-1-yloxy]-2,3-dihydro-benzofuran-3-yl}-acetic acid

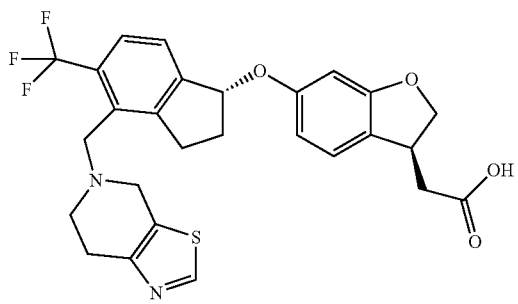 [SMILES: O=C(O)C[C@@H]1COc2cc(O[C@@H]3CCc4c3ccc(C(F)(F)F)c4CN3CCc4ncsc4C3)ccc21]

The title compound is prepared from {(S)-6-[(R)-4-(6,7-dihydro-thiazolo[5,4-c]pyridin-5-ylmethyl)-5-trifluoromethyl-indan-1-yloxy]-2,3-dihydro-benzofuran-3-yl}-acetic acid methyl ester following a procedure analogous to that described for Example 1. LC (method 1): $t_R$=1.06 min; Mass spectrum (ESI$^+$): m/z=531 [M+H]$^+$.

Example 31

{(S)-6-[(R)-4-(2-Methyl-2,4,6,7-tetrahydro-pyrazolo[4,3-c]pyridin-5-ylmethyl)-5-trifluoromethyl-indan-1-yloxy]-2,3-dihydro-benzofuran-3-yl}-acetic acid

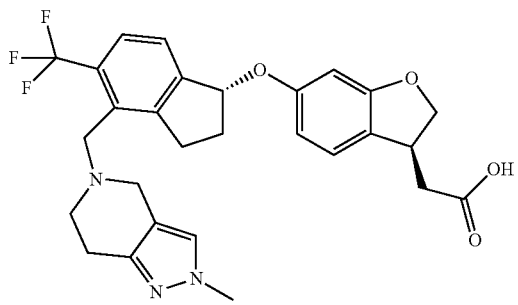 [SMILES: Cn1cc2c(n1)CCN(Cc1c(C(F)(F)F)ccc3c1CC[C@H]3Oc1ccc3c(c1)OC[C@H]3CC(=O)O)C2]

The title compound is prepared from {(S)-6-[(R)-4-(2-methyl-2,4,6,7-tetrahydro-pyrazolo[4,3-c]pyridin-5-ylmethyl)-5-trifluoromethyl-indan-1-yloxy]-2,3-dihydro-benzofuran-3-yl}-acetic acid methyl ester following a procedure analogous to that described for Example 1. LC (method 1): $t_R$=0.83 min; Mass spectrum (ESI$^+$): m/z=528 [M+H]$^+$.

Example 32

{(S)-6-[(R)-4-(4,7-Dihydro-thieno[2,3-c]pyridin-6-ylmethyl)-5-trifluoromethyl-indan-1-yloxy]-2,3-dihydro-benzofuran-3-yl}-acetic acid

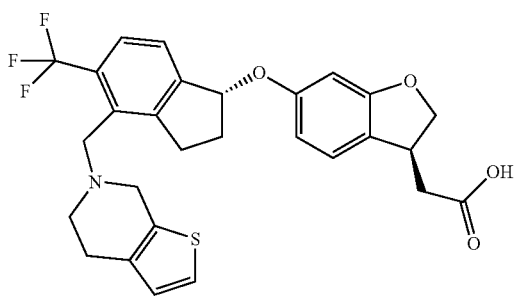 [SMILES: O=C(O)C[C@@H]1COc2cc(O[C@@H]3CCc4c3ccc(C(F)(F)F)c4CN3CCc4ccsc4C3)ccc21]

The methyl ester of the title compound, {(S)-6-[(R)-4-(4,7-dihydro-thieno[2,3-c]pyridin-6-ylmethyl)-5-trifluoromethyl-indan-1-yloxy]-2,3-dihydro-benzofuran-3-yl}-acetic acid methyl ester, is prepared from {(S)-6-[(R)-4-bromomethyl-5-trifluoromethyl-indan-1-yloxy]-2,3-dihydro-benzofuran-3-yl}-acetic acid methyl ester and 4,5,6,7-tetrahydro-thieno[2,3-c]pyridine following a procedure analogous to that described for Intermediate 42. The crude product is directly submitted to the saponification conditions described for Example 1 to give the title compound upon chromatography on reversed phase (HPLC; acetonitrile/water). LC (method 6): $t_R$=0.91 min; Mass spectrum (ESI$^+$): m/z=530 [M+H]$^+$.

Example 33

{(S)-6-[(R)-4-(6,7-Dihydro-pyrazolo[1,5-a]pyrazin-5-ylmethyl)-5-trifluoromethyl-indan-1-yloxy]-2,3-dihydro-benzofuran-3-yl}-acetic acid

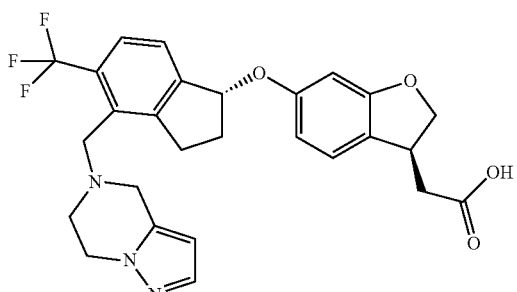

The methyl ester of the title compound, {(S)-6-[(R)-4-(6,7-dihydro-pyrazolo[1,5-a]pyrazin-5-ylmethyl)-5-trifluoromethyl-indan-1-yloxy]-2,3-dihydro-benzofuran-3-yl}-acetic acid methyl ester, is prepared from {(S)-6-[(R)-4-bromomethyl-5-trifluoromethyl-indan-1-yloxy]-2,3-dihydro-benzofuran-3-yl}-acetic acid methyl ester and 4,5,6,7-tetrahydro-pyrazolo[1,5-a]pyrazine following a procedure analogous to that described for Intermediate 42. The crude product is directly submitted to the saponification conditions described for Example 1 to give the title compound upon chromatography on reversed phase (HPLC; acetonitrile/water). LC (method 6): $t_R$=1.07 min; Mass spectrum (ESI⁺): m/z=514 [M+H]⁺.

Example 34

{(S)-6-[(R)-4-(6,7-Dihydro-isoxazolo[4,3-c]pyridin-5-ylmethyl)-5-trifluoromethyl-indan-1-yloxy]-2,3-dihydro-benzofuran-3-yl}-acetic acid

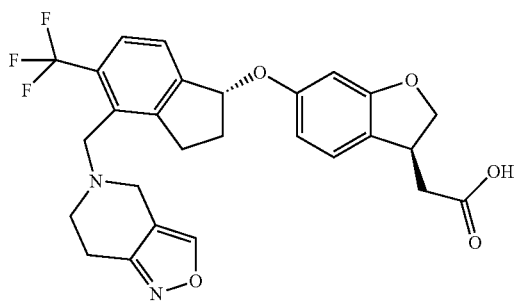 [SMILES: O=C(O)C[C@@H]1COc2cc(O[C@@H]3CCc4c3ccc(C(F)(F)F)c4CN3CCc4nocc4C3)ccc21]

The methyl ester of the title compound, {(S)-6-[(R)-4-(6,7-dihydro-isoxazolo[4,3-c]pyridin-5-ylmethyl)-5-trifluoromethyl-indan-1-yloxy]-2,3-dihydro-benzofuran-3-yl}-acetic acid methyl ester, is prepared from {(S)-6-[(R)-4-bromomethyl-5-trifluoromethyl-indan-1-yloxy]-2,3-dihydro-benzofuran-3-yl}-acetic acid methyl ester and 4,5,6,7-tetrahydro-isoxazolo[4,3-c]pyridine following a procedure analogous to that described for Intermediate 42. The crude product is directly submitted to the saponification conditions described for Example 1 to give the title compound upon chromatography on reversed phase (HPLC; acetonitrile/water). LC (method 6): $t_R$=0.94 min; Mass spectrum (ESI⁺): m/z=515 [M+H]⁺.

Example 35

{(S)-6-[(R)-4-(2-Methyl-6,7-dihydro-oxazolo[4,5-c]pyridin-5-ylmethyl)-5-trifluoromethyl-indan-1-yloxy]-2,3-dihydro-benzofuran-3-yl}-acetic acid

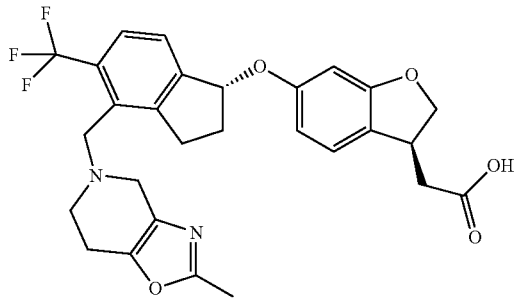 [SMILES: Cc1nc2c(o1)CCN(Cc1c(C(F)(F)F)ccc3c1CC[C@H]3Oc1ccc3c(c1)OC[C@H]3CC(=O)O)C2]

The methyl ester of the title compound, {(S)-6-[(R)-4-(2-methyl-6,7-dihydro-oxazolo[4,5-c]pyridin-5-ylmethyl)-5-trifluoromethyl-indan-1-yloxy]-2,3-dihydro-benzofuran-3-yl}-acetic acid methyl ester, is prepared from {(S)-6-[(R)-4-bromomethyl-5-trifluoromethyl-indan-1-yloxy]-2,3-dihydro-benzofuran-3-yl}-acetic acid methyl ester and 2-methyl-4,5,6,7-tetrahydro-oxazolo[4,5-c]pyridine following a procedure analogous to that described for Intermediate 42. The crude product is directly submitted to the saponification conditions described for Example 1 to give the title compound upon chromatography on reversed phase (HPLC;

acetonitrile/water). LC (method 6): $t_R$=0.89 min; Mass spectrum (ESI⁺): m/z=529 [M+H]⁺.

Example 36

{(S)-6-[(R)-4-(7,8-Dihydro-5H-pyrido[4,3-d]pyrimidin-6-ylmethyl)-5-trifluoromethyl-indan-1-yloxy]-2,3-dihydro-benzofuran-3-yl}-acetic acid

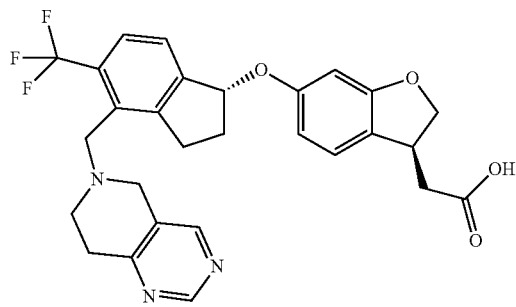 [SMILES: O=C(O)C[C@@H]1COc2cc(O[C@@H]3CCc4c3ccc(C(F)(F)F)c4CN3CCc4ncncc4C3)ccc21]

The title compound is prepared from {(S)-6-[(R)-4-(7,8-dihydro-5H-pyrido[4,3-d]pyrimidin-6-ylmethyl)-5-trifluoromethyl-indan-1-yloxy]-2,3-dihydro-benzofuran-3-yl}-acetic acid methyl ester following a procedure analogous to that described for Example 1. LC (method 4): $t_R$=0.93 min; Mass spectrum (ESI⁺): m/z=526 [M+H]⁺.

The invention claimed is:
1. A compound of formula I

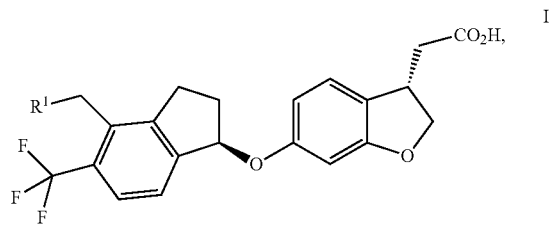

wherein:
$R^1$ is selected from the group consisting of a monocyclic or bicyclic group having 5 to 12 ring member atoms of which 4 to 11 ring members are C atoms and 1 to 3 ring members are heteroatoms selected from N and $NR^N$, or 1 or 2 ring members are heteroatoms selected from N and $NR^N$ and 1 ring member is selected from O and S, or 1 ring member is N and 2 ring members are independently selected from O and S, with the proviso that no O—O, S—S, or S—O bond is formed,
wherein the ring member atom attached to the —CH₂— group in formula I is a N atom, 1 CH₂ ring member attached to a ring member N atom is optionally replaced by a —C(=O)— group, the monocyclic or bicyclic group is saturated or partially unsaturated, with the proviso that in bicyclic groups the ring attached to the —CH₂— group in formula I is not aromatic, and the bicyclic group is optionally a fused, bridged, or spiro ring system, and any of these groups is optionally and independently substituted with 1 to 3 $R^2$ groups;
$R^2$ is F, Cl, Br, I, $C_{1-4}$-alkyl, NC—, HO—$C_{1-4}$-alkyl, HO—, $C_{1-4}$-alkyl-O—, $C_{1-4}$-alkyl-O—$C_{1-4}$-alkyl, $C_{1-4}$-alkyl-S—, $C_{1-4}$-alkyl-S(=O)—, $C_{1-4}$-alkyl-S(=O)₂—, $C_{3-6}$-cyclo alkyl-, or $C_{3-6}$-cycloalkyl-O—, wherein any alkyl and cycloalkyl group or submoiety is optionally substituted with 1 to 3 F atoms; and $R^N$ is H, $C_{1-4}$-alkyl-, $C_{1-4}$-alkyl-C(O)—, or $C_{1-4}$-alkyl-O—C(O)—, wherein any alkyl group or sub-group is straight-chained or branched unless otherwise specified, or a salt thereof.

2. The compound according to claim 1, wherein:

$R^1$ is selected from the group consisting of a monocyclic or bicyclic group having 5 to 10 ring member atoms of which 4 to 9 ring members are C atoms and 1 to 3 ring members are heteroatoms selected from N and $NR^N$, or 1 or 2 ring members are heteroatoms selected from N and $NR^N$ and 1 ring member is O or S, wherein the ring member atom attached to the —CH$_2$— group in formula I is a N atom, wherein 1 CH$_2$ ring member attached to a ring member N atom is optionally replaced by a —C(=O)— group, the monocyclic or bicyclic group is saturated or partially unsaturated, with the proviso that in bicyclic groups the ring attached to the —CH$_2$— group in formula I is not aromatic, and the bicyclic group may be a fused, bridged or spiro ring system, and any of these groups is optionally and independently substituted with 1, 2, or 3 $R^2$ groups;

or a salt thereof.

3. The compound according to claim 1, wherein $R^1$ is selected from the group consisting of:

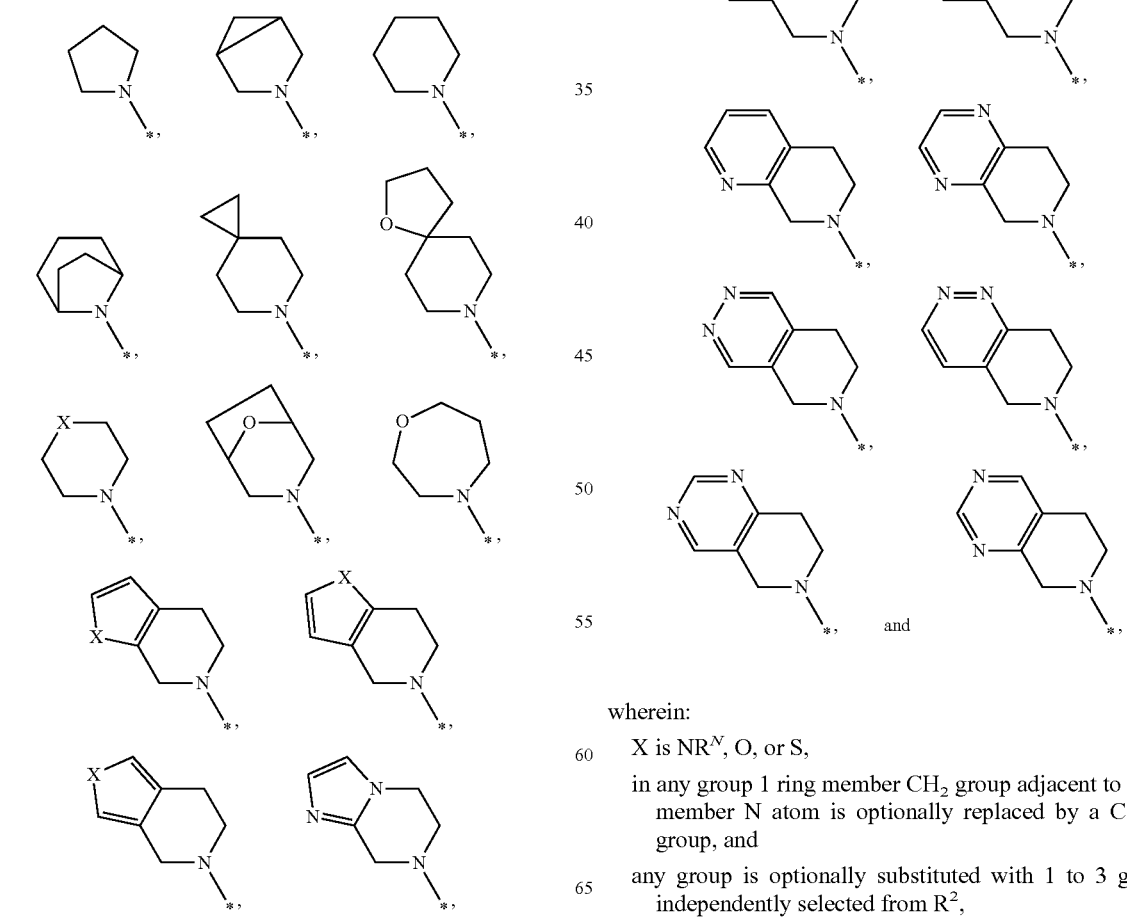

wherein:

X is $NR^N$, O, or S, in any group 1 ring member CH$_2$ group adjacent to a ring member N atom is optionally replaced by a C(=O) group, and any group is optionally substituted with 1 to 3 groups independently selected from $R^2$, or a salt thereof.

4. The compound according to claim 1, wherein:
   $R^2$ is F, Cl, $C_{1-3}$-alkyl, $F_3C-$, NC—, HO—$C_{1-3}$-alkyl, $H_3C-O-C_{1-3}$-alkyl, HO—, $C_{1-3}$-alkyl-O, $F_2HC-O-$, $F_3C-O-$, $H_3C-S(=O)_2-$, $C_{3-6}$-cycloalkyl-, or $C_{3-6}$-cycloalkyl-O—,
   or a salt thereof.

5. The compound according to claim 2, wherein:
   $R^2$ is F, Cl, $C_{1-3}$-alkyl, $F_3C-$, NC—, HO—$C_{1-3}$-alkyl, $H_3C-O-C_{1-3}$-alkyl, HO—, $C_{1-3}$-alkyl-O, $F_2HC-O-$, $F_3C-O-$, $H_3C-S(=O)_2-$, $C_{3-6}$-cycloalkyl-, or $C_{3-6}$-cycloalkyl-O—,
   or a salt thereof.

6. The compound according to claim 3, wherein:
   $R^2$ is F, Cl, $C_{1-3}$-alkyl, $F_3C-$, NC—, HO—$C_{1-3}$-alkyl, $H_3C-O-C_{1-3}$-alkyl, HO—, $C_{1-3}$-alkyl-O, $F_2HC-O-$, $F_3C-O-$, $H_3C-S(=O)_2-$, $C_{3-6}$-cycloalkyl-, or $C_{3-6}$-cycloalkyl-O—,
   or a salt thereof.

7. The compound according to claim 1, wherein:
   $R^1$ is selected from the group consisting of:

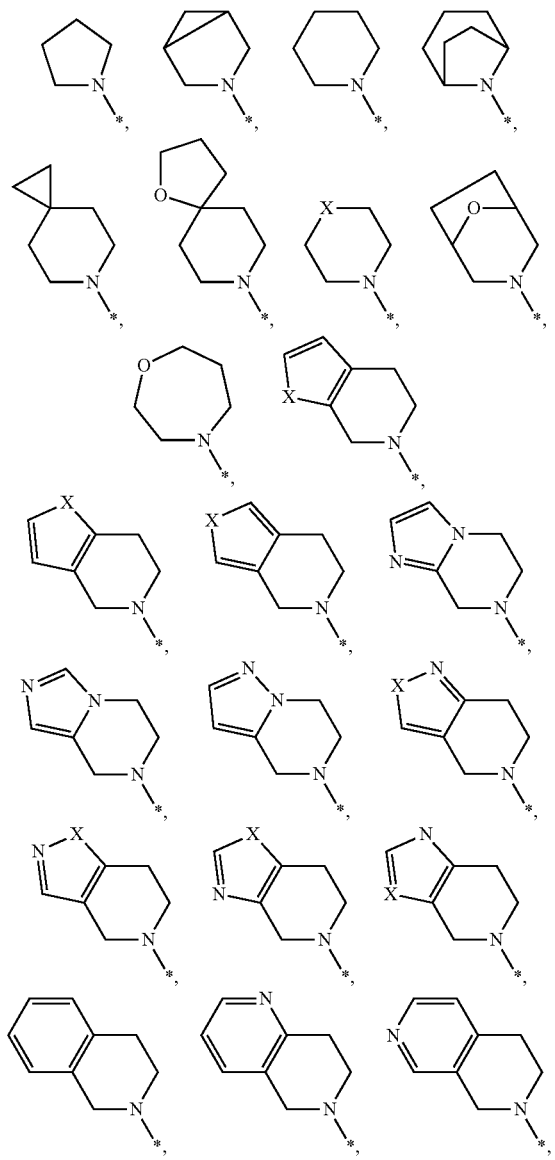

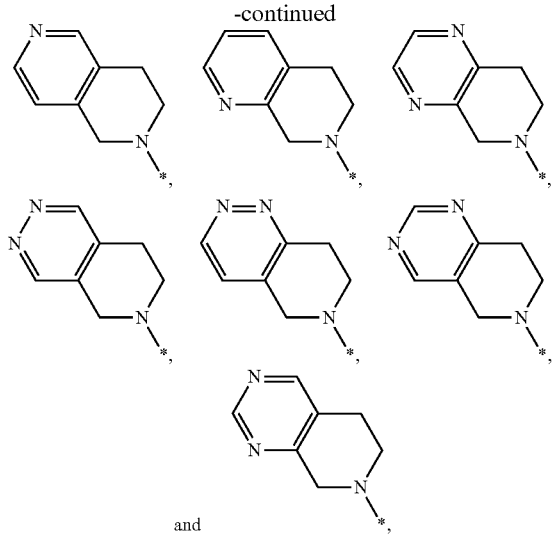

and wherein:
   X is $NR^N$, O, or S,
   in any group 1 ring member $CH_2$ group adjacent to a ring member N atom is optionally replaced by a C(=O) group, and
   any group is optionally substituted with 1 to 3 groups independently selected from $R^2$,
   $R^2$ is F, Cl, $C_{1-3}$-alkyl, NC—, HO—$C_{1-3}$-alkyl, $C_{1-3}$-alkyl-O—$C_{1-3}$-alkyl, HO—, $C_{1-3}$-alkyl-O, $H_3C-S(=O)-$, $H_3C-S(=O)_2-$, $C_{3-6}$-cycloalkyl-, or $C_{3-6}$-cycloalkyl-O—, wherein any alkyl and cycloalkyl group or submoiety is optionally substituted with 1 to 3 F atoms; and
   $R^N$ is H, $C_{1-4}$-alkyl-C(O)—, or $C_{1-4}$-alkyl-O—C(O)—,
   or a salt thereof.

8. The pharmaceutically acceptable salt of a compound according to claim 1.

9. A pharmaceutical composition comprising a compound according to claim 1 or a pharmaceutically acceptable salt thereof and an inert carrier or diluent.

10. The pharmaceutical composition according to claim 9, further comprising an additional therapeutic agent.

11. The pharmaceutical composition according to claim 10, wherein the additional therapeutic agent is selected from the group consisting of antidiabetic agents, agents for the treatment of overweight and/or obesity, and agents for the treatment of high blood pressure, heart failure, and/or atherosclerosis.

12. A method for therapeutically treating a metabolic disease selected from diabetes mellitus, type 2 diabetes, or type 1 diabetes in a patient in need thereof, the method comprising administering to the patient an effective amount of the compound according to claim 1 or a pharmaceutically acceptable salt thereof.

13. The method according to claim 12, wherein the metabolic disease is type 2 diabetes.

14. A method of therapeutically treating a condition associated with the metabolic disease of claim 12, wherein the condition associated with the metabolic disease is insulin resistance, obesity, cardiovascular disease, metabolic syndrome, or dyslipidemia.

15. The method of therapeutically treating a condition associated with the metabolic disease of claim 13, wherein the condition associated with the metabolic disease is insulin resistance, obesity, cardiovascular disease, metabolic syndrome, or dyslipidemia.

* * * * *